US005869620A

United States Patent [19]
Whitlow et al.

[11] Patent Number: 5,869,620
[45] Date of Patent: Feb. 9, 1999

[54] MULTIVALENT ANTIGEN-BINDING PROTEINS

[75] Inventors: Marc D. Whitlow, Gaithersburg; James F. Wood, Germantown, both of Md.; Karl D. Hardman, Wynnewood, Pa.; Robert E. Bird, Rockville, Md.; David Filpula, Gaithersburg, Md.; Michele Rollence, Damascus, Md.

[73] Assignee: Enzon, Inc., Piscataway, N.J.

[21] Appl. No.: 392,338

[22] Filed: Feb. 22, 1995

Related U.S. Application Data

[60] Division of Ser. No. 989,846, Nov. 20, 1992, abandoned, which is a continuation-in-part of Ser. No. 796,936, Nov. 25, 1991, abandoned, which is a continuation-in-part of Ser. No. 512,910, Apr. 25, 1990, Pat. No. 5,260,203, which is a continuation-in-part of Ser. No. 299,617, Jan. 19, 1989, Pat. No. 4,946,778, which is a continuation-in-part of Ser. No. 92,110, Sep. 2, 1987, abandoned, said Ser. No. 299,617, is a continuation-in-part of Ser. No. 902,971, Sep. 2, 1986, abandoned.

[51] Int. Cl.$^6$ ................................................ C12P 21/08
[52] U.S. Cl. .............................. 530/387.3; 424/133.1; 424/134.1; 424/135.1; 424/136.1; 435/69.6; 435/172.2; 435/172.3; 435/328
[58] Field of Search .......................... 424/133.1, 134.1, 424/135.1, 136.1; 435/69.6, 69.7, 70.21, 172.2, 172.3, 252.3, 252.33, 320.1, 328; 530/387.3; 536/23.53

[56] References Cited

U.S. PATENT DOCUMENTS

| | | | |
|---|---|---|---|
| 4,085,443 | 4/1978 | Dubois et al. | 364/900 |
| 4,266,253 | 5/1981 | Matherat | 358/903 |
| 4,355,023 | 10/1982 | Ehrlich et al. | 424/85 |
| 4,414,629 | 11/1983 | Waite | 364/300 |
| 4,434,156 | 2/1984 | Trowbridge | 424/85 |
| 4,444,878 | 4/1984 | Paulus | 435/7 |
| 4,470,925 | 9/1984 | Auditore-Hargreaves | 260/112 B |
| 4,479,895 | 10/1984 | Auditore-Hargreaves | 260/112 B |
| 4,642,334 | 2/1987 | Moore et al. | 530/388 |
| 4,704,692 | 11/1987 | Ladner | 364/496 |
| 4,816,397 | 3/1989 | Boss et al. | 435/68 |
| 4,816,567 | 3/1989 | Cabilly et al. | 530/387 |
| 4,853,871 | 8/1989 | Pantoliano et al. | 364/496 |
| 4,908,773 | 3/1990 | Pantoliano et al. | 364/496 |
| 4,939,666 | 7/1990 | Hardman | 364/496 |
| 4,946,778 | 8/1990 | Ladner et al. | 435/69.6 |
| 5,091,513 | 2/1992 | Huston et al. | 530/387.3 |
| 5,132,405 | 7/1992 | Huston et al. | 530/387.3 |
| 5,258,498 | 11/1993 | Huston et al. | 530/387.3 |
| 5,260,203 | 11/1993 | Ladner et al. | 435/172.3 |
| 5,476,786 | 12/1995 | Huston | 435/252.33 |
| 5,534,254 | 7/1996 | Huston et al. | 424/135.1 |
| 5,591,828 | 1/1997 | Bosslet et al. | 530/387.3 |

FOREIGN PATENT DOCUMENTS

| | | |
|---|---|---|
| 0 088 994 | 9/1983 | European Pat. Off. . |
| 0 120 694 | 10/1984 | European Pat. Off. . |
| 0 125 023 | 11/1984 | European Pat. Off. . |
| 0 294 703 | 12/1988 | European Pat. Off. . |
| 0 365 997 | 5/1990 | European Pat. Off. . |
| 0 506 124 | 9/1992 | European Pat. Off. . |
| WO 86/01533 | 3/1986 | WIPO . |
| WO 88/01649 | 3/1988 | WIPO . |
| WO 88/07085 | 9/1988 | WIPO . |
| WO 88/07086 | 9/1988 | WIPO . |
| WO 88/09344 | 12/1988 | WIPO . |
| WO 90/06133 | 6/1990 | WIPO . |
| WO 91/19739 | 12/1991 | WIPO . |
| WO 93/15210 | 8/1993 | WIPO . |
| WO 94/04691 | 3/1994 | WIPO . |
| WO 94/09817 | 5/1994 | WIPO . |
| WO 94/13804 | 6/1994 | WIPO . |

OTHER PUBLICATIONS

Whitlow, M. and Filpula, D., "Single–Chain Fv Proteins and Their Fusion Proteins," *Methods: A Companion to Methods in Enzymology* 2(2):97–105 (Apr. 1991).

Holliger, P. et al., "'Diabodies': Small bivalent and bispecific antibody fragments," *Proc. Natl. Acad. Sci. USA* 90:6444–6448 (Jul. 1993).

McGuinness, B. T. et al., "Phage diabody repertoires for selection of large numbers of bispecific antibody fragments," *Nature Biotechnol.* 14:1149–1154 (Sep. 1996).

Zhu, Z. et al., "High Level Secretion of a Humanized Bispecific Diabody from *Escherichia coli*," *Bio/Technol.* 14:192–196 (Feb. 1996).

McNeill, D. and Freiberger, P., "Fuzzy Delphi," in: *Fuzzy Logic*, pp. 209–227, Simon & Schuster, New York (1993).

"Nothing to lose but their chains," *The Economist* (Feb. 27, 1988).

Ahlem et al., "Regiospecific Coupling of FAB' Fragments for the Production of Synthetic Bifunctional Antibodies," *Targeted Cellular Cytotoxicity and Bispecific Antibodies*, Annapolis, MD, Poster No. 18 (Oct. 22–25, 1989).

Aldred et al., "Synthesis of rat transferrin in *Escherichia coli* containing a recombinant bacteriophage," *Chem. Abstracts* 101:189 Abstract No. 185187m (1984).

(List continued on next page.)

Primary Examiner—Robert D. Budens
Attorney, Agent, or Firm—Sterne, Kessler, Goldstein & Fox P.L.L.C.

[57] ABSTRACT

Compositions of, genetic constructions coding for, and methods for producing multivalent antigen-binding proteins are described and claimed. The methods include purification of compositions containing both monomeric and multivalent forms of single polypeptide chain molecules, and production of multivalent proteins from purified monomers. Production of multivalent proteins may occur by a concentration-dependent association of monomeric proteins, or by rearrangement of regions involving dissociation followed by reassociation of different regions. Bivalent proteins, including homobivalent and heterobivalent proteins, are made in the present invention. Genetic sequences coding for bivalent single-chain antigen-binding proteins are disclosed. Uses include all those appropriate for monoclonal and polyclonal antibodies and fragments thereof, including use as a bispecific antigen-binding molecule.

29 Claims, 39 Drawing Sheets

OTHER PUBLICATIONS

Andrew et al., "Production of a Single Chain Bispecific Antibody by Recombinant DNA Technology," *Second Intl. Conf. on Bispecific Antibodies and Targeted Cellular Cytotox.*, Seillac, France, Poster No. 21 (Oct. 9–13, 1990).

Aussage et al., "Bispecific Heteroconjugate of Anti–HB's and Anti–Fc γ RI Prepared by SPDP Method: Production and Bispecificity Analysis," *Second Intl. Conf. on Bispecific Antibodies and Targeted Cellular Cytotox.*, Seillac, France, Poster No. 41 (Oct. 9–13, 1990).

Bedzyk et al., "Immunological and Structural Characterization of a High Affinity Anti–fluorescein Single–chain Antibody," *J. Biol. Chem.* 265(30):18615–18620 (1990).

Bird et al., "Single–Chain Antigen–Binding Proteins," *Science* 242:423–426 1988).

Bishop, J.E., "Proteins Made by Genex Could Compete With Far Larger Monoclonal Antibodies," *The Wall Street Journal* (Oct. 21, 1988).

Boss et al., "Assembly of functional antibodies from immunoglobulin heavy and light chains synthesised in *E. coli*," *Nucleic Acids Res.* 12(9):3791–3806 (1985).

Boulianne et al., "Production of functional chimaeric mouse/human antibody," *Nature* 312:643–646 (1984).

Brennan et al., "Preparation of Bispecific Antibodies by Chemical Recombination of Monoclonal Immunoglobulin $G_1$ Fragments," *Science* 229:81–83 (1985).

Brewin–Wilson, D., "Cross–Linked Antibodies Turn Cytotoxic Cells against Cancer," *Oncol. Biotech. News* 3(6):7 (1989).

Colcher et al., "In Vivo Tumor Targeting of a Recombinant Single–Chain Antigen–Binding Protein," *J. Natl. Cancer Inst.* 82(14):1191–1197 (1990).

Corvalan, J.R.F. and Smith, W., "Construction and characterisation of a hybrid–hybrid monoclonal antibody recognising both carcinoembryonic antigen (CEA) and vinca alkaloids," *Cancer Immunol. Immunother.* 24:127–132 (1987).

Corvalan et al., "Tumour Therapy with Vinca Alkaloids Targeted by a Hybrid–Hybrid Monoclonal Antibody Recognising both CEA and Vinca Alkaloids," *Intl. J. Cancer Supp.* 2:22–25 (1988).

Cumber et al., "Comparative Stabilities in Vitro and in Vivo of a Recombinant Mouse Antibody FvCys Fragment and A bisFvCys Conjugate," *J. Immunol.* 149(1):120–126 (1992).

Davies, D.R. and Metzger, H., "Structural Basis of Antibody Function," *Ann. Rev. Immunol.* 1:87–177 (1983).

Field et al., "Miniantibodies produced in *E. coli*—Fusion protein expression using dual origin vector," *Dialog File 357: Biotechnology Abstracts*, Accession No. 89–05519 (1987).

Field et al., "Miniantibodies produced in *E. coli*—Hen egg lysozyme variable region monoclonal antibody gene cloning in *E. coli*," *Dialog File 357: Biotechnology Abstracts*, Accession No. 87–12016 (1987).

Foglesong et al., "Preparation and analysis of bifunctional immunoconjugates containing monoclonal antibodies OKT3 and BABR1," *Cancer Immunol. Immunother.* 30:177–184 (1989).

Foglesong et al., "Preparation and Characterization of Bifunctional Heteroconjugates Containing OKT3 and Antitumor Antibodies," *Third Intl. Conf. on Monoclonal Antibody Immunoconjugates for Cancer*, San Diego, CA, Abstract No. 65 (Feb. 4–6, 1988).

George et al., "Production of a Bispecific Antibody by Linkage of Two Recombinant Single Chain Fv Molecules," *J. Cell. Biochem. Supp.* 15E:127 Abstract No. N206 (1991).

Ghetie, v. and Moraru, I., "Preparation and Applications of Multivalent Antibodies with Dual Specificity," *Meth. Enzymol.* 92:523–543 (1983).

Gilliland et al., "Bispecific Monoclonal Antibodies and Antibody Heteroconjugates for Enhancement of T Cell Activation and for Targeting Effector Activity Against HIV–Infected Cells," *Targeted Cellular Cytotoxicity and Bispecific Antibodies*, Annapolis, MD, Conf. Abstract (Oct. 22–25, 1989).

Glennie et al., "Bispecific and Trispecific Antibody Derivatives for the Retargeting of Cytotoxic T Cells," *Targeted Cellular Cytotoxicity and Bispecific Antibodies*, Annapolis, MD, Conf. Abstract (Oct. 22–25, 1989).

Glennie et al., "Preparation and Performance of Bispecific $F(ab^1\gamma)_2$ Antibody Containing Thioether–Linked Fab 'γ Fragments," *J. Immunol.* 139(7):2367–2375 (1987).

Goldenberg et al., "Cancer Diagnosis and Therapy with Radiolabeled Antibodies," in: Immunoconjugates, Antibody Conjugates in Radioimaging and Therapy of Cancer, C.–W. Vogel, ed., Oxford University Press, NY, pp. 259–280 (1987).

Görög et al., "Use of bispecific hybrid antibodies for the development of a homogeneous enzyme immunoassay," *J. Immunol. Meth.* 123:131–140 (1989).

Griffiths et al., "Human anti–self antibodies with high specificity from phage display libraries," *EMBO J.* 12(2):725–734 (1993).

Herron, J.N., "Equilibrium and Kinetic Methodology for the Measurement of Binding Properties in Monoclonal and Polyclonal Populations of Antifluorescyl–IgG Antibodies," in: Fluorescein Hapten: An Immunological Probe, E.W. Voss, ed., CRC Press, Boca Raton, FL, pp. 49–76 (1984).

Honda et al., "A human hybrid hybridoma producing a bispecific monoclonal antibody that can target tumor cells for attack by *Pseudomonas aeruginosa* exotoxin A," *Cytotechnology* 4:59–68 (1990).

Huber, R. "Structural Basis for Antigen–Antibody Recognition," *Science* 253:702–703 (1986).

Hudson et al., "Immunoglobulin Chain Recombination Among Antidigoxin Antibodies by Hybridoma–Hybridoma Fusion," *J. Immunol.* 139(8):2715–2723 (1987).

Huston et al., "Engineering of Antibody Binding Sites to Tumor Antigens," *SBIR Grant Title Page/Abstract*, Phase I Grant, Creative BioMolecules, Inc. (1985).

Huston et al., "Engineering of Antibody Binding Sites to Tumor Antigens," *SBIR Grant Title Page/Abstract*, Phase II Grant, Creative BioMolecules, Inc. (1986).

Huston et al., "Protein engineering of antibody binding sites: Recovery of specific activity in an anti–digoxin single–chain Fv analogue produced in *Escherichia coli*," *PNAS USA* 85:5879–5883 (1988).

Jung, G., "Target Cell Induced T Cell Activation with Antibody Heteroconjugates," *Targeted Cellular Cytotoxicity and Bispecific Antibodies*, Annapolis, MD, Conf. Abstract (Oct. 22–25, 1989).

Karawajew et al., "Bispecific antibody–producing hybrid hybridomas selected by a fluorescence activated cell sorter," *J. Immunol. Meth.* 96:265–270 (1987).

Klausner, A., "Single–Chain Antibodies Become a Reality," *Bio/Technology* 4:1041,1043 (1986).

Kühn et al., "Gene Transfer, Expression, and Molecular Cloning of the Human Transferrin Receptor Gene," *Cell* 37:95–103 (1984).

Kurokawa et al., "Enhanced Fibrinolysis by a Bispecific Monoclonal Antibody Reactive to Fibrin and Tissue Plasminogen Activator," *Bio/Technology* 7:1163–1167 (1989).

Lanzavecchia, A. and Scheidegger, D., "The use of hybrid hybridomas to target human cytotoxic T lymphocytes," *Eur. J. Immunol.* 17:105–111 (1987).

Levinson et al., "Biosynthetic antibody sites: Studies of an anti–digoxin Fv region—recombinant monoclonal antibody preparation," *Dialog File 357: Biotechnology Abstracts*, Accession No. 87–11664 (1987).

Maddon et al., "The Isolation and Nucleotide Sequence of a cDNA Encoding the T Cell Surface Protein T4: A New Member of the Immunoglobulin Gene Family," *Cell* 42:93–104 (1985).

Mandache et al., "Simultaneous detection of two different cell surface antigens by electron microscopy by means of multivalent hybrid antibody with double specificity," *J. Immunol. Meth.* 42:355–365 (1981).

McGregor et al., "Spontaneous Assembly of Bivalent Single Chain Antibody Fragments in *Escherichia coli*," *Molec. Immunol.* 31(3):219–226 (1994).

Mézes et al., "Molecular Design of Anti–Tumor Single Chain Fv Species," *Third Annual IBC Intl. Conf. on Antibody Engineering*, San Diego, CA, Conf. Abstract (Dec. 14–16, 1992).

Mezzanzanica et al., "Human Ovarian Carcinoma Lysis by Cytotoxic T Cells Targeted by Bispecific Monoclonal Antibodies: Analysis of the Antibody Components," *Intl. J. Cancer* 41:609–615 (1988).

Mezzanzanica et al., "Human T Cells are Targeted Against Human Ovarian Carcinoma Cells by Bifunctional F(ab')$_2$ Antibodies Stably Joined by Thioether Linkages," *Targeted Cellular Cytotoxicity and Bispecific Antibodies*, Annapolis, MD, Poster No. 15 (Oct. 22–25, 1989).

Milstein, C. and Cuello, A.C., "Hybrid hybridomas and their use in immunohistochemistry," *Nature* 305:537–540 (1983).

Morrison, S.L., "Transfectomas Provide Novel Chimeric Antibodies," *Science* 229:1202–1207 (1985).

Morrison et al., "Chimeric human antibody molecules: Mouse antigen–binding domains with human constant region domains," *PNAS USA* 81:6851–6855 (1984).

Mota et al., "Preparation and Some Properties of Dimeric Rabbit IgG Antibody," *Molec. Immunol.* 21(7):641–645 (1984).

Munro, A., "Uses of Chimeric Antibodies," *Nature* 312:597–598 (1984).

Muraro et al., "Generation and Characterization of B72.3 Second Generation Monoclonal Antibodies Reactive with the Tumor–associated Glycoprotein 72 Antigen," *Cancer Res.* 48:4588–4596 (1988).

Neuberger et al., "Recombinant antibodies possessing novel effector functions," *Nature* 312:604–608 (1984).

Nisonoff, A. and Rivers, M.M., "Recombination of a Mixture of Univalent Antibody Fragments of Different Specificity," *Arch. Biochem. Biophys.* 93:460–462 (1961).

Oi, V.T., "Chimeric Antibodies," *BioTechniques* 4(3):214–221 (1986).

Pantoliano et al., "Conformational Stability, Folding, and Ligand–Binding Affinity of Single–Chain Fv Immunoglobulin Fragments Expressed in *Escherichia coli*," *Biochemistry* 30(42):10117–10125 (1991).

Partis et al., "Cross–Linking of Protein by ω–Maleimido Alkanoyl N–Hydroxysuccinimido Esters," *J. Protein Chem.* 2(3):263–277 (1983).

Pastan et al., "Immunotoxins," *Cell* 47:641–648 (1986).

Pimm et al., "A bispecific monoclonal antibody against methotrexate and a human tumour associated antigen augments cytotoxicity of methotrexate–carrier conjugate," *Br. J. Cancer* 61:508–513 (1990).

Raso, V. and Griffin, T., "Hybrid Antibodies with Dual Specificity for the Delivery of Ricin to Immunoglobulin–bearing Target Cells," *Cancer Res.* 41:2073–2078 (1981).

Roitt, I.M., in: Essential Immunology, 6th Ed., Blackwell Scientific Publications, Boston, MA, p. 38 (1988).

Runge et al., "Antibody Enhanced Thrombolysis: (1) Capture of Endogenous Tissue Plasminogen Activator (tPA) by a Heteroantibody Duplex and (2) Direct Targeting by an Antifibrin–tPA Conjugate In Vivo," *Clin. Res.* 35(3):643A (1987).

Scott et al., "Requirements for the Construction of Antibody Heterodimers for the Direction of Lysis of Tumors by Human T Cells," *J. Clin. Invest.* 81:1427–1433 (1988).

Segal et al., "Targeting of Cytotoxic Cells against Tumors with Heterocrosslinked, Bispecific Antibodies," in: Immune System and Cancer, Hamaoka et al., eds., Japan Sci. Soc. Press, Tokyo, Japan, pp. 323–331 (1989).

Segal et al., "Targeting of Cytotoxic Cells with Heterocrosslinked Antibodies," *Cancer Invest.* 6(1):83–92 (1988).

Snider, D.P. and Segal, D.M., "Targeted Antigen Presentation Using Crosslinked Antibody Heteroaggregates," *J. Immunol.* 139(5):1609–1616 (1987).

Songsivilai, S. and Lachmann, P.J., "Bispecific antibody: a tool for diagnosis and treatment of disease," *Clin. Exp. Immunol.* 79:315–321 (1990).

Staerz et al., "Hybrid antibodies can target sites for attack by T cells," *Nature* 314:628–631 (1985).

Sukhatme et al., "The T Cell Differentiation Antigen Leu–2/T8 Is Homologous to Immunoglobulin and T Cell Receptor Variable Regions," *Cell* 40:591–597 (1985).

Titus et al., "Human T Cells Targeted with Anti–T3 Cross–linked to Antitumor Antibody Prevent Tumor Growth in Nude Mice," *J. Immunol.* 138(11):4018–4022 (1987).

Traunecker et al., "Bispecific single chain molecules (Janusins) target cytotoxic lymphocytes on HIV infected cells," *EMBO J.* 10(12):3655–3659 (1991).

Urnovitz et al., "IgA:IgM and IgA:IgA Hybrid Hybridomas Secrete Heteropolymeric Immunoglobulins that are Polyvalent and Bispecific," *J. Immunol.* 140(2):558–563 (1988).

Van Brunt, J., "Protein Architecture: Designing from the Ground Up," *Bio/Technology* 4(4):277–283 (1986).

Vitetta et al., "Immunotoxins: A New Approach to Cancer Therapy," *Science* 219:644–650 (1983).

Waldmann, T.A., "Monoclonal Antibodies in Diagnosis and Therapy," *Science* 252:1657–1662 (1991).

Weidner et al., "Molecular Stabilization Effects of Interactions between Anti–metatype Antibodies and Liganded Antibody," *J. Biol. Chem.* 267(15):10281–10288 (1992).

Whitlow et al., "Multivalent Fvs: characterization of single–chain Fv oligomers and preparation of a bispecific Fv," *Protein Eng.* 7(8):1017–1026 (1994).

Whitlow et al., "Single–Chain Fv Proteins and Their Fusion Proteins," *Methods* 2(3):1–9 (1991).

Wood et al., "The systhesis and in vivo assembly of functional antibodies in yeast," *Nature* 314:446–449 (1985).

ANTI-B VL – ANTI-A VH    ANTI-A VL – ANTI-B VH 4-4-20 V$_L$/212/CC49 V$_H$ gene 4-4-20 V$_L$                                             10                                                  2
Asp Val Val Met Thr Gln Thr Pro Leu Ser Leu Pro Val Ser Leu Gly Asp Gln Ala Ser
GAC GTC GTT ATG ACT CAG ACA CCA CTA TCA CTT CCT GTT AGT CTA GGT GAT CAA GCC TCC
Aat II
                                                         30                                                 40
Ile Ser Cys Arg Ser Ser Gln Ser Leu Val His Ser Asn Gly Asn Thr Tyr Leu Arg Trp
ATC TCT TGC AGA TCT AGT CAG AGC CTT GTA CAC AGT AAT GGA AAC ACC TAT TTA CGT TGG 50                                                 60
Tyr Leu Gln Lys Pro Gly Gln Ser Pro Lys Val Leu Ile Tyr Lys Val Ser Asn Arg Phe
TAC CTG CAG AAG CCA GGC CAG TCT CCA AAG GTC CTG ATC TAC AAA GTT TCC AAC CGA TTT 70                                                 80
Ser Gly Val Pro Asp Arg Phe Ser Gly Ser Gly Ser Gly Thr Asp Phe Thr Leu Lys Ile
TCT GGG GTC CCA GAC AGG TTC AGT GGC AGT GGA TCA GGG ACA GAT TTC ACA CTC AAG ATC 90                                                100
Ser Arg Val Glu Ala Glu Asp Leu Gly Val Tyr Phe Cys Ser Gln Ser Thr His Val Pro
AGC AGA GTG GAG GCT GAG GAT CTG GGA GTT TAT TTC TGC TCT CAA AGT ACA CAT GTT CCG 110           212 Linker                                          120
Trp Thr Phe Gly Gly Gly Thr Lys Leu Glu Ile Lys Gly Ser Thr Ser Gly Ser Gly Lys
TGG ACG TTC GGT GGA GGC ACC AAG CTT GAA ATC AAA GGT TCT ACC TCT GGT TCT GGT AAA
                                             Hind III
                              CC49 V$_H$    130                                                           140
Ser Ser Glu Gly Lys Gly Gln Val Gln Leu Gln Gln Ser Asp Ala Glu Leu Val Lys Pro
TCC TCT GAA GGC AAA GGT CAG GTT CAG CTG CAG CAG TCT GAC GCT GAG TTG GTG AAA CCT
                                              PvuII PstI
                                                        150                                                160
Gly Ala Ser Val Lys Ile Ser Cys Lys Ala Ser Gly Tyr Thr Phe Thr Asp His Ala Ile
GGG GCT TCA GTG AAG ATT TCC TGC AAG GCT TCT GGC TAC ACC TTC ACT GAC CAT GCA ATT 170                                                180
His Trp Val Lys Gln Asn Pro Glu Gln Gly Leu Glu Trp Ile Gly Tyr Phe Ser Pro Gly
CAC TGG GTG AAA CAG AAC CCT GAA CAG GGC CTG GAA TGG ATT GGA TAT TTT TCT CCC GGA

FIG.10A 4-4-20 V$_L$/212/CC49 V$_H$ gene

```
                                  190                                    200
Asn Asp Asp Phe Lys Tyr Asn Glu Arg Phe Lys Gly Lys Ala Thr Leu Thr Ala Asp Lys
AAT GAT GAT TTT AAA TAC AAT GAG AGG TTC AAG GGC AAG GCC ACA CTG ACT GCA GAC AAA 210                                    220
Ser Ser Ser Thr Ala Tyr Val Gln Leu Asn Ser Leu Thr Ser Glu Asp Ser Ala Val Tyr
TCC TCC AGC ACT GCC TAC GTG CAG CTC AAC AGC CTG ACA TCT GAG GAT TCT GCA GTG TAT 230                                    240
Phe Cys Thr Arg Ser Leu Asn Met Ala Tyr Trp Gly Gln Gly Thr Ser Val Thr Val Ser
TTC TGT ACA AGA TCC CTG AAT ATG GCC TAC TGG GGT CAA GGA ACC TCA GTC ACC GTC TCC xxx xxx Asp
TAA TAG GAT CC
     ‾‾‾‾‾‾‾
      Bam H1
```

FIG.10A-1

CC49 V_L/212/4-4-20 V_H gene

```
CC49 V_L                              10                                    20
Asp Val Val Met Ser Gln Ser Pro Ser Ser Leu Pro Val Ser Val Gly Glu Lys Val Thr
GAC GTC GTG ATG TCA CAG TCT CCA TCC TCC CTA CCT GTG TCA GTT GGC GAG AAG GTT ACT
Aat II
                                      30                                    40
Leu Ser Cys Lys Ser Ser Gln Ser Leu Leu Tyr Ser Gly Asn Gln Lys Asn Tyr Leu Ala
TTG AGC TGC AAG TCC AGT CAG AGC CTT TTA TAT AGT GGT AAT CAA AAG AAC TAC TTG GCC 50                                    60
Trp Tyr Gln Gln Lys Pro Gly Gln Ser Pro Lys Leu Leu Ile Tyr Trp Ala Ser Ala Arg
TGG TAC CAG CAG AAA CCA GGG CAG TCT CCT AAA CTG CTG ATT TAC TGG GCA TCC GCT AGG 70                                    80
Glu Ser Gly Val Pro Asp Arg Phe Thr Gly Ser Gly Ser Gly Thr Asp Phe Thr Leu Ser
GAA TCT GGG GTC CCT GAT CGC TTC ACA GGC AGT GGA TCT GGG ACA GAT TTC ACT CTC TCC 90                                   100
Ile Ser Ser Val Lys Thr Glu Asp Leu Ala Val Tyr Tyr Cys Gln Gln Tyr Tyr Ser Tyr
ATC AGC AGT GTG AAG ACT GAA GAC CTG GCA GTT TAT TAC TGT CAG CAG TAT TAT AGC TAT 110          212 Linker              120
Pro Leu Thr Phe Gly Ala Gly Thr Lys Leu Val Leu Lys Gly Ser Thr Ser Gly Ser Gly
CCC CTC ACG TTC GGT GCT GGG ACC AAG CTT GTG CTG AAA GGC TCT ACT TCC GGT AGC GGC
                                          Hind III
                    4-4-20 V_H                                             140
Lys Ser Ser Glu Gly Lys Gly Glu Val Lys Leu Asp Glu Thr Gly Gly Gly Leu Val Gln
AAA TCT TCT GAA GGT AAA GGT GAA GTT AAA CTG GAT GAG ACT GGA GGA GGC TTG GTG CAA 150                                  160
Pro Gly Arg Pro Met Lys Leu Ser Cys Val Ala Ser Gly Phe Thr Phe Ser Asp Tyr Trp
CCT GGG AGG CCC ATG AAA CTC TCC TGT GTT GCC TCT GGA TTC ACT TTT AGT GAC TAC TGG 170                                  180
Met Asn Trp Val Arg Gln Ser Pro Glu Lys Gly Leu Glu Trp Val Ala Gln Ile Arg Asn
ATG AAC TGG GTC CGC CAG TCT CCA GAG AAA GGA CTG GAG TGG GTA GCA CAA ATT AGA AAC
```

FIG. 10B

CC49 V$_L$/212/4-4-20 V$_H$ gene

```
                          190                                       200
Lys Pro Tyr Asn Tyr Glu Thr Tyr Tyr Ser Asp Ser Val Lys Gly Arg Phe Thr Ile Ser
AAA CCT TAT AAT TAT GAA ACA TAT TAT TCA GAT TCT GTG AAA GGC AGA TTC ACC ATC TCA 210                                       220
Arg Asp Asp Ser Lys Ser Ser Val Tyr Leu Gln Met Asn Asn Leu Arg Val Glu Asp Met
AGA GAT GAT TCC AAA AGT AGT GTC TAC CTG CAA ATG AAC AAC TTA AGA GTT GAA GAC ATG 230                                       240
Gly Ile Tyr Tyr Cys Thr Gly Ser Tyr Tyr Gly Met Asp Tyr Trp Gly Gln Gly Thr Ser
GGT ATC TAT TAC TGT ACG GGT TCT TAC TAT GGT ATG GAC TAC TGG GGT CAA GGA ACC TCA

Val Thr Val Ser  *   *  Gly Ser
GTC ACC GTC TCC TAA TAA GGA TCC
                        ‾‾‾‾‾‾‾
                         Bam HI
```

FIG.10B-1

4-4-20/212 protein with single cysteine hinge

```
4-4-20 V_L                          10                                      20
Asp Val Val Met Thr Gln Thr Pro Leu Ser Leu Pro Val Ser Leu Gly Asp Gln Ala Ser
GAC GTC GTT ATG ACT CAG ACA CCA CTA TCA CTT CCT GTT AGT CTA GGT GAT CAA GCC TCC
Aat II
                                    30                                      40
Ile Ser Cys Arg Ser Ser Gln Ser Leu Val His Ser Asn Gly Asn Thr Tyr Leu Arg Trp
ATC TCT TGC AGA TCT AGT CAG AGC CTT GTA CAC AGT AAT GGA AAC ACC TAT TTA CGT TGG 50                                      60
Tyr Leu Gln Lys Pro Gly Gln Ser Pro Lys Val Leu Ile Tyr Lys Val Ser Asn Arg Phe
TAC CTG CAG AAG CCA GGC CAG TCT CCA AAG GTC CTG ATC TAC AAA GTT TCC AAC CGA TTT 70                                      80
Ser Gly Val Pro Asp Arg Phe Ser Gly Ser Gly Ser Gly Thr Asp Phe Thr Leu Lys Ile
TCT GGG GTC CCA GAC AGG TTC AGT GGC AGT GGA TCA GGG ACA GAT TTC ACA CTC AAG ATC 90                                      100
Ser Arg Val Glu Ala Glu Asp Leu Gly Val Tyr Phe Cys Ser Gln Ser Thr His Val Pro
AGC AGA GTG GAG GCT GAG GAT CTG GGA GTT TAT TTC TGC TCT CAA AGT ACA CAT GTT CCG 110         212 Linker                  120
Trp Thr Phe Gly Gly Gly Thr Lys Leu Glu Ile Lys Gly Ser Thr Ser Gly Ser Gly Lys
TGG ACG TTC GGT GGA GGC ACC AAG CTT GAA ATC AAA GGT TCT ACC TCT GGT TCT GGT AAA
                                    Hind III
                4-4-20 V_H                                                  140
Ser Ser Glu Gly Lys Gly Glu Val Lys Leu Asp Glu Thr Gly Gly Gly Leu Val Gln Pro
TCT TCT GAA GGT AAA GGT GAA GTT AAA CTG GAT GAG ACT GGA GGA GGC TTG GTG CAA CCT 150                                     160
Gly Arg Pro Met Lys Leu Ser Cys Val Ala Ser Gly Phe Thr Phe Ser Asp Tyr Trp Met
GGG AGG CCC ATG AAA CTC TCC TGT GTT GCC TCT GGA TTC ACT TTT AGT GAC TAC TGG ATG 170                                     180
Asn Trp Val Arg Gln Ser Pro Glu Lys Gly Leu Glu Trp Val Ala Gln Ile Arg Asn Lys
AAC TGG GTC CGC CAG TCT CCA GAG AAA GGA CTG GAG TGG GTA GCA CAA ATT AGA AAC AAA
```

FIG.15A 4-4-20/212     protein with single cysteine hinge

```
                                          190                                              200
Pro Tyr Asn Tyr Glu Thr Tyr Tyr Ser Asp Ser Val Lys Gly Arg Phe Thr Ile Ser Arg
CCT TAT AAT TAT GAA ACA TAT TAT TCA GAT TCT GTG AAA GGC AGA TTC ACC ATC TCA AGA 210                                              220
Asp Asp Ser Lys Ser Ser Val Tyr Leu Gln Met Asn Asn Leu Arg Val Glu Asp Met Gly
GAT GAT TCC AAA AGT AGT GTC TAC CTG CAA ATG AAC AAC TTA AGA GTT GAA GAC ATG GGT 230                                              240
Ile Tyr Tyr Cys Thr Gly Ser Tyr Tyr Gly Met Asp Tyr Trp Gly Gln Gly Thr Ser Val
ATC TAT TAC TGT ACG GGT TCT TAC TAT GGT ATG GAC TAC TGG GGT CAA GGA ACC TCG GTC
                                                                              Bst EII
            Hinge                 250
Thr Val Ser Ser Asp Lys Thr His Thr Cys *** ***
ACC GTC TCC AGT GAT AAG ACC CAT ACA TGC TAA TAG GAT CC
                                                Bam H1
pGx 5532, Gx 8932
```

FIG.15A-1

4-4-20/212 protein with two cysteine hinge 4-4-20 V$_L$                             10                            20

```
Asp Val Val Met Thr Gln Thr Pro Leu Ser Leu Pro Val Ser Leu Gly Asp Gln Ala Ser
GAC GTC GTT ATG ACT CAG ACA CCA CTA TCA CTT CCT GTT AGT CTA GGT GAT CAA GCC TCC
    Aat II
                                  30                                      40
Ile Ser Cys Arg Ser Ser Gln Ser Leu Val His Ser Asn Gly Asn Thr Tyr Leu Arg Trp
ATC TCT TGC AGA TCT AGT CAG AGC CTT GTA CAC AGT AAT GGA AAC ACC TAT TTA CGT TGG 50                                      60
Tyr Leu Gln Lys Pro Gly Gln Ser Pro Lys Val Leu Ile Tyr Lys Val Ser Asn Arg Phe
TAC CTG CAG AAG CCA GGC CAG TCT CCA AAG GTC CTG ATC TAC AAA GTT TCC AAC CGA TTT 70                                      80
Ser Gly Val Pro Asp Arg Phe Ser Gly Ser Gly Ser Gly Thr Asp Phe Thr Leu Lys Ile
TCT GGG GTC CCA GAC AGG TTC AGT GGC AGT GGA TCA GGG ACA GAT TTC ACA CTC AAG ATC 90                                     100
Ser Arg Val Glu Ala Glu Asp Leu Gly Val Tyr Phe Cys Ser Gln Ser Thr His Val Pro
AGC AGA GTG GAG GCT GAG GAT CTG GGA GTT TAT TTC TGC TCT CAA AGT ACA CAT GTT CCG 110         212 Linker                  120
Trp Thr Phe Gly Gly Gly Thr Lys Leu Glu Ile Lys Gly Ser Thr Ser Gly Ser Gly Lys
TGG ACG TTC GGT GGA GGC ACC AAG CTT GAA ATC AAA GGT TCT ACC TCT GGT TCT GGT AAA
                                     Hind III
               4-4-20 V$_H$      130                                     140
Ser Ser Glu Gly Lys Gly Glu Val Lys Leu Asp Glu Thr Gly Gly Gly Leu Val Gln Pro
TCT TCT GAA GGT AAA GGT GAA GTT AAA CTG GAT GAG ACT GGA GGA GGC TTG GTG CAA CCT 150                                     160
Gly Arg Pro Met Lys Leu Ser Cys Val Ala Ser Gly Phe Thr Phe Ser Asp Tyr Trp Met
GGG AGG CCC ATG AAA CTC TCC TGT GTT GCC TCT GGA TTC ACT TTT AGT GAC TAC TGG ATG 170                                     180
Asn Trp Val Arg Gln Ser Pro Glu Lys Gly Leu Glu Trp Val Ala Gln Ile Arg Asn Lys
AAC TGG GTC CGC CAG TCT CCA GAG AAA GGA CTG GAG TGG GTA GCA CAA ATT AGA AAC AAA
```

FIG.15B 4-4-20/212 protein with two cysteine hinge

```
                                       190                                          200
Pro Tyr Asn Tyr Glu Thr Tyr Tyr Ser Asp Ser Val Lys Gly Arg Phe Thr Ile Ser Arg
CCT TAT AAT TAT GAA ACA TAT TAT TCA GAT TCT GTG AAA GGC AGA TTC ACC ATC TCA AGA 210                                          220
Asp Asp Ser Lys Ser Ser Val Tyr Leu Gln Met Asn Asn Leu Arg Val Glu Asp Met Gly
GAT GAT TCC AAA AGT AGT GTC TAC CTG CAA ATG AAC AAC TTA AGA GTT GAA GAC ATG GGT 230                                          240
Ile Tyr Tyr Cys Thr Gly Ser Tyr Tyr Gly Met Asp Tyr Trp Gly Gln Gly Thr Ser Val
ATC TAT TAC TGT ACG GGT TCT TAC TAT GGT ATG GAC TAC TGG GGT CAA GGA ACC TCG GTC
                                                                         Bst EII
         Hinge                         250
Thr Val Ser Ser Asp Lys Thr His Thr Cys Pro Pro Cys *** ***
ACC GTC TCC AGT GAT AAG ACC CAT ACA TGC CCT CCA TGC TAA TAG GAT CC
                                                                Bam H1
pGx 5533, Gx 8933
```

FIG.15B-1

CC49/212 SCA™ protein genetic dimer

CC49 V_L

```
                                  10                                    20
Asp Val Val Met Ser Gln Ser Pro Ser Ser Leu Pro Val Ser Val Gly Glu Lys Val Thr
GAC GTC GTG ATG TCA CAG TCT CCA TCC TCC CTA CCT GTG TCA GTT GGC GAG AAG GTT ACT
Aat II
                                  30                                    40
Leu Ser Cys Lys Ser Ser Gln Ser Leu Leu Tyr Ser Gly Asn Gln Lys Asn Tyr Leu Ala
TTG AGC TGC AAG TCC AGT CAG AGC CTT TTA TAT AGT GGT AAT CAA AAG AAC TAC TTG GCC 50                                    60
Trp Tyr Gln Gln Lys Pro Gly Gln Ser Pro Lys Leu Leu Ile Tyr Trp Ala Ser Ala Arg
TGG TAC CAG CAG AAA CCA GGG CAG TCT CCT AAA CTG CTG ATT TAC TGG GCA TCC GCT AGG 70                                    80
Glu Ser Gly Val Pro Asp Arg Phe Thr Gly Ser Gly Ser Gly Thr Asp Phe Thr Leu Ser
GAA TCT GGG GTC CCT GAT CGC TTC ACA GGC AGT GGA TCT GGG ACA GAT TTC ACT CTC TCC 90                                   100
Ile Ser Ser Val Lys Thr Glu Asp Leu Ala Val Tyr Tyr Cys Gln Gln Tyr Tyr Ser Tyr
ATC AGC AGT GTG AAG ACT GAA GAC CTG GCA GTT TAT TAC TGT CAG CAG TAT TAT AGC TAT 110          212 Linker               120
Pro Leu Thr Phe Gly Ala Gly Thr Lys Leu Val Leu Lys Gly Ser Thr Ser Gly Ser Gly
CCC CTC ACG TTC GGT GCT GGG ACC AAG CTT GTG CTG AAA GGC TCT ACT TCC GGT AGC GGC
                                         Hind III
                       CC49 V_H                                        140
Lys Ser Ser Glu Gly Lys Gly Gln Val Gln Leu Gln Gln Ser Asp Ala Glu Leu Val Lys
AAA TCC TCT GAA GGC AAA GGT CAG GTT CAG CTG CAG CAG TCT GAC GCT GAG TTG GTG AAA
                                         PvuII PstI
                                 150                                   160
Pro Gly Ala Ser Val Lys Ile Ser Cys Lys Ala Ser Gly Tyr Thr Phe Thr Asp His Ala
CCT GGG GCT TCA GTG AAG ATT TCC TGC AAG GCT TCT GGC TAC ACC TTC ACT GAC CAT GCA 170                                   180
Ile His Trp Val Lys Gln Asn Pro Glu Gln Gly Leu Glu Trp Ile Gly Tyr Phe Ser Pro
ATT CAC TGG GTG AAA CAG AAC CCT GAA CAG GGC CTG GAA TGG ATT GGA TAT TTT TCT CCC
```

FIG. 16A

CC49/212 SCA™ protein genetic dimer

```
                                          190                                         200
Gly Asn Asp Asp Phe Lys Tyr Asn Glu Arg Phe Lys Gly Lys Ala Thr Leu Thr Ala Asp
GGA AAT GAT GAT TTT AAA TAC AAT GAG AGG TTC AAG GGC AAG GCC ACA CTG ACT GCA GAC 210                                         220
Lys Ser Ser Ser Thr Ala Tyr Val Gln Leu Asn Ser Leu Thr Ser Glu Asp Ser Ala Val
AAA TCC TCC AGC ACT GCC TAC GTG CAG CTC AAC AGC CTG ACA TCT GAG GAT TCT GCA GTG 230                                         240
Tyr Phe Cys Thr Arg Ser Leu Asn Met Ala Tyr Trp Gly Gln Gly Thr Ser Val Thr Val
TAT TTC TGT ACA AGA TCC CTG AAT ATG GCC TAC TGG GGT CAA GGA ACC TCA GTC ACC GTC

CC49 V_L                         250                                         260
Ser Ser Asp Val Val Met Ser Gln Ser Pro Ser Ser Leu Pro Val Ser Val Gly Glu Lys
TCC TCA GAC GTC GTG ATG TCA CAG TCT CCA TCC TCC CTA CCT GTG TCA GTT GGC GAG AAG
         Aat II 270                                         280
Val Thr Leu Ser Cys Lys Ser Ser Gln Ser Leu Leu Tyr Ser Gly Asn Gln Lys Asn Tyr
GTT ACT TTG AGC TGC AAG TCC AGT CAG AGC CTT TTA TAT AGT GGT AAT CAA AAG AAC TAC 290                                         300
Leu Ala Trp Tyr Gln Gln Lys Pro Gly Gln Ser Pro Lys Leu Leu Ile Tyr Trp Ala Ser
TTG GCC TGG TAC CAG CAG AAA CCA GGG CAG TCT CCT AAA CTG CTG ATT TAC TGG GCA TCC 310                                         320
Ala Arg Glu Ser Gly Val Pro Asp Arg Phe Thr Gly Ser Gly Ser Gly Thr Asp Phe Thr
GCT AGG GAA TCT GGG GTC CCT GAT CGC TTC ACA GGC AGT GGA TCT GGG ACA GAT TTC ACT 330                                         340
Leu Ser Ile Ser Ser Val Lys Thr Glu Asp Leu Ala Val Tyr Tyr Cys Gln Gln Tyr Tyr
CTC TCC ATC AGC AGT GTG AAG ACT GAA GAC CTG GCA GTT TAT TAC TGT CAG CAG TAT TAT 350              212 Linker               360
Ser Tyr Pro Leu Thr Phe Gly Ala Gly Thr Lys Leu Val Leu Lys Gly Ser Thr Ser Gly
AGC TAT CCC CTC ACG TTC GGT GCT GGG ACC AAG CTT GTG CTG AAA GGC TCT ACT TCC GGT
                                                Hind III
                        CC49 V_H                                                     380
Ser Gly Lys Ser Ser Glu Gly Lys Gly Gln Val Gln Leu Gln Gln Ser Asp Ala Glu Leu
AGC GGC AAA TCC TCT GAA GGC AAA GGT CAG GTT CAG CTG CAG CAG TCT GAC GCT GAG TTG
                                                 PvuII PstI
```

FIG.16B

CC49/212 SCA^TM protein genetic dimer

```
                          390                                          400
Val Lys Pro Gly Ala Ser Val Lys Ile Ser Cys Lys Ala Ser Gly Tyr Thr Phe Thr Asp
GTG AAA CCT GGG GCT TCA GTG AAG ATT TCC TGC AAG GCT TCT GGC TAC ACC TTC ACT GAC 410                                          420
His Ala Ile His Trp Val Lys Gln Asn Pro Glu Gln Gly Leu Glu Trp Ile Gly Tyr Phe
CAT GCA ATT CAC TGG GTG AAA CAG AAC CCT GAA CAG GGC CTG GAA TGG ATT GGA TAT TTT 430                                          440
Ser Pro Gly Asn Asp Asp Phe Lys Tyr Asn Glu Arg Phe Lys Gly Lys Ala Thr Leu Thr
TCT CCC GGA AAT GAT GAT TTT AAA TAC AAT GAG AGG TTC AAG GGC AAG GCC ACA CTG ACT 450                                          460
Ala Asp Lys Ser Ser Ser Thr Ala Tyr Val Gln Leu Asn Ser Leu Thr Ser Glu Asp Ser
GCA GAC AAA TCC TCC AGC ACT GCC TAC GTG CAG CTC AAC AGC CTG ACA TCT GAG GAT TCT 470                                          480
Ala Val Tyr Phe Cys Thr Arg Ser Leu Asn Met Ala Tyr Trp Gly Gln Gly Thr Ser Val
GCA GTG TAT TTC TGT ACA AGA TCC CTG AAT ATG GCC TAC TGG GGT CAA GGA ACC TCA GTC

Thr Val Ser *** *** Asp
ACC GTC TCC TAA TAG GAT CC
                    Bam H1
```

FIG.16C 4-4-20 V$_L$/217/CC49 V$_H$ gene

```
4-4-20 V_L                              10                                    20
Asp Val Val Met Thr Gln Thr Pro Leu Ser Leu Pro Val Ser Leu Gly Asp Gln Ala Ser
GAC GTC GTT ATG ACT CAG ACA CCA CTA TCA CTT CCT GTT AGT CTA GGT GAT CAA GCC TCC
Aat II
                                        30                                    40
Ile Ser Cys Arg Ser Ser Gln Ser Leu Val His Ser Asn Gly Asn Thr Tyr Leu Arg Trp
ATC TCT TGC AGA TCT AGT CAG AGC CTT GTA CAC AGT AAT GGA AAC ACC TAT TTA CGT TGG 50                                    60
Tyr Leu Gln Lys Pro Gly Gln Ser Pro Lys Val Leu Ile Tyr Lys Val Ser Asn Arg Phe
TAC CTG CAG AAG CCA GGC CAG TCT CCA AAG GTC CTG ATC TAC AAA GTT TCC AAC CGA TTT 70                                    80
Ser Gly Val Pro Asp Arg Phe Ser Gly Ser Gly Ser Gly Thr Asp Phe Thr Leu Lys Ile
TCT GGG GTC CCA GAC AGG TTC AGT GGC AGT GGA TCA GGG ACA GAT TTC ACA CTC AAG ATC 90                                    100
Ser Arg Val Glu Ala Glu Asp Leu Gly Val Tyr Phe Cys Ser Gln Ser Thr His Val Pro
AGC AGA GTG GAG GCT GAG GAT CTG GGA GTT TAT TTC TGC TCT CAA AGT ACA CAT GTT CCG 110         217 Linker                120
Trp Thr Phe Gly Gly Gly Thr Lys Leu Glu Ile Lys Gly Ser Thr Ser Gly Lys Pro Ser
TGG ACG TTC GGT GGA GGC ACC AAG CTT GAA ATC AAA GGT TCT ACC TCT GGT AAA CCA TCT
                                    Hind III
            CC49 V_H                    130                                   140
Glu Gly Lys Gly Gln Val Gln Leu Gln Gln Ser Asp Ala Glu Leu Val Lys Pro Gly Ala
GAA GGC AAA GGT CAG GTT CAG CTG CAG CAG TCT GAC GCT GAG TTG GTG AAA CCT GGG GCT
                                PvuII PstI
                                        150                                   160
Ser Val Lys Ile Ser Cys Lys Ala Ser Gly Tyr Thr Phe Thr Asp His Ala Ile His Trp
TCA GTG AAG ATT TCC TGC AAG GCT TCT GGC TAC ACC TTC ACT GAC CAT GCA ATT CAC TGG 170                                   180
Val Lys Gln Asn Pro Glu Gln Gly Leu Glu Trp Ile Gly Tyr Phe Ser Pro Gly Asn Asp
GTG AAA CAG AAC CCT GAA CAG GGC CTG GAA TGG ATT GGA TAT TTT TCT CCC GGA AAT GAT
```

FIG.19A 4-4-20 V$_L$/217/CC49 V$_H$ gene

```
                               190                                           200
Asp Phe Lys Tyr Asn Glu Arg Phe Lys Gly Lys Ala Thr Leu Thr Ala Asp Lys Ser Ser
GAT TTT AAA TAC AAT GAG AGG TTC AAG GGC AAG GCC ACA CTG ACT GCA GAC AAA TCC TCC 210                                           220
Ser Thr Ala Tyr Val Gln Leu Asn Ser Leu Thr Ser Glu Asp Ser Ala Val Tyr Phe Cys
AGC ACT GCC TAC GTG CAG CTC AAC AGC CTG ACA TCT GAG GAT TCT GCA GTG TAT TTC TGT 230                                           240
Thr Arg Ser Leu Asn Met Ala Tyr Trp Gly Gln Gly Thr Ser Val Thr Val Ser * *
ACA AGA TCC CTG AAT ATG GCC TAC TGG GGT CAA GGA ACC TCA GTC ACC GTC TCC TAA TAG
```

Asp
GAT CC
Bam H1

FIG.19A-1

CC49 V$_L$/217/4-4-20 V$_H$ gene

CC49 V$_L$

```
                              10                              20
Asp Val Val Met Ser Gln Ser Pro Ser Ser Leu Pro Val Ser Val Gly Glu Lys Val Thr
GAC GTC GTG ATG TCA CAG TCT CCA TCC TCC CTA CCT GTG TCA GTT GGC GAG AAG GTT ACT
Aat II
                              30                              40
Leu Ser Cys Lys Ser Ser Gln Ser Leu Leu Tyr Ser Gly Asn Gln Lys Asn Tyr Leu Ala
TTG AGC TGC AAG TCC AGT CAG AGC CTT TTA TAT AGT GGT AAT CAA AAG AAC TAC TTG GCC 50                              60
Trp Tyr Gln Gln Lys Pro Gly Gln Ser Pro Lys Leu Leu Ile Tyr Trp Ala Ser Ala Arg
TGG TAC CAG CAG AAA CCA GGG CAG TCT CCT AAA CTG CTG ATT TAC TGG GCA TCC GCT AGG 70                              80
Glu Ser Gly Val Pro Asp Arg Phe Thr Gly Ser Gly Ser Gly Thr Asp Phe Thr Leu Ser
GAA TCT GGG GTC CCT GAT CGC TTC ACA GGC AGT GGA TCT GGG ACA GAT TTC ACT CTC TCC 90                             100
Ile Ser Ser Val Lys Thr Glu Asp Leu Ala Val Tyr Tyr Cys Gln Gln Tyr Tyr Ser Tyr
ATC AGC AGT GTG AAG ACT GAA GAC CTG GCA GTT TAT TAC TGT CAG CAG TAT TAT AGC TAT 110           217 Linker           120
Pro Leu Thr Phe Gly Ala Gly Thr Lys Leu Val Leu Lys Gly Ser Thr Ser Gly Lys Pro
CCC CTC ACG TTC GGT GCT GGG ACC AAG CTT GTG CTG AAA GGC TCT ACT TCC GGT AAA CCA
                                  Hind III
                 4-4-20 V$_H$    130                          140
Ser Glu Gly Lys Gly Glu Val Lys Leu Asp Glu Thr Gly Gly Gly Leu Val Gln Pro Gly
TCT GAA GGT AAA GGT GAA GTT AAA CTG GAT GAG ACT GGA GGA GGC TTG GTG CAA CCT GGG 150                             160
Arg Pro Met Lys Leu Ser Cys Val Ala Ser Gly Phe Thr Phe Ser Asp Tyr Trp Met Asn
AGG CCC ATG AAA CTC TCC TGT GTT GCC TCT GGA TTC ACT TTT AGT GAC TAC TGG ATG AAC 170                             180
Trp Val Arg Gln Ser Pro Glu Lys Gly Leu Glu Trp Val Ala Gln Ile Arg Asn Lys Pro
TGG GTC CGC CAG TCT CCA GAG AAA GGA CTG GAG TGG GTA GCA CAA ATT AGA AAC AAA CCT
```

FIG.19B

CC49 V$_L$/217/4-4-20 V$_H$ gene

```
                                    190                                         200
Tyr Asn Tyr Glu Thr Tyr Tyr Ser Asp Ser Val Lys Gly Arg Phe Thr Ile Ser Arg Asp
TAT AAT TAT GAA ACA TAT TAT TCA GAT TCT GTG AAA GGC AGA TTC ACC ATC TCA AGA GAT 210                                         220
Asp Ser Lys Ser Ser Val Tyr Leu Gln Met Asn Asn Leu Arg Val Glu Asp Met Gly Ile
GAT TCC AAA AGT AGT GTC TAC CTG CAA ATG AAC AAC TTA AGA GTT GAA GAC ATG GGT ATC 230                                         240
Tyr Tyr Cys Thr Gly Ser Tyr Tyr Gly Met Asp Tyr Trp Gly Gln Gly Thr Ser Val Thr
TAT TAC TGT ACG GGT TCT TAC TAT GGT ATG GAC TAC TGG GGT CAA GGA ACC TCA GTC ACC

Val Ser *** *** Gly Ser
GTC TCC TAA TAA GGA TCC
                 Bam HI
```

FIG.19B-1

PROCESSING FILE: PolyCatA/Proc.CC-49Prep
METHOD: PREP POLY CAT A#2
INJECT VOL: 44
SAMPLING INT: 0.3 SECONDS

CHROMATOGRAM:

ANALYSIS: CHANNEL A

| PEAK NO. | TIME | TYPE | HEIGHT($\mu$V) | AREA($\mu$V-SEC) | AREA% |
|---|---|---|---|---|---|
| 1 | 17.090 | N1 | 1651 | 348239 | 0.778 |
| 2 | 18.940 | N2 | 8014 | 669441 | 1.496 |
| 3 | 21.775 | N3 | 104401 | 8617252 | 19.263 |
| 4 | 30.100 | N4 | 74925 | 9753616 | 21.804 |
| 5 | 33.455 | N5 | 106864 | 15749605 | 35.208 |
| 6 | 38.940 | N6 | 17296 | 2833701 | 6.334 |
| 7 | 42.010 | N7 | 12645 | 1637917 | 3.661 |
| 8 | 44.640 | N8 | 9287 | 1968584 | 4.400 |
| 9 | 57.055 | N9 | 13767 | 2012338 | 4.498 |
| 10 | 57.610 | N10 | 9323 | 210914 | 0.471 |
| 11 | 58.240 | X11 | 6824 | 930855 | 2.080 |
| TOTAL AREA | | | | 44732462 | 99.993 |

PROCESSING FILE: PolyCatA/Proc.CC-49Prep
METHOD: CC-49 QC SIZE-EXCLUSION
INJECT VOL: .05
SAMPLING INT: 0.1 SECONDS

CHROMATOGRAM:

| ANALYSIS: | CHANNEL A | | | | |
|---|---|---|---|---|---|
| PEAK NO. | TIME | TYPE | HEIGHT($\mu$V) | AREA($\mu$V-SEC) | AREA% |
| 1 | 19.370 | N1 | 797 | 41706 | 5.694 |
| 2 | 20.525 | N2 | 11789 | 657280 | 89.737 |
| 3 | 22.851 | N3 | 1227 | 33466 | 4.569 |
| TOTAL AREA | | | | 732452 | 100.000 |

PROCESSING FILE: PolyCatA/Proc.CC-49Prep
METHOD: CC-49 QC SIZE-EXCLUSION
INJECT VOL: .05
SAMPLING INT: 0.1 SECONDS

CHROMATOGRAM:

| ANALYSIS: | CHANNEL A | | | | |
|---|---|---|---|---|---|
| PEAK NO. | TIME | TYPE | HEIGHT(μV) | AREA(μV-SEC) | AREA% |
| 1 | 19.133 | N1 | 14211 | 749671 | 88.214 |
| 2 | 20.538 | N2 | 1863 | 100154 | 11.785 |
| TOTAL AREA | | | | 849825 | 99.999 |

PROCESSING FILE: PolyCatA/Proc.CC-49Prep
METHOD: CC-49 QC SIZE-EXCLUSION
INJECT VOL: .05
SAMPLING INT: 0.1 SECONDS

CHROMATOGRAM:

| ANALYSIS: | CHANNEL A | | | | |
|---|---|---|---|---|---|
| PEAK NO. | TIME | TYPE | HEIGHT($\mu$V) | AREA($\mu$V-SEC) | AREA% |
| 1 | 19.163 | N1 | 17550 | 876502 | 83.039 |
| 2 | 20.435 | N2 | 2981 | 179029 | 16.961 |
| TOTAL AREA | | | | 1055531 | 100.000 |

MULTIVALENT ANTIGEN-BINDING PROTEINS

CROSS-REFERENCE TO RELATED APPLICATIONS

This application is a divisional of U.S. patent application Ser. No. 07/989,846, filed Nov. 20, 1992, now abandoned, which is a continuation-in-part of U.S. patent application Ser. No. 07/796,936, filed Nov. 25, 1991, now abandoned, which is a continuation-in-part of U.S. patent application Ser. No. 07/512,910 filed Apr. 25, 1990, issued as U.S. Pat. No. 5,260,203 which is a continuation-in-part of Ser. No. 07/299,617, filed Jan. 19, 1989, issued as U.S. Pat. No. 4,946,778, which was a continuation-in-part of Ser. No. 07/092,110, filed Sep. 2, 1987, now abandoned and Ser. No. 06/902,971, filed Sep. 2, 1986, now abandoned, the contents of all of which are fully incorporated herein by reference.

This invention was made with Government Support under SBIR Grant 5R44 GM 39662-03 awarded by the National Institutes of Health, National Institute of General Medical Sciences. The Government has certain rights in the invention.

BACKGROUND OF THE INVENTION

1. Field of the Invention

The present invention relates generally to the production of antigen-binding molecules. More specifically, the invention relates to multivalent forms of antigen-binding proteins. Compositions of, genetic constructions for, methods of use, and methods for producing these multivalent antigen-binding proteins are disclosed.

2. Description of the Background Art

Antibodies are proteins generated by the immune system to provide a specific molecule capable of complexing with an invading molecule, termed an antigen. FIG. 14 shows the structure of a typical antibody molecule. Natural antibodies have two identical antigen-binding sites, both of which are specific to a particular antigen. The antibody molecule "recognizes" the antigen by complexing its antigen-binding sites with areas of the antigen termed epitopes. The epitopes fit into the conformational architecture of the antigen-binding sites of the antibody, enabling the antibody to bind to the antigen.

The antibody molecule is composed of two identical heavy and two identical light polypeptide chains, held together by interchain disulfide bonds (see FIG. 14). The remainder of this discussion will refer only to one light/heavy pair of chains, as each light/heavy pair is identical. Each individual light and heavy chain folds into regions of approximately 110 amino acids, assuming a conserved three-dimensional conformation. The light chain comprises one variable region (termed $V_L$) and one constant region ($C_L$), while the heavy chain comprises one variable region ($V_H$) and three constant regions ($C_H1$, $C_H2$ and $C_H3$). Pairs of regions associate to form discrete structures as shown in FIG. 14. In particular, the light and heavy chain variable regions, $V_L$ and $V_H$, associate to form an "$F_V$" area which contains the antigen-binding site.

The variable regions of both heavy and light chains show considerable variability in structure and amino acid composition from one antibody molecule to another, whereas the constant regions show little variability. The term "variable" as used in this specification refers to the diverse nature of the amino acid sequences of the antibody heavy and light chain variable regions. Each antibody recognizes and binds antigen through the binding site defined by the association of the heavy and light chain variable regions into an $F_V$ area. The light-chain variable region $V_L$ and the heavy-chain variable region $V_H$ of a particular antibody molecule have specific amino acid sequences that allow the antigen-binding site to assume a conformation that binds to the antigen epitope recognized by that particular antibody.

Within the variable regions are found regions in which the amino acid sequence is extremely variable from one antibody to another. Three of these so-called "hypervariable" regions or "complementarity-determining regions" (CDR's) are found in each of the light and heavy chains. The three CDR's from a light chain and the three CDR's from a corresponding heavy chain form the antigen-binding site.

Cleavage of the naturally-occurring antibody molecule with the proteolytic enzyme papain generates fragments which retain their antigen-binding site. These fragments, commonly known as Fab's (for Fragment, antigen binding site) are composed of the $C_L$, $V_L$, $C_H1$ and $V_H$ regions of the antibody. In the Fab the light chain and the fragment of the heavy chain are covalently linked by a disulfide linkage.

Recent advances in immunobiology, recombinant DNA technology, and computer science have allowed the creation of single polypeptide chain molecules that bind antigen. These single-chain antigen-binding molecules incorporate a linker polypeptide to bridge the individual variable regions, $V_L$ and $V_H$, into a single polypeptide chain. A computer-assisted method for linker design is described more particularly in U.S. Pat. No. 4,704,692, issued to Ladner et al. in November, 1987, and incorporated herein by reference. A description of the theory and production of single-chain antigen-binding proteins is found in U.S. Pat. No. 4,946,778 (Ladner et al.), issued Aug. 7, 1990, and incorporated herein by reference. The single-chain antigen-binding proteins produced under the process recited in U.S. Pat. No. 4,946,778 have binding specificity and affinity substantially similar to that of the corresponding Fab fragment.

Bifunctional, or bispecific, antibodies have antigen binding sites of different specificities. Bispecific antibodies have been generated to deliver cells, cytotoxins, or drugs to specific sites. An important use has been to deliver host cytotoxic cells, such as natural killer or cytotoxic T cells, to specific cellular targets. (U. D. Staerz, O. Kanagawa, M. J. Bevan, *Nature* 314:628 (1985); S. Songilvilai, P. J. Lachmann, *Clin. Exp. Immunol.* 79:315 (1990)). Another important use has been to deliver cytotoxic proteins to specific cellular targets. (V. Raso, T. Griffin, *Cancer Res.* 41:2073 (1981); S. Honda, Y. Ichimori, S. Iwasa, *Cytotechnology* 4:59 (1990)). Another important use has been to deliver anti-cancer non-protein drugs to specific cellular targets (J. Corvalan, W. Smith, V. Gore, *Intl. J. Cancer Suppl.* 2:22 (1988); M. Pimm et al., *British J. of Cancer* 61:508 (1990)). Such bispecific antibodies have been prepared by chemical cross-linking (M. Brennan et al., *Science* 229:81 (1985)), disulfide exchange, or the production of hybrid-hybridomas (quadromas). Quadromas are constructed by fusing hybridomas that secrete two different types of antibodies against two different antigens (Kurokawa, T. et al., *Biotechnology* 7.1163 (1989)).

SUMMARY OF THE INVENTION

This invention relates to the discovery that multivalent forms of single-chain antigen-binding proteins have significant utility beyond that of the monovalent single-chain antigen-binding proteins. A multivalent antigen-binding protein has more than one antigen-binding site. Enhanced binding activity, di- and multi-specific binding, and other novel uses of multivalent antigen-binding proteins have been demonstrated or are envisioned here. Accordingly, the invention is directed to multivalent forms of single-chain antigen-binding proteins, compositions of multivalent and single-chain antigen-binding proteins, methods of making and purifying multivalent forms of single-chain antigen-binding proteins, and uses for multivalent forms of single-chain antigen-binding proteins. The invention provides a multivalent antigen-binding protein comprising two or more single-chain protein molecules, each single-chain molecule comprising a first polypeptide comprising the binding portion of the variable region of an antibody heavy or light chain; a second polypeptide comprising the binding portion of the variable region of an antibody heavy or light chain; and a peptide linker linking the first and second polypeptides into a single-chain protein.

Also provided is a composition comprising a multivalent antigen-binding protein substantially free of single-chain molecules.

Also provided is an aqueous composition comprising an excess of multivalent antigen-binding protein over single-chain molecules.

A method of producing a multivalent antigen-binding protein is provided, comprising the steps of producing a composition comprising multivalent antigen-binding protein and single-chain molecules, each single-chain molecule comprising a first polypeptide comprising the binding portion of the variable region of an antibody heavy or light chain; a second polypeptide comprising the binding portion of the variable region of an antibody heavy or light chain; and a peptide linker linking the first and second polypeptides into a single-chain molecule; separating the multivalent protein from the single-chain molecules; and recovering the multivalent protein.

Also provided is a method of producing multivalent antigen-binding protein, comprising the steps of producing a composition comprising single-chain molecules as previously defined; dissociating the single-chain molecules; reassociating the single-chain molecules; separating the resulting multivalent antigen-binding proteins from the single-chain molecules; and recovering the multivalent proteins.

Also provided is another method of producing a multivalent antigen-binding protein, comprising the step of chemically cross-linking at least two single-chain antigen-binding molecules.

Also provided is another method of producing a multivalent antigen-binding protein, comprising the steps of producing a composition comprising single-chain molecules as previously defined; concentrating said single-chain molecules; separating said multivalent protein from said single-chain molecules; and finally recovering said multivalent protein.

Also provided is another method of producing a multivalent antigen-binding protein comprising two or more single-chain molecules, each single-chain molecule as previously defined, said method comprising: providing a genetic sequence coding for said single-chain molecule; transforming a host cell or cells with said sequence; expressing said sequence in said host or hosts; and recovering said multivalent protein.

Another aspect of the invention includes a method of detecting an antigen in or suspected of being in a sample, which comprises contacting said sample with the multivalent antigen-binding protein of claim 1 and detecting whether said multivalent antigen-binding protein has bound to said antigen.

Another aspect of the invention includes a method of imaging the internal structure of an animal, comprising administering to said animal an effective amount of a labeled form of the multivalent antigen-binding protein of claim 1 and measuring detectable radiation associated with said animal.

Another aspect of the invention includes a composition comprising an association of a multivalent antigen-binding protein with a therapeutically or diagnostically effective agent.

Another aspect of this invention is a single-chain protein comprising: a first polypeptide comprising the binding portion of the variable region of an antibody light chain; a second polypeptide comprising the binding portion of the variable region of an antibody light chain; a peptide linker linking said first and second polypeptides (a) and (b) into said single-chain protein.

Another aspect of the present invention includes the genetic constructions encoding the combinations of regions $V_L$—$V_L$ and $V_H$—$V_H$ for single-chain molecules, and encoding multivalent antigen-binding proteins.

Another part of this invention is a multivalent single-chain antigen-binding protein comprising: a first polypeptide comprising the binding portion of the variable region of an antibody heavy or light chain; a second polypeptide comprising the binding portion of the variable region of an antibody heavy or light chain; a peptide linker linking said first and second polypeptides (a) and (b) into said multivalent protein; a third polypeptide comprising the binding portion of the variable region of an antibody heavy or light chain; a fourth polypeptide comprising the binding portion of the variable region of an antibody heavy or light chain; a peptide linker linking said third and fourth polypeptides (d) and (e) into said multivalent protein; and a peptide linker linking said second and third polypeptides (b) and (d) into said multivalent protein. Also included are genetic constructions coding for this multivalent single-chain antigen-binding protein.

Also included are replicable cloning or expression vehicles including plasmids, hosts transformed with the aforementioned genetic sequences, and methods of producing multivalent proteins with the sequences, transformed hosts, and expression vehicles.

Methods of use are provided, such as a method of using the multivalent antigen-binding protein to diagnose a medical condition; a method of using the multivalent protein as a carrier to image the specific bodily organs of an animal; a therapeutic method of using the multivalent protein to treat a medical condition; and an immunotherapeutic method of conjugating a multivalent protein with a therapeutically or diagnostically effective agent. Also included are labelled multivalent proteins, improved immunoassays using them, and improved immunoaffinity purifications.

An advantage of using multivalent antigen-binding proteins instead of single-chain antigen-binding molecules or Fab fragments lies in the enhanced binding ability of the multivalent form. Enhanced binding occurs because the multivalent form has more binding sites per molecule. Another advantage of the present invention is the ability to use multivalent antigen-binding proteins as multi-specific binding molecules.

An advantage of using multivalent antigen-binding proteins instead of whole antibodies, is the enhanced clearing of the multivalent antigen-binding proteins from the serum due to their smaller size as compared to whole antibodies which may afford lower background in imaging applications. Multivalent antigen-binding proteins may penetrate solid tumors better than monoclonals, resulting in better tumor-fighting ability. Also, because they are smaller and lack the Fc component of intact antibodies, the multivalent antigen-binding proteins of the present invention may be less immunogenic than whole antibodies. The Fc component of whole antibodies also contains binding sites for liver, spleen and certain other cells and its absence should thus reduce accumulation in non-target tissues.

Another advantage of multivalent antigen-binding proteins is the ease with which they may be produced and engineered, as compared to the myeloma-fusing technique pioneered by Kohler and Milstein that is used to produce whole antibodies.

BRIEF DESCRIPTION OF THE DRAWINGS

The present invention as defined in the claims can be better understood with reference to the text and to the following drawings:

FIG. 10A is an amino acid (SEQ ID NO. 11) and nucleotide (SEQ ID NO. 10) sequence of the single-chain protein comprising the 4-4-20 $V_L$ region connected through the 212 linker polypeptide to the CC49 $V_H$ region.

FIG. 10B is an amino acid (SEQ ID NO. 13) and nucleotide (SEQ ID NO. 12) sequence of the single-chain protein comprising the CC49 $V_L$ region connected through the 212 linker polypeptide to the 4-4-20 $V_H$ region.

FIG. 15A is an amino acid (SEQ ID NO. 15) and nucleotide (SEQ ID NO. 14) sequence of the 4-4-20/212 single-chain antigen-binding protein with a single cysteine hinge.

FIG. 15B is an amino acid (SEQ ID NO. 17) and nucleotide (SEQ. ID NO. 16) sequence of the 4-4-20/212 single-chain antigen-binding protein with the two-cysteine hinge.

FIG. 16 shows the amino acid (SEQ ID NO. 19) and nucleotide (SEQ ID NO. 18) sequence of a divalent CC49/212 single-chain antigen-binding protein.

FIG. 19A is an amino acid (SEQ ID NO. 21) and nucleotide (SEQ ID NO. 20) sequence of the single-chain polypeptide comprising the 4-4-20 $V_L$ region connected through the 217 linker polypeptide to the CC49 $V_H$ region.

FIG. 19B is an amino acid (SEQ ID NO. 23) and nucleotide (SEQ ID NO. 22) sequence of the single-chain polypeptide comprising the CC49 $V_L$ region connected through the 217 linker polypeptide to the 4-4-20 $V_H$ region.

DETAILED DESCRIPTION OF THE PREFERRED EMBODIMENTS

Figure 1A:
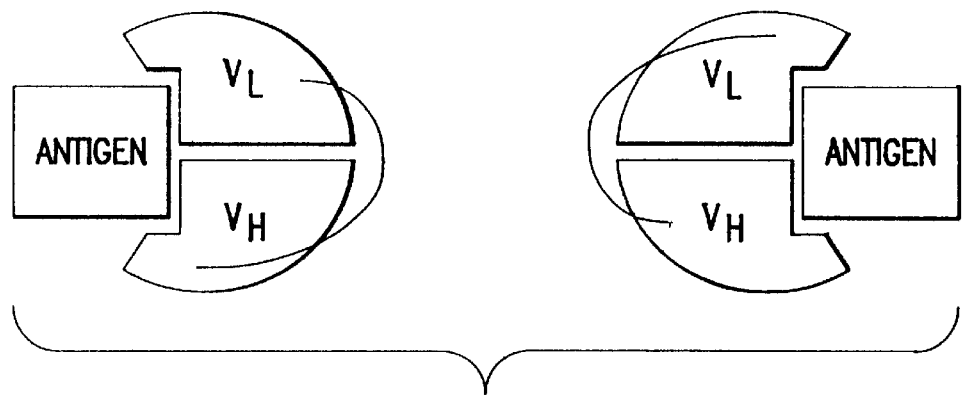
FIG. 1A is a schematic two-dimensional representation of two identical single-chain antigen-binding protein molecules, each comprising a variable light chain region ($V_L$), a variable heavy chain region ($V_H$), and a polypeptide linker joining the two regions. The single-chain antigen-binding protein molecules are shown binding antigen in their antigen-binding sites.

This invention relates to the discovery that multivalent forms of single-chain antigen-binding proteins have significant utility beyond that of the monovalent single-chain antigen-binding proteins. A multivalent antigen-binding protein has more than one antigen-binding site. For the purposes of this application, "valent" refers to the numerosity of antigen binding sites. Thus, a bivalent protein refers to a protein with two binding sites. Enhanced binding activity, bi- and multi-specific binding, and other novel uses of multivalent antigen-binding proteins have been demonstrated or are envisioned here. Accordingly, the invention is directed to multivalent forms of single-chain antigen-binding proteins, compositions of multivalent and single-chain antigen-binding proteins, methods of making and purifying multivalent forms of single-chain antigen-binding proteins, and new and improved uses for multivalent forms of single-chain antigen-binding proteins. The invention provides a multivalent antigen-binding protein comprising two or more single-chain protein molecules, each single-chain molecule comprising a first polypeptide comprising the binding portion of the variable region of an antibody heavy or light chain; a second polypeptide comprising the binding portion of the variable region of an antibody heavy or light chain; and a peptide linker linking the first and second polypeptides into a single-chain protein.

The term "multivalent" means any assemblage, covalently or non-covalently joined, of two or more single-chain proteins, the assemblage having more than one antigen-binding site. The single-chain proteins composing the assemblage may have antigen-binding activity, or they may lack antigen-binding activity individually but be capable of assembly into active multivalent antigen-binding proteins. The term "multivalent" encompasses bivalent, trivalent, tetravalent, etc. It is envisioned that multivalent forms above bivalent may be useful for certain applications.

A preferred form of the multivalent antigen-binding protein comprises bivalent proteins, including heterobivalent and homobivalent forms. The term "bivalent" means an assemblage of single-chain proteins associated with each other to form two antigen-binding sites. The term "heterobivalent" indicates multivalent antigen-binding proteins that are bispecific molecules capable of binding to two different antigenic determinants. Therefore, heterobivalent proteins have two antigen-binding sites that have different binding specificities. The term "homobivalent" indicates that the two binding sites are for the same antigenic determinant.

The terms "single-chain molecule" or "single-chain protein" are used interchangeably here. They are structurally defined as comprising the binding portion of a first polypeptide from the variable region of an antibody, associated with the binding portion of a second polypeptide from the variable region of an antibody, the two polypeptides being joined by a peptide linker linking the first and second polypeptides into a single polypeptide chain. The single polypeptide chain thus comprises a pair of variable regions connected by a polypeptide linker. The regions may associate to form a functional antigen-binding site, as in the case wherein the regions comprise a light-chain and a heavy-chain variable region pair with appropriately paired complementarity determining regions (CDRs). In this case, the single-chain protein is referred to as a "single-chain antigen-binding protein" or "single-chain antigen-binding molecule."

Alternatively, the variable regions may have unnaturally paired CDRs or may both be derived from the same kind of antibody chain, either heavy or light, in which case the resulting single-chain molecule may not display a functional antigen-binding site. The single-chain antigen-binding protein molecule is more fully described in U.S. Pat. No. 4,946,778 (Ladner et al.), and incorporated herein by reference.

Without being bound by any particular theory, the inventors speculate on several models which can equally explain the phenomenon of multivalence. The inventors' models are presented herein for the purpose of illustration only, and are not to be construed as limitations upon the scope of the invention. The invention is useful and operable regardless of the precise mechanism of multivalence.

Figure 1B:
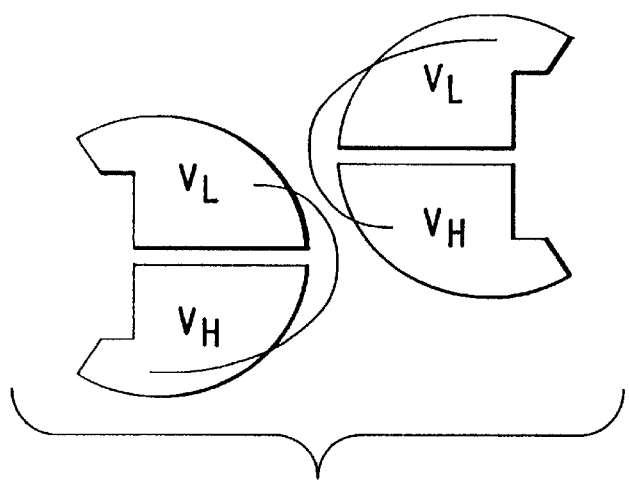
FIG. 1B depicts a hypothetical homodivalent antigen-binding protein formed by association of the polypeptide linkers of two monovalent single-chain antigen-binding proteins from FIG. 1A (the Association model). The divalent antigen-binding protein is formed by the concentration-driven association of two identical single-chain antigen-binding protein molecules.
Figure 1C:
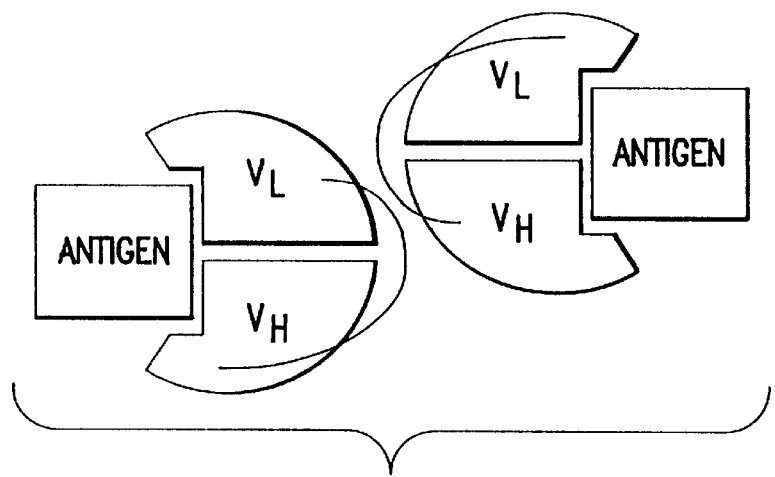
FIG. 1C depicts the hypothetical divalent protein of FIG. 1B with bound antigen molecules occupying both antigen-binding sites.

FIG. 1 depicts the first hypothetical model for the creation of a multivalent protein, the "Association" model. FIG. 1A shows two monovalent single-chain antigen-binding proteins, each composed of a $V_L$, a $V_H$, and a linker polypeptide covalently bridging the two. Each monovalent single-chain antigen-binding protein is depicted having an identical antigen-binding site containing antigen. FIG. 1B shows the simple association of the two single-chain antigen-binding proteins to create the bivalent form of the multivalent protein. It is hypothesized that simple hydrophobic forces between the monovalent proteins are responsible for their association in this manner. The origin of the multivalent proteins may be traceable to their concentration dependence. The monovalent units retain their original association between the $V_H$ and $V_L$ regions. FIG. 1C shows the newly-formed homobivalent protein binding two identical antigen molecules simultaneously. Homobivalent antigen-binding proteins are necessarily monospecific for antigen.

Figure 2A:
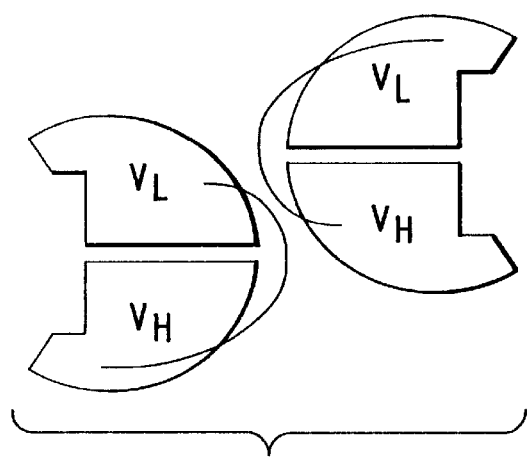
FIG. 2A depicts the hypothetical homodivalent protein of FIG. 1B.
Figure 2B:
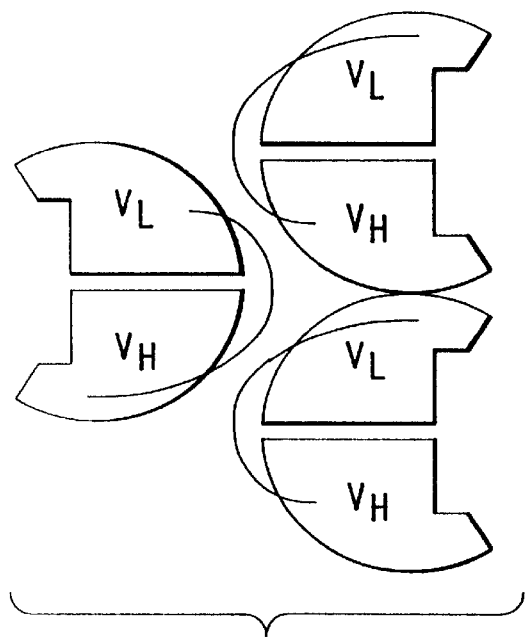
FIG. 2B depicts three single-chain antigen-binding protein molecules associated in a hypothetical trimer.
Figure 2C:
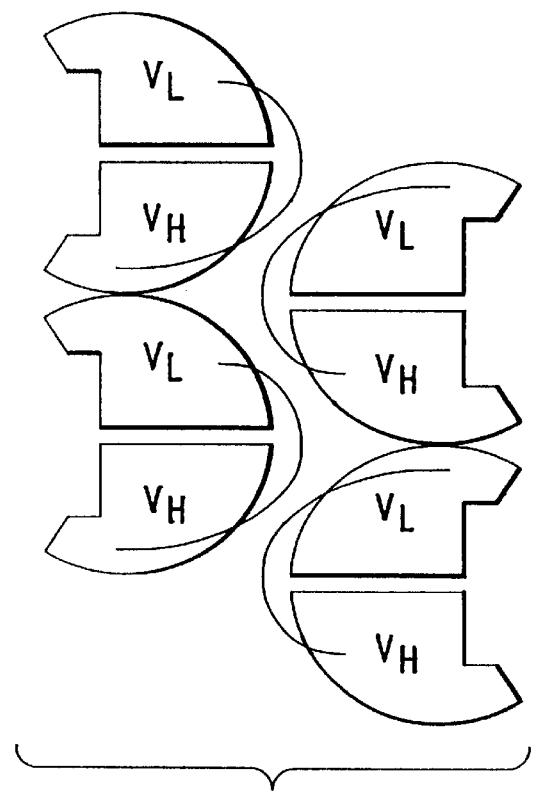
FIG. 2C depicts a hypothetical tetramer of four single-chain antigen-binding protein molecules.

Homovalent proteins are depicted in FIGS. 2A through 2C formed according to the Association model. FIG. 1A depicts a homobivalent protein, FIG. 2B a trivalent protein, and FIG. 2C a tetravalent protein. Of course, the limitations of two-dimensional images of three-dimensional objects must be taken into account. Thus, the actual spatial arrangement of multivalent proteins can be expected to vary somewhat from these figures.

Figure 3A:
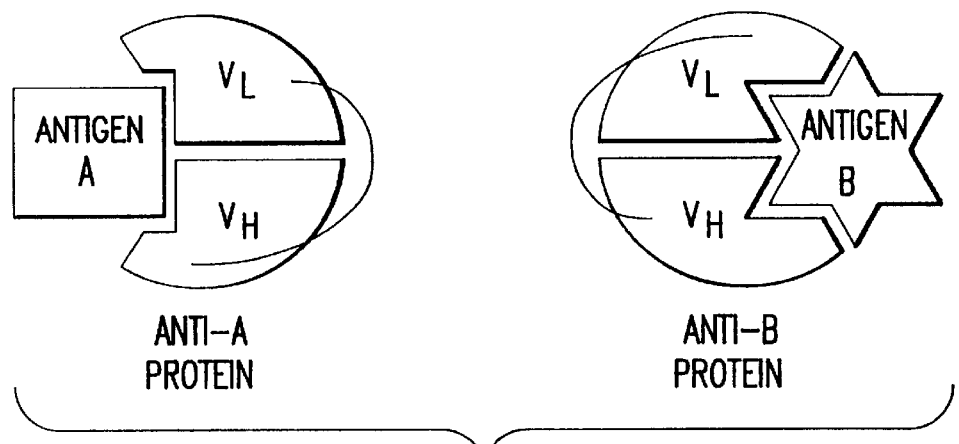
FIG. 3A depicts two separate and distinct monovalent single-chain antigen-binding proteins, Anti-A single-chain antigen-binding protein and Anti-B single-chain antigen-binding protein, with different antigen specificities, each individually binding either Antigen A or Antigen B.
Figure 3B:
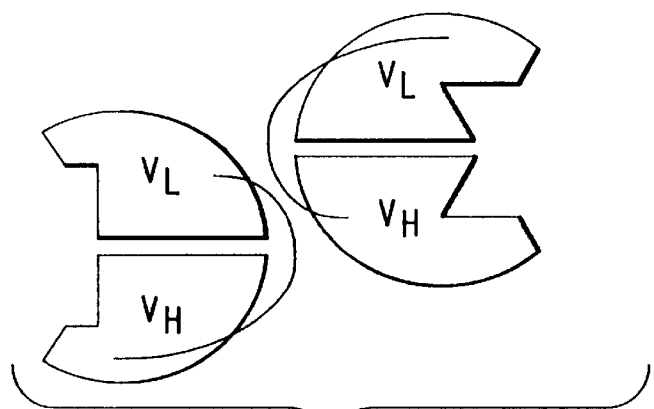
FIG. 3B depicts a hypothetical bispecific heterodivalent antigen-binding protein formed from the single-chain antigen-binding proteins of FIG. 3A according to the Association model.
Figure 3C:
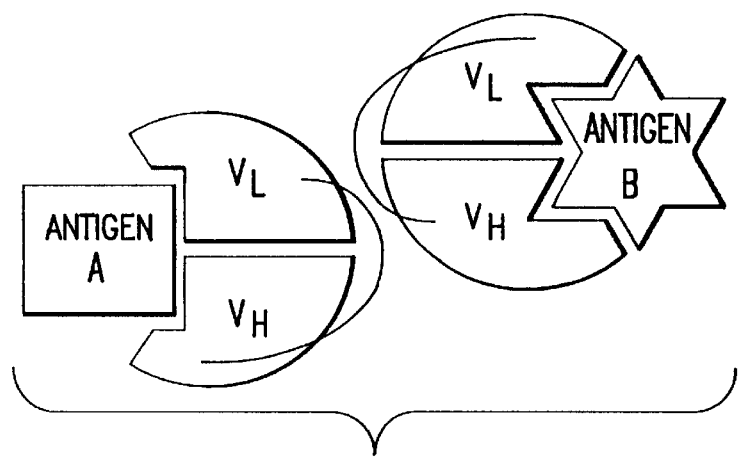
FIG. 3C depicts the hypothetical heterodivalent antigen-binding protein of FIG. 3B binding bispecifically, i.e., binding the two different antigens, A and B.

A heterobivalent antigen-binding protein has two different binding sites, the sites having different binding specificities. FIGS. 3A through C depict the Association model pathway to the creation of a heterobivalent protein. FIG. 3A shows two monovalent single-chain antigen-binding proteins, Anti-A single-chain antigen-binding protein and Anti-B single-chain antigen-binding protein, with antigen types A and B occupying the respective binding sites. FIG. 3B depicts the heterobivalent protein formed by the simple association of the original monovalent proteins. FIG. 3C shows the heterobivalent protein having bound antigens A and B into the antigen-binding sites. FIG. 3C therefore shows the heterobivalent protein binding in a bispecific manner.

Figure 4A:
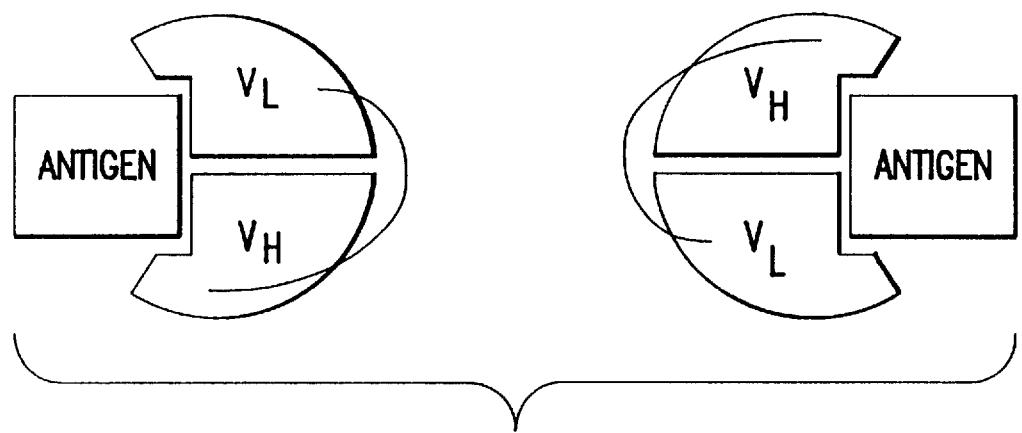
FIG. 4A depicts two identical single-chain antigen-binding protein molecules, each having a variable light chain region ($V_L$), a variable heavy chain region ($V_H$), and a polypeptide linker joining the two regions. The single-chain antigen-binding protein molecules are shown binding identical antigen molecules in their antigen-binding sites.
Figure 4B:
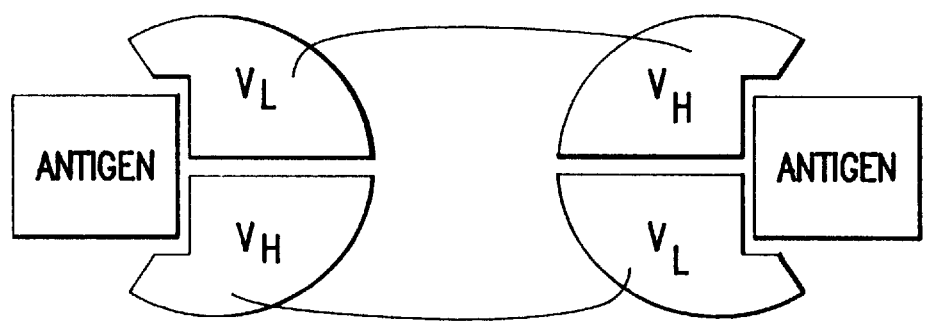
FIG. 4B depicts a hypothetical homodivalent protein formed by the rearrangement of the $V_L$ and $V_H$ regions shown in FIG. 4A (the Rearrangement model). Also shown is bound antigen.

An alternative model for the formation of multivalent antigen-binding proteins is shown in FIGS. 4 through 6. This "Rearrangement" model hypothesizes the dissociation of the variable region interface by contact with dissociating agents such as guanidine hydrochloride, urea, or alcohols such as ethanol, either alone or in combination. Combinations and relevant concentration ranges of dissociating agents are recited in the discussion concerning dissociating agents, and in Example 2. Subsequent re-association of dissociated regions allows variable region recombination differing from the starting single-chain proteins, as depicted in FIG. 4B. The homobivalent antigen-binding protein of FIG. 4B is formed from the parent single-chain antigen-binding proteins shown in FIG. 4A, the recombined bivalent protein having $V_L$ and $V_H$ from the parent monovalent single-chain proteins. The homobivalent protein of FIG. 4B is a fully functional monospecific bivalent protein, shown actively binding two antigen molecules.

Figure 5A:
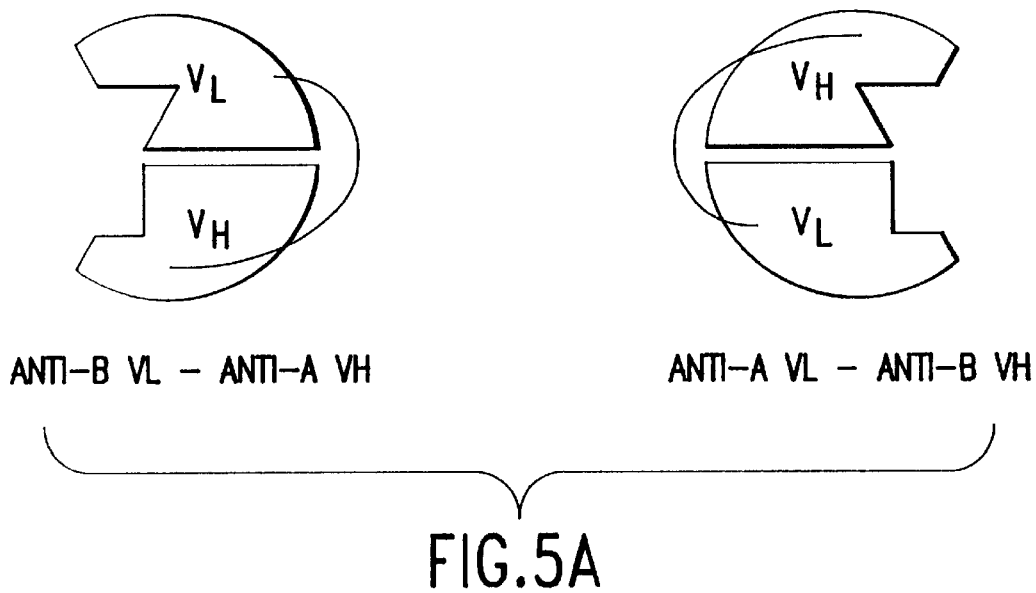
FIG. 5A depicts two single-chain protein molecules, the first having an anti-B $V_L$ and an anti-A $V_H$, and the second having an anti-A $V_L$ and an anti-B $V_H$. The figure shows the non-complementary nature of the $V_L$ and $V_H$ regions in each single-chain protein molecule.
Figure 5B:
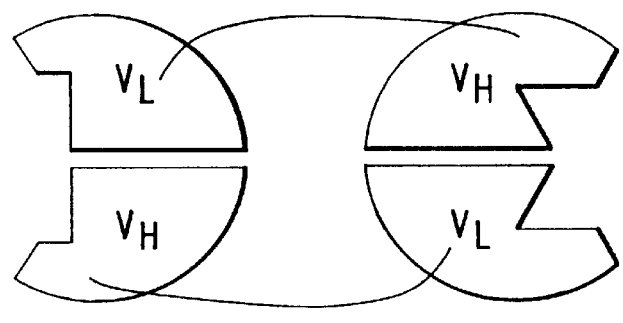
FIG. 5B shows a hypothetical bispecific heterodivalent antigen-binding protein formed by rearrangement of the two single-chain proteins of FIG. 5A.
Figure 5C:
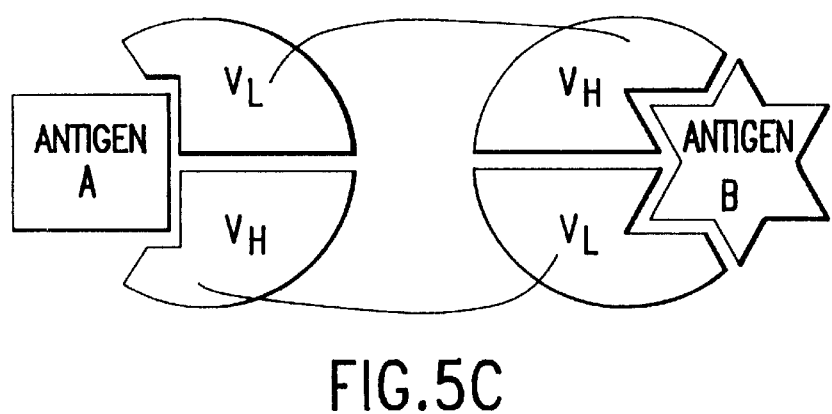
FIG. 5C depicts the hypothetical heterodivalent antigen-binding protein of FIG. 5B with different antigens A and B occupying their respective antigen-binding sites.
Figure 6A:
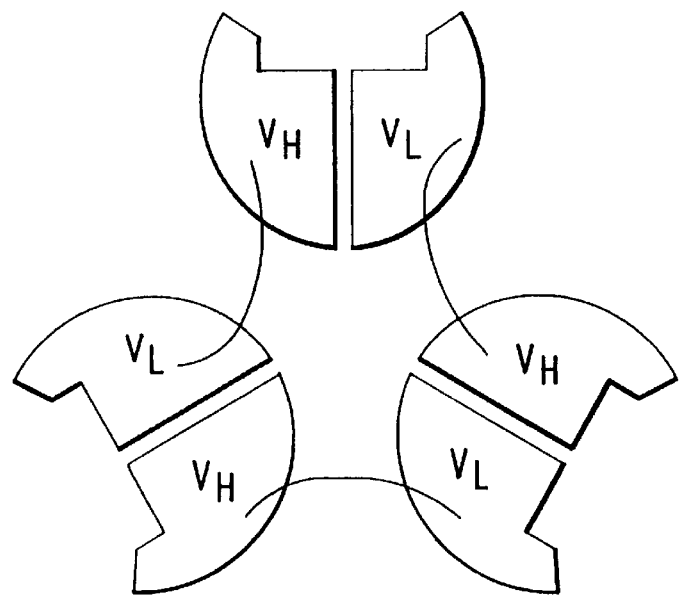
FIG. 6A is a schematic depiction of a hypothetical trivalent antigen-binding protein according to the Rearrangement model.
Figure 6B:
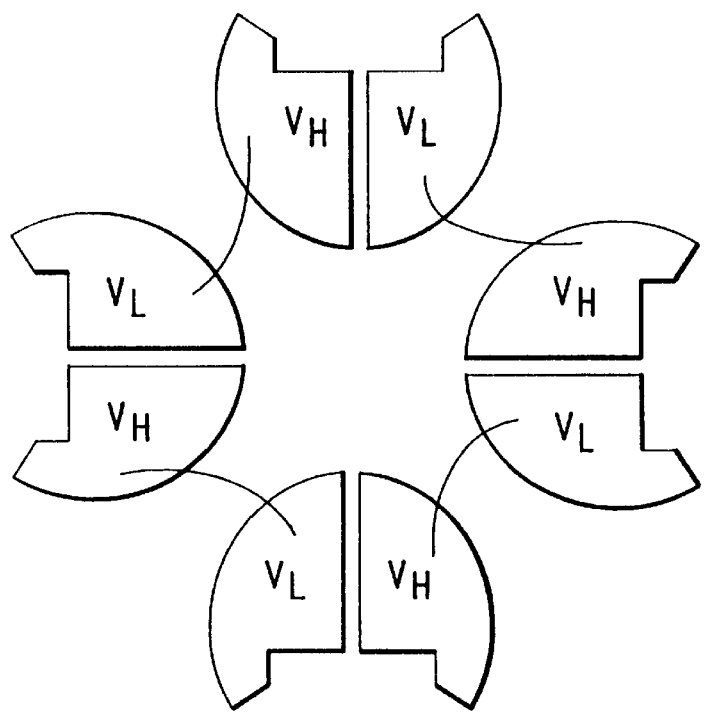
FIG. 6B is a schematic depiction of a hypothetical tetravalent antigen-binding protein according to the Rearrangement model.

FIGS. 5A–5C show the formation of heterobivalent antigen-binding proteins via the Rearrangement model. FIG. 5A shows a pair of single-chain proteins, each having a $V_L$ with complementarity determining regions (CDRs) that do not match those of the associated $V_H$. These single-chain proteins have reduced or no ability to bind antigen because of the mixed nature of their antigen-binding sites, and thus are made specifically to be assembled into multivalent proteins through this route. FIG. 5B shows the heterobivalent antigen-binding protein formed whereby the $V_H$ and $V_L$ regions of the parent proteins are shared between the separate halves of the heterobivalent protein. FIG. 5C shows the binding of two different antigen molecules to the resultant functional bispecific heterobivalent protein. The Rearrangement model also explains the generation of multivalent proteins of a higher order than bivalent, as it can be appreciated that more than a pair of single-chain proteins can be reassembled in this manner. These are depicted in FIGS. 6A and 6B.

One of the major utilities of the multivalent antigen-binding protein is in the heterobivalent form, in which one specificity is for one type of hapten or antigen, and the second specificity is for a second type of hapten or antigen. A multivalent molecule having two distinct binding specificities has many potential uses. For instance, one antigen binding site may be specific for a cell-surface epitope of a target cell, such as a tumor cell or other undesirable cell. The other antigen-binding site may be specific for a cell-surface epitope of an effector cell, such as the CD3 protein of a cytotoxic T-cell. In this way, the heterobivalent antigen-binding protein may guide a cytotoxic cell to a particular class of cells that are to be preferentially attacked.

Other uses of heterobivalent antigen-binding proteins are the specific targeting and destruction of blood clots by a bispecific molecule with specificity for tissue plasminogen activator (tPA) and fibrin; the specific targeting of pro-drug activating enzymes to tumor cells by a bispecific molecule with specificity for tumor cells and enzyme; and specific targeting of cytotoxic proteins to tumor cells by a bispecific molecule with specificity for tumor cells and a cytotoxic protein. This list is illustrative only, and any use for which a multivalent specificity is appropriate comes within the scope of this invention.

The invention also extends to uses for the multivalent antigen-binding proteins in purification and biosensors.

Affinity purification is made possible by affixing the multivalent antigen-binding protein to a support, with the antigen-binding sites exposed to and in contact with the ligand molecule to be separated, and thus purified. Biosensors generate a detectable signal upon binding of a specific antigen to an antigen-binding molecule, with subsequent processing of the signal. Multivalent antigen-binding proteins, when used as the antigen-binding molecule in biosensors, may change conformation upon binding, thus generating a signal that may be detected.

Essentially all of the uses for which monoclonal or polyclonal antibodies, or fragments thereof, have been envisioned by the prior art, can be addressed by the multivalent proteins of the present invention. These uses include detectably-labelled forms of the multivalent protein. Types of labels are well-known to those of ordinary skill in the art. They include radiolabelling, chemiluminescent labeling, fluorochromic labelling, and chromophoric labeling. Other uses include imaging the internal structure of an animal (including a human) by administering an effective amount of a labelled form of the multivalent protein and measuring detectable radiation associated with the animal. They also include improved immunoassays, including sandwich immunoassay, competitive immunoassay, and other immunoassays wherein the labelled antibody can be replaced by the multivalent antigen-binding protein of this invention.

A first preferred method of producing multivalent antigen-binding proteins involves separating the multivalent proteins from a production composition that comprises both multivalent and single-chain proteins, as represented in Example 1. The method comprises producing a composition of multivalent and single-chain proteins, separating the multivalent proteins from the single-chain proteins, and recovering the multivalent proteins.

A second preferred method of producing multivalent antigen-binding proteins comprises the steps of producing single-chain protein molecules, dissociating said single-chain molecules, reassociating the single-chain molecules such that a significant fraction of the resulting composition includes multivalent forms of the single-chain antigen-binding proteins, separating multivalent antigen-binding proteins from single-chain molecules, and recovering the multivalent proteins. This process is illustrated with more detail in Example 2. For the purposes of this method, the term "producing a composition comprising single-chain molecules" may indicate the actual production of these molecules. The term may also include procuring them from whatever commercial or institutional source makes them available. Use of the term "producing single-chain proteins" means production of single-chain proteins by any process, but preferably according to the process set forth in U.S. Pat. No. 4,946,778 (Ladner et al.). Briefly, that patent pertains to a single polypeptide chain antigen-binding molecule which has binding specificity and affinity substantially similar to the binding specificity and affinity of the aggregate light and heavy chain variable regions of an antibody, to genetic sequences coding therefore, and to recombinant DNA methods of producing such molecules, and uses for such molecules. The single-chain protein produced by the Ladner et al. methodology comprises two regions linked by a linker polypeptide. The two regions are termed the $V_H$ and $V_L$ regions, each region comprising one half of a functional antigen-binding site.

The term "dissociating said single-chain molecules" means to cause the physical separation of the two variable regions of the single-chain protein without causing denaturation of the variable regions.

"Dissociating agents" are defined herein to include all agents capable of dissociating the variable regions, as defined above. In the context of this invention, the term includes the well-known agents alcohol (including ethanol), guanidine hydrochloride (GuHCl), and urea. Others will be apparent to those of ordinary skill in the art, including detergents and similar agents capable of interrupting the interactions that maintain protein conformation. In the preferred embodiment, a combination of GuHCl and ethanol (EtOH) is used as the dissociating agent. A preferred range for ethanol and GuHCl is from 0 to 50% EtOH, vol/vol, 0 to 2.0 moles per liter (M) GuHCl. A more preferred range is from 10–30% EtOH and 0.5–1.0M GuHCl, and a most preferred range is 20% EtOH, 0.5M GuHCl. A preferred dissociation buffer contains 0.5M guanidine hydrochloride, 20% ethanol, 0.05M TRIS, and 0.01M $CaCl_2$, pH 8.0.

Use of the term "re-associating said single-chain molecules" is meant to describe the reassociation of the variable regions by contacting them with a buffer solution that allows reassociation. Such a buffer is preferably used in the present invention and is characterized as being composed of 0.04M MOPS, 0.10M calcium acetate, pH 7.5. Other buffers allowing the reassociation of the $V_L$ and $V_H$ regions are well within the expertise of one of ordinary skill in the art.

The separation of the multivalent protein from the single-chain molecules occurs by use of standard techniques known in the art, particularly including cation exchange or gel filtration chromatography.

Figure 7:
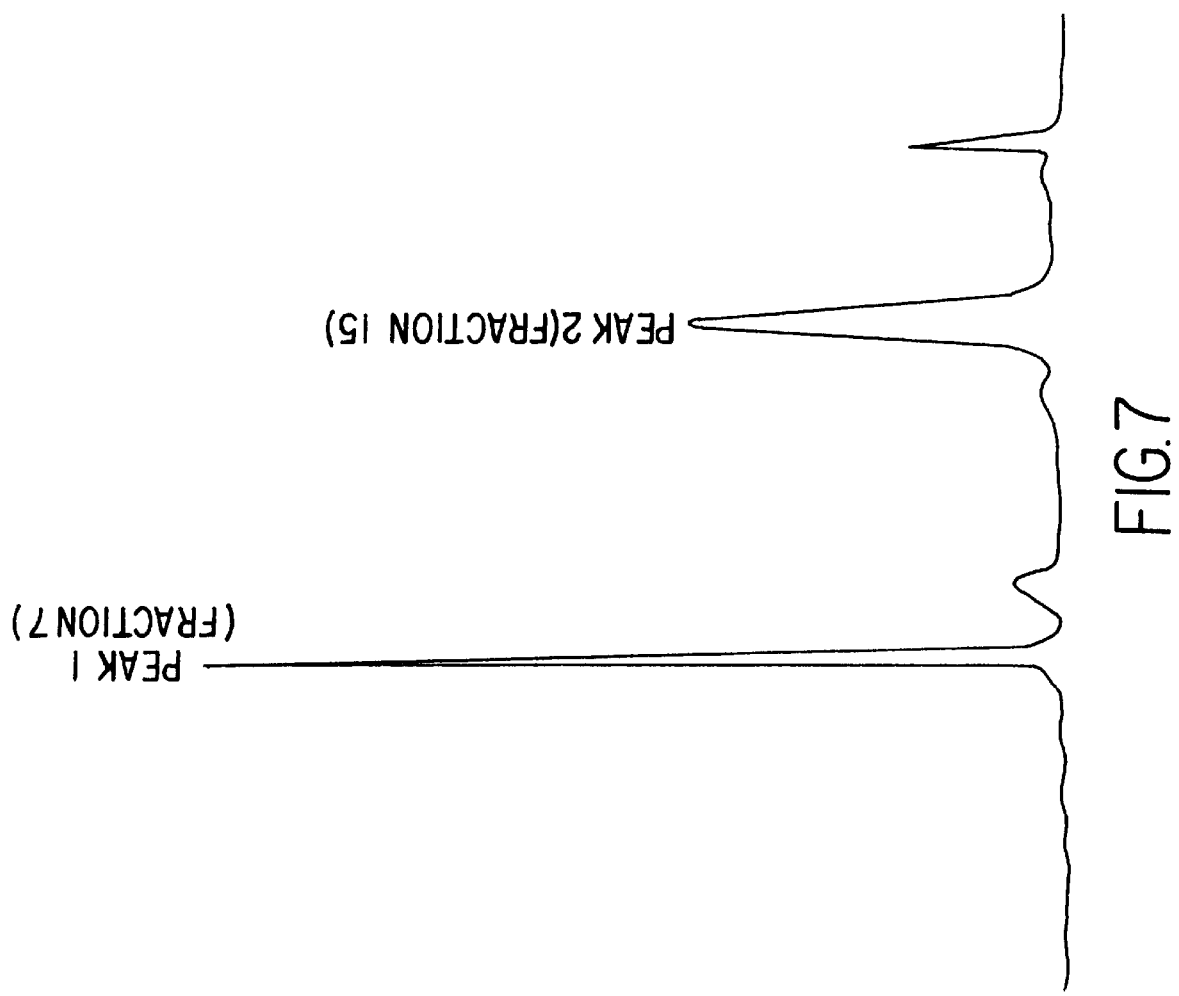
FIG. 7 is a chromatogram depicting the separation of CC49/212 antigen-binding protein monomer from dimer on a cation exchange high performance liquid chromatographic column. The column is a PolyCAT A aspartic acid column (Poly WC, Columbia, Md.). Monomer is shown as Peak 1, eluting at 27.32 min., and dimer is shown as Peak 2, eluting at 55.52 min.

Cation exchange chromatography is the general liquid chromatographic technique of ion-exchange chromatography utilizing anion columns well-known to those of ordinary skill in the art. In this invention, the cations exchanged are the single-chain and multivalent protein molecules. Since multivalent proteins will have some multiple of the net charge of the single-chain molecule, the multivalent proteins are retained more strongly and are thus separated from the single-chain molecules. The preferred cationic exchanger of the present invention is a polyaspartic acid column, as shown in FIG. 7. FIG. 7 depicts the separation of single-chain protein (Peak 1, 27.32 min.) from bivalent protein (Peak 2, 55.54 min.) Those of ordinary skill in the art will realize that the invention is not limited to any particular type of chromatography column, so long as it is capable of separating the two forms of protein molecules.

Figure 8:
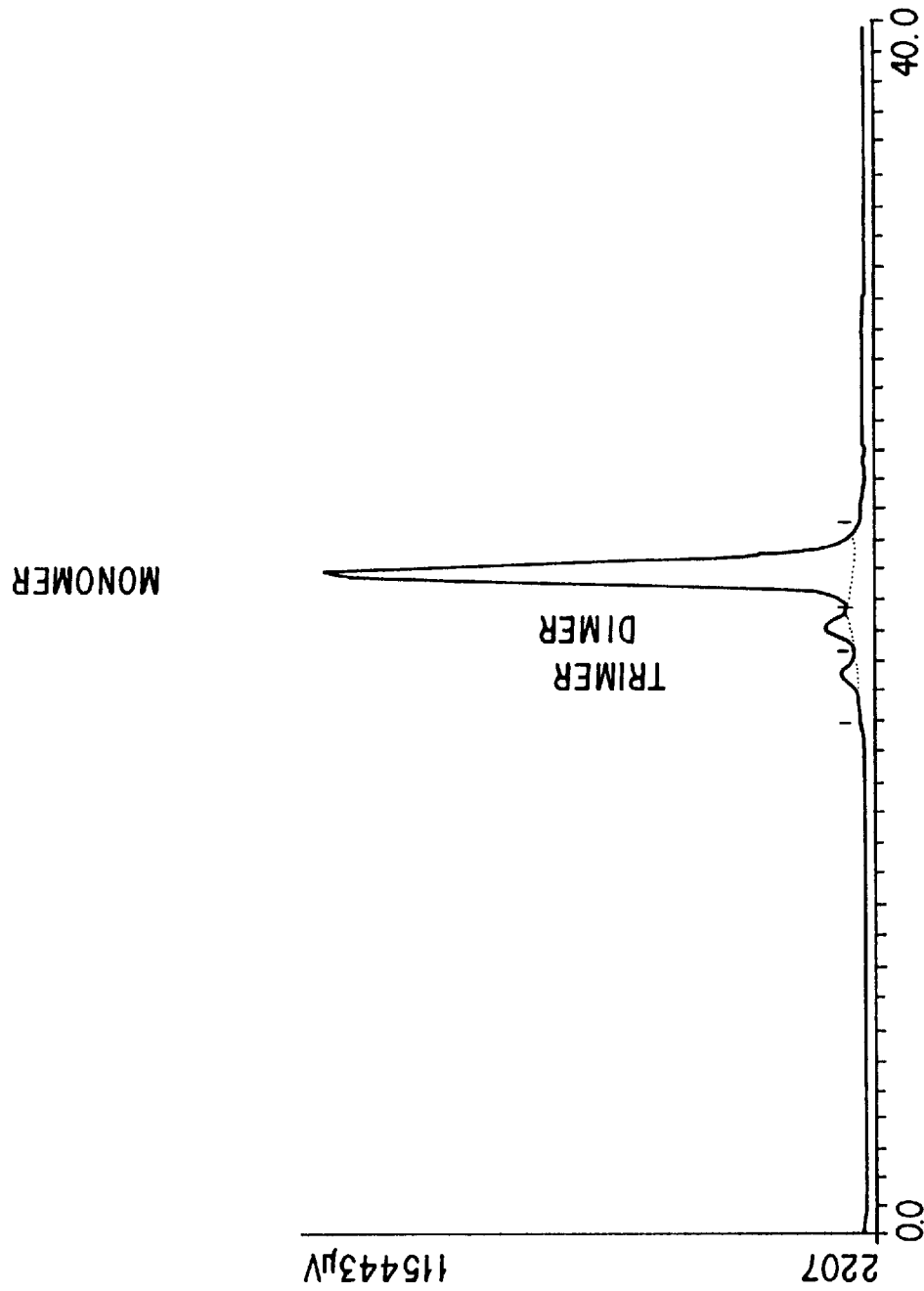
FIG. 8 is a chromatogram of the purified monomer from FIG. 7. Monomer elutes at 21.94 min., preceded by dimer (20.135 min.) and trimer (18.640 min.). Gel filtration column, Protein-Pak 300SW (Waters Associates, Milford, Mass.).

Gel filtration chromatography is the use of a gel-like material to separate proteins on the basis of their molecular weight. A "gel" is a matrix of water and a polymer, such as agarose or polymerized acrylamide. The present invention encompasses the use of gel filtration HPLC (high performance liquid chromatography), as will be appreciated by one of ordinary skill in the art. FIG. 8 is a chromatogram depicting the use of a Waters Associates' Protein-Pak 300 SW gel filtration column to separate monovalent single-chain protein from multivalent protein, including the monomer (21.940 min.), bivalent protein (20.135 min.), and trivalent protein (18.640 min.).

Recovering the multivalent antigen-binding proteins is accomplished by standard collection procedures well known in the chemical and biochemical arts. In the context of the present invention recovering the multivalent protein preferably comprises collection of eluate fractions containing the peak of interest from either the cation exchange column, or the gel filtration HPLC column. Manual and automated fraction collection are well-known to one of ordinary skill in the art. Subsequent processing may involve lyophilization of the eluate to produce a stable solid, or further purification.

A third preferred method of producing multivalent antigen-binding proteins is to start with purified single-chain proteins at a lower concentration, and then increase the concentration until some significant fraction of multivalent proteins is formed. The multivalent proteins are then separated and recovered. The concentrations conducive to formation of multivalent proteins in this manner are from about 0.5 milligram per milliliter (mg/ml) to the concentration at which precipitates begin to form.

The use of the term "substantially free" when used to describe a composition of multivalent and single-chain antigen-binding protein molecules means the lack of a significant peak corresponding to the single-chain molecule, when the composition is analyzed by cation exchange chromatography, as disclosed in Example 1 or by gel filtration chromatography as disclosed in Example 2.

By use of the term "aqueous composition" is meant any composition of single-chain molecules and multivalent proteins including a portion of water. In the same context, the phrase "an excess of multivalent antigen-binding protein over single-chain molecules" indicates that the composition comprises more than 50% of multivalent antigen-binding protein.

The use of the term "cross-linking" refers to chemical means by which one can produce multivalent antigen-binding proteins from monovalent single-chain protein molecules. For example, the incorporation of a cross-linkable sulfhydryl chemical group as a cysteine residue in the single-chain proteins allows cross-linking by mild reduction of the sulfhydryl group. Both monospecific and multispecific multivalent proteins can be produced from single-chain proteins by cross-linking the free cysteine groups from two or more single-chain proteins, causing a covalent chemical linkage to form between the individual proteins. Free cysteines have been engineered into the C-terminal portion of the 4-4-20/212 single-chain antigen-binding protein, as discussed in Example 5 and Example 8. These free cysteines may then be cross-linked to form multivalent antigen-binding proteins.

The invention also comprises single-chain proteins, comprising: (a) a first polypeptide comprising the binding portion of the variable region of an antibody light chain; (b) a second polypeptide comprising the binding portion of the variable region of an antibody light chain; and (c) a peptide linker linking said first and second polypeptides (a) and (b) into said single-chain protein. A similar single-chain protein comprising the heavy chain variable regions is also a part of this invention. Genetic sequences encoding these molecules are also included in the scope of this invention. Since these proteins are comprised of two similar variable regions, they do not necessarily have any antigen-binding capability.

The invention also includes a DNA sequence encoding a bispecific bivalent antigen-binding protein. Example 4 and Example 7 discusses in detail the sequences that appear in FIGS. 10A and 10B that allow one of ordinary skill to construct a heterobivalent antigen-binding molecule. FIG. 10A is an amino acid and nucleotide sequence listing of the single-chain protein comprising the 4-4-20 $V_L$ region connected through the 212 linker polypeptide to the CC49 $V_H$ region. FIG. 10B is a similar listing of the single-chain protein comprising the CC49 $V_L$ region connected through the 212 linker polypeptide to the 4-4-20 $V_H$ region. Subjecting a composition including these single-chain molecules to dissociating and subsequent re-associating conditions results in the production of a bivalent protein with two different binding specificities.

Synthesis of DNA sequences is well know in the art, and possible through at least two routes. First, it is well-known that DNA sequences may be synthesized through the use of automated DNA synthesizers de novo, once the primary sequence information is known. Alternatively, it is possible to obtain a DNA sequence coding for a multivalent single-chain antigen-binding protein by removing the stop codons from the end of a gene encoding a single-chain antigen-binding protein, and then inserting a linker and a gene encoding a second single-chain antigen-binding protein. Example 6 demonstrates the construction of a DNA sequence coding for a bivalent single-chain antigen-binding protein. Other methods of genetically constructing multivalent single-chain antigen-binding proteins come within the spirit and scope of the present invention.

Having now generally described this invention the same will better be understood by reference to certain specific examples which are included for purposes of illustration and are not intended to limit it unless otherwise specified.

EXAMPLE 1

Production of Multivalent Antigen-Binding Proteins During Purification

In the production of murecomlent antigen-binding proteins, the same recombinant E. coli production system that was used for prior single-chain antigen-binding protein production was used. See Bird, et al., Science 242:423 (1988). This production system produced between 2 and 20% of the total E. coli protein as antigen-binding protein. For protein recovery, the frozen cell paste from three 10-liter fermentations (600–900 g) was thawed overnight at 4° C. and gently resuspended at 4° C. in 50 mM Tris-HCl, 1.0 mM EDTA, 100 mM KCl, 0.1 mM PMSF, pH 8.0 (lysis buffer), using 10 liters of lysis buffer for every kilogram of wet cell paste. When thoroughly resuspended, the chilled mixture was passed three times through a Manton-Gaulin cell homogenizer to totally lyse the cells. Because the cell homogenizer raised the temperature of the cell lysate to 25°±5° C., the cell lysate was cooled to 5°±2° C. with a Lauda/Brinkman chilling coil after each pass. Complete lysis was verified by visual inspection under a microscope.

The cell lysate was centrifuged at 24,300 g for 30 min. at 6° C. using a Sorvall RC-5B centrifuge. The pellet containing the insoluble antigen-binding protein was retained, and the supernatant was discarded. The pellet was washed by gently scraping it from the centrifuge bottles and resuspending it in 5 liters of lysis buffer/kg of wet cell paste. The resulting 3.0- to 4.5-liter suspension was again centrifuged at 24,300 g for 30 min at 6° C., and the supernatant was discarded. This washing of the pellet removes soluble E. coli proteins and can be repeated as many as five times. At any time during this washing procedure the material can be stored as a frozen pellet at –20° C. A substantial time saving in the washing steps can be accomplished by utilizing a Pellicon tangential flow apparatus equipped with 0.22-$\mu$m microporous filters, in place of centrifugation.

The washed pellet was solubilized at 4° C. in freshly prepared 6M guanidine hydrochloride, 50 mM Tris-HCl, 10 mM $CaCl_2$, 50 mM KCl, pH 8.0 (dissociating buffer), using 9 ml/g of pellet. If necessary, a few quick pulses from a Heat Systems Ultrasonics tissue homogenizer can be used to complete the solubilization. The resulting suspension was centrifuged at 24,300 g for 45 min at 6° C. and the pellet was discarded. The optical density of the supernatant was determined at 280 nm and if the $OD_{280}$ was above 30, additional dissociating buffer was added to obtain an $OD_{280}$ of approximately 25.

The supernatant was slowly diluted into cold (4°–7° C.) refolding buffer (50 mM Tris-HCl, 10 mM CaCl$_2$, 50 mM KCl, pH 8.0) until a 1:10 dilution was reached (final volume 10–20 liters). Re-folding occurs over approximately eighteen hours under these conditions. The best results are obtained when the GuHCl extract is slowly added to the refolding buffer over a 2-h period, with gentle mixing. The solution was left undisturbed for at least a 20-h period, and 95% ethanol was added to this solution such that the final ethanol concentration was approximately 20%. This solution was left undisturbed until the flocculated material settled to the bottom, usually not less than sixty minutes. The solution was filtered through a 0.2 um Millipore Millipak 200. This filtration step may be optionally preceded by a centrifugation step. The filtrate was concentrated to 1 to 2 liters using an Amicon spiral cartridge with a 10,000 MWCO cartridge, again at 4° C.

The concentrated crude antigen-binding protein sample was dialyzed against Buffer A (60 mM MOPS, 0.5 mM Ca acetate, pH 6.0–6.4) until the conductivity was lowered to that of Buffer A. The sample was then loaded on a 21.5× 250-mm polyaspartic acid PolyCAT A column, manufactured by Poly LC of Columbia, Md. If more than 60 mg of protein is loaded on this column, the resolution begins to deteriorate; thus, the concentrated crude sample often must be divided into several PolyCAT A runs. Most antigen-binding proteins have an extinction coefficient of about 2.0 ml mg$^{-1}$ cm$^{-1}$ at 280 nm and this can be used to determine protein concentration. The antigen-binding protein sample was eluted from the PolyCAT A column with a 50-min linear gradient from Buffer A to Buffer B (see Table 1). Most of the single-chain proteins elute between 20 and 26 minutes when this gradient is used. This corresponds to an eluting solvent composition of approximately 70% Buffer A and 30% Buffer B. Most of the bivalent antigen-binding proteins elute later than 45 minutes, which correspond to over 90% Buffer B.

FIG. 7 is a chromatogram depicting the separation of single-chain protein from bivalent CC49/212 protein, using the cation-exchange method just described. Peak 1, 27.32 minutes, represents the monomeric single-chain fraction. Peak 2, 55.52 minutes, represents the bivalent protein fraction.

Figure 9:
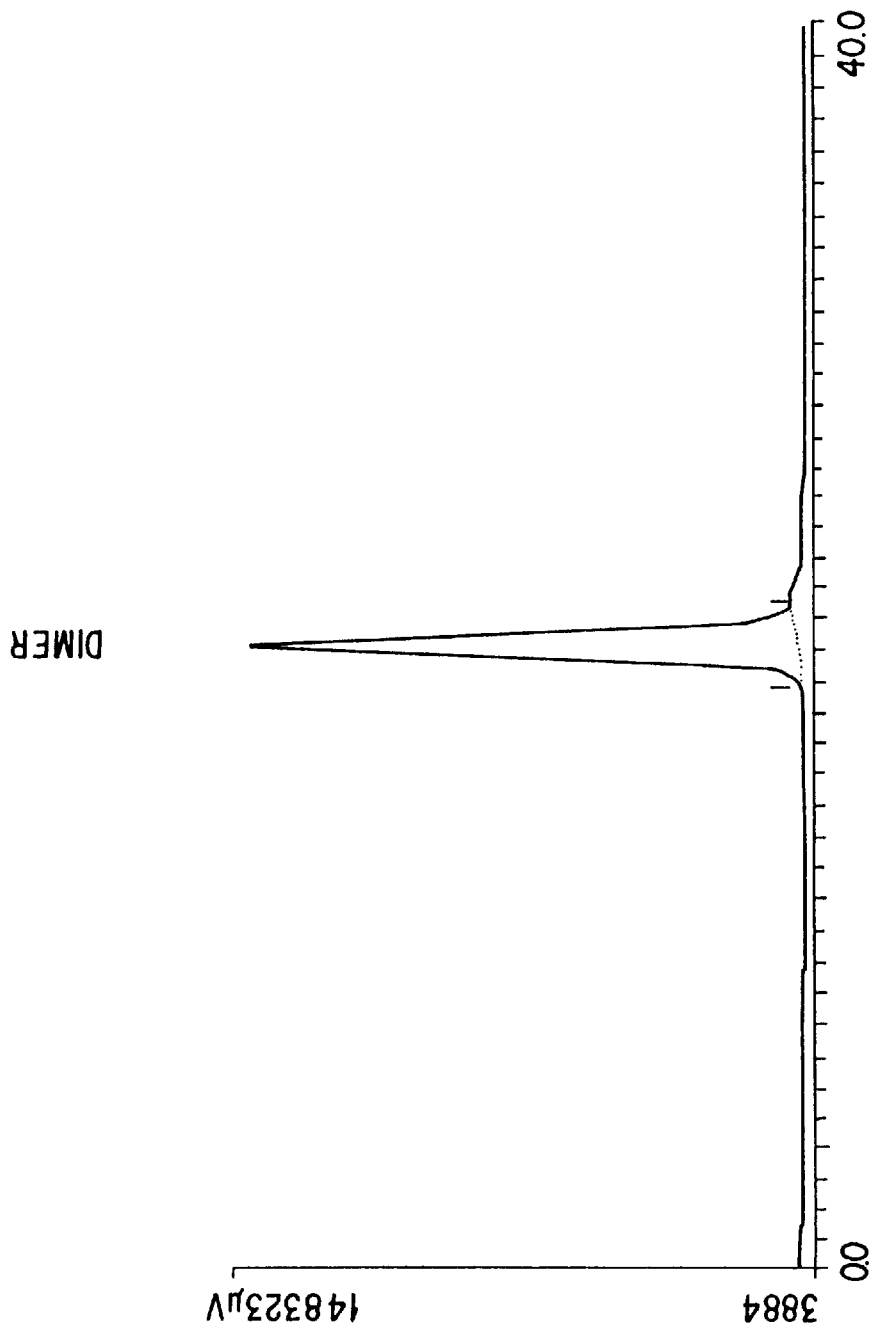
FIG. 9 is a similar chromatogram of purified dimer (20.14 min.) from FIG. 7, run on the gel filtration HPLC column of FIG. 8.

FIG. 8 is a chromatogram of the purified monomeric single-chain antigen-binding protein CC49/212 (Fraction 7 from FIG. 7) run on a Waters Protein-Pak 300SW gel filtration column. Monomer, with minor contaminates of dimer and trimer, is shown. FIG. 9 is a chromatogram of the purified bivalent antigen-binding protein CC49/212 (Fraction 15 from FIG. 7) run on the same Waters Protein-Pak 300SW gel filtration column as used in FIG. 8.

TABLE 1

| PolyCAT A Cation-Exchange HPLC Gradients | | | | |
|---|---|---|---|---|
| Time | Flow | Buffers[b] | | |
| (min)[a] | (ml/min) | A | B | C |
| Initial | 15.0 | 100 | 0 | 0 |
| 50.0 | 15.0 | 0 | 100 | 0 |
| 55.0 | 15.0 | 0 | 100 | 0 |
| 60.0 | 15.0 | 0 | 0 | 100 |
| 63.0 | 15.0 | 0 | 0 | 100 |
| 64.0 | 15.0 | 100 | 0 | 0 |
| 67.0 | 15.0 | 100 | 0 | 0 |

[a]Linear gradients are run between each time point.
[b]Buffer A, 60 mM MOPS, 0.5 mM Ca acetate, pH 6.0–6.4;

TABLE 1-continued

| PolyCAT A Cation-Exchange HPLC Gradients | | | | |
|---|---|---|---|---|
| Time | Flow | Buffers[b] | | |
| (min)[a] | (ml/min) | A | B | C |

Buffer B, 60 mM MOPS, 20 mM Ca acetate, pH 7.5–8.0;
Buffer C, 40 mM MOPS, 100 mM CaCl$_2$, pH 7.5.

This purification procedure yielded multivalent antigen-binding proteins that are more than 95% pure as examined by SDS-PAGE and size exclusion HPLC. Modifications of the above procedure may be dictated by the isoelectric point of the particular multivalent antigen-binding protein being purified. Of the monomeric single-chain proteins that have been purified to date, all have had an isoelectric point (pI) between 8.0 and 9.5. However, it is possible that a multivalent antigen-binding protein may be produced with a pI of less than 7.0. In that case, an anion exchange column may be required for purification.

The CC49 monoclonal antibody was developed by Dr. Jeffrey Schlom's group, Laboratory of Tumor Immunology and Biology, National Cancer Institute. It binds specifically to the pan-carcinoma tumor antigen TAG-72. See Muraro, R. et al., *Cancer Research* 48:4588–4596 (1988).

Figure 18:
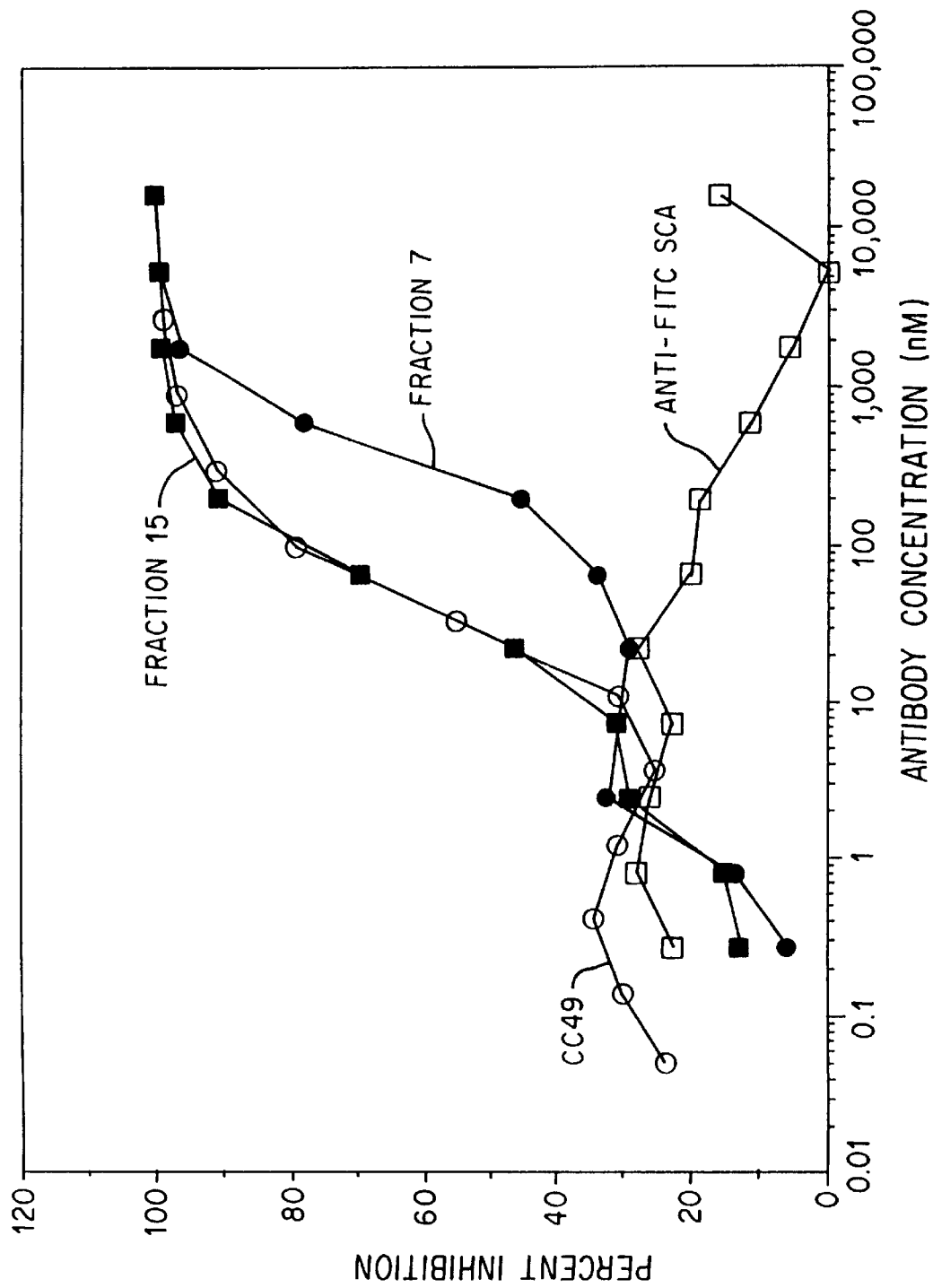
FIG. 18 is a graphical representation of four competition radioimmunoassays (RIA) in which unlabeled CC49 IgG (open circles) CC49/212 single-chain antigen-binding protein (closed circles) and CC49/212 divalent antigen-binding protein (closed squares) and anti-fluorescein 4-4-20/212 single-chain antigen-binding protein (open squares) competed against a CC49 IgG radiolabeled with $^{125}$I for binding to the TAG-72 antigen on a human breast carcinoma extract.

To determine the binding properties of the bivalent and monomeric CC49/212 antigen-binding proteins, a competition radioimmunoassay (RIA) was set up in which a CC49 IgG (with two antigen binding sites) radiolabeled with $^{125}$I was competed against unlabeled CC49 IgG, or monovalent (fraction 7 in FIG. 7) or bivalent (fraction 15 in FIG. 7) CC49/212 antigen-binding protein for binding to the TAG-72 antigen on a human breast carcinoma extract. (See FIG. 18). This competition RIA showed that the bivalent antigen-binding protein competed equally well for the antigen as did IgG, whereas the monovalent single-chain antigen-binding protein needed a ten-fold higher protein concentration to displace the IgG. Thus, the monovalent antigen-binding protein competes with about a ten-fold lower affinity for the antigen than does the bivalent IgG or bivalent antigen-binding protein. FIG. 18 also shows the result of the competition RIA of a non-TAG-72 specific single-chain antigen-binding protein, the antifluorescein 4-4-20/212, which does not compete for binding.

EXAMPLE 2

Process of Making Multivalent Antigen-Binding Proteins Using Dissociating Agents A. Process Using Guanidine HCl and Ethanol Multivalent antigen-binding proteins were produced from purified single-chain proteins in the following way. First the purified single-chain protein at a concentration of 0.25–4 mg/ml was dialyzed against 0.5 moles/liter (M) guanidine hydrochloride (GuHCl), 20% ethanol (EtOH), in 0.05M TRIS, 0.05M KCl, 0.01M CaCl$_2$ buffer pH 8.0. This combination of dissociating agents is thought to disrupt the $V_L/V_H$ interface, allowing the $V_H$ of a first single-chain molecule to come into contact with a $V_L$ from a second single-chain molecule. Other dissociating agents such as urea, and alcohols such as isopropanol or methanol should be substitutable for GuHCl and EtOH. Following the initial dialysis, the protein was dialyzed against the load buffer for the final HPLC purification step. Two separate purification protocols, cation exchange and gel filtration chromatography, can be used to separate the single-chain protein monomer from the multivalent antigen-binding proteins. In the first method, monomeric and multivalent antigen-binding proteins were separated by using cation exchange HPLC chromography, using a polyaspartate column (PolyCAT A). This was a similar procedure to that used in the final purification of the antigen-binding proteins as described in Example 1. The load buffer was 0.06M MOPS, 0.001M Calcium Acetate pH 6.4. In the second method, the monomeric and multivalent antigen-binding proteins were separated by gel filtration HPLC chromatography using as a load buffer 0.04M MOPS, 0.10M Calcium Acetate pH 7.5. Gel filtration chromatography separates proteins based on their molecular size.

Figure 11:
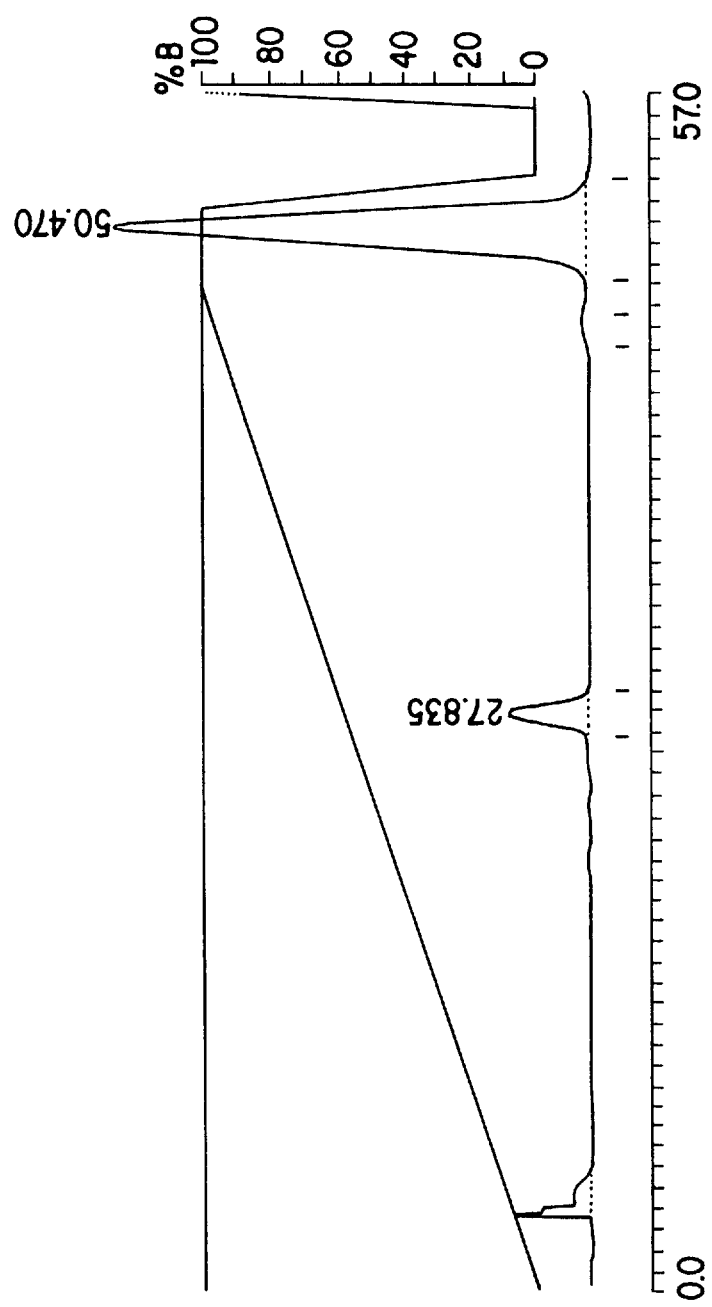
FIG. 11 is a chromatogram depicting the separation of the monomer (27.83 min.) and dimer (50.47 min.) forms of the CC49/212 antigen-binding protein by cation exchange, on a PolyCAT A cation exchange column (Poly LC, Columbia, Md.).

Once the antigen-binding protein sample was loaded on the cation exchange HPLC column, a linear gradient was run between the load buffer (0.04 to 0.06M MOPS, 0.000 to 0.001M calcium acetate, 0 to 10% glycerol pH 6.0–6.4) and a second buffer (0.04 to 0.06M MOPS, 0.01 to 0.02M calcium acetate, 0 to 10% glycerol pH 7.5). It was important to have extensively dialyze the antigen-binding protein sample before loading it on the column. Normally, the conductivity of the sample is monitored against the dialysis buffer. Dialysis is continued until the conductivity drops below 600 µS. FIG. 11 shows the separation of the monomeric (27.83 min.) and bivalent (50.47 min.) forms of the CC49/212 antigen-binding protein by cation exchange. The chromatographic conditions for this separation were as follows: PolyCAT A column, 200×4.6 mm, operated at 0.62 ml/min.; load buffer and second buffer as in Example 1; gradient program from 100 percent load buffer A to 0 percent load buffer A over 48 mins; sample was CC49/212, 1.66 mg/ml; injection volume 0.2 ml. Fractions were collected from the two peaks from a similar chromatogram and identified as monomeric and bivalent proteins using gel filtration HPLC chromatography as described below.

Figure 12:
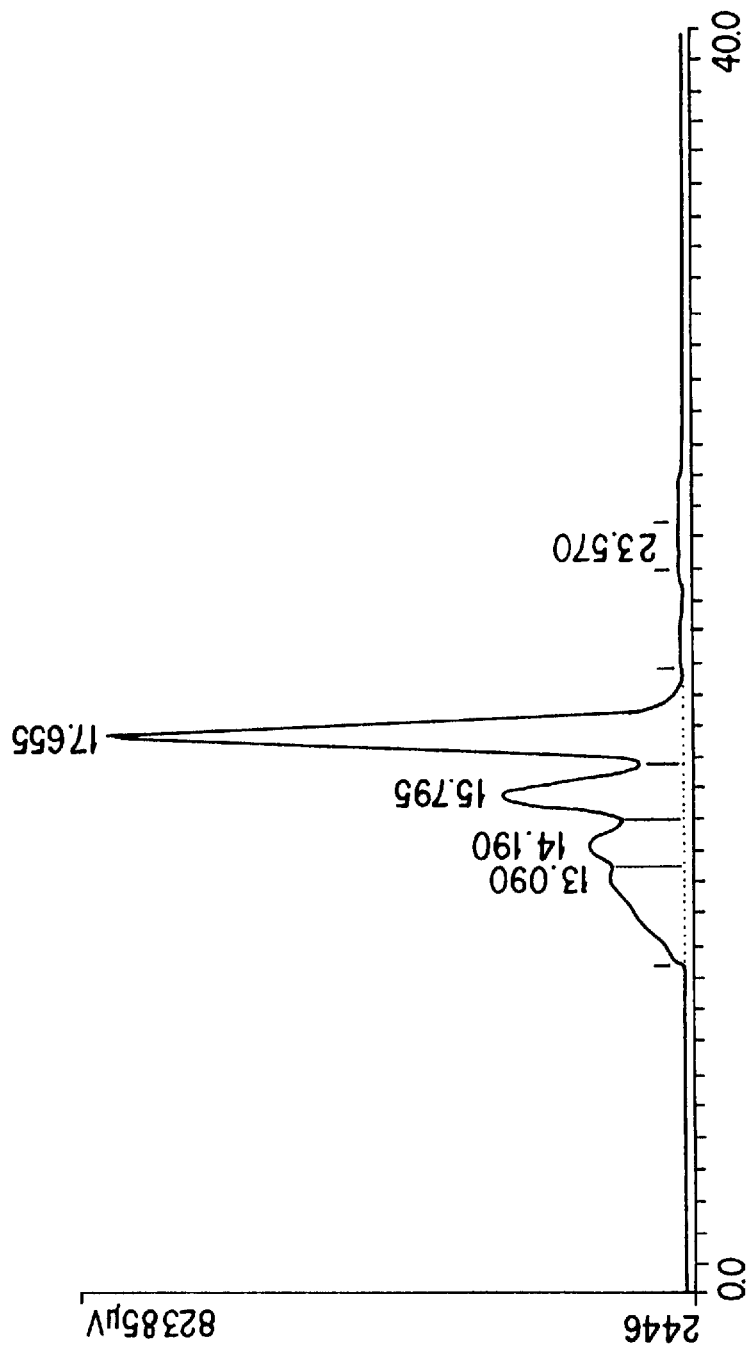
FIG. 12 shows the separation of monomer (17.65 min.), dimer (15.79 min.), trimer (14.19 min.), and higher oligomers (shoulder at about 13.09 min.) of the B6.2/212 antigen-binding protein. This separation depicts the results of a 24-hour treatment of a 1.0 mg/ml B6.2/212 single-chain antigen-binding protein sample. A TSK G2000SW gel filtration HPLC column was used, Toyo Soda, Tokyo, Japan.

Gel filtration HPLC chromatography (TSK G2000SW column from Toyo Soda, Tokyo, Japan) was used to identify and separate monomeric single-chain and multivalent antigen-binding proteins. This procedure has been described by Fukano, et al., *J. Chromatography* 166:47 (1978). Multimerization (creation of multivalent protein from monomeric single-chain protein) was by treatment with 0.5M GuHCl and 20% EtOH for the times indicated in Table 2A followed by dialysis into the chromatography buffer. FIG. 12 shows the separation of monomeric (17.65 min.), bivalent (15.79 min.), trivalent (14.19 min.), and higher oligomers (shoulder at about 13.09 min.) of the B6.2/212 antigen-binding protein. The B6.2/212 single-chain antigen-binding protein is described in Colcher, D., et al., *J. Nat. Cancer Inst.* 82:1191–1197 (1990)). This separation depicts the results of a 24-hour multimerization treatment of a 1.0 mg/ml B6.2/212 antigen-binding protein sample. The HPLC buffer used was 0.04M MOPS, 0.10M calcium acetate, 0.04% sodium azide, pH 7.5.

Figure 13:
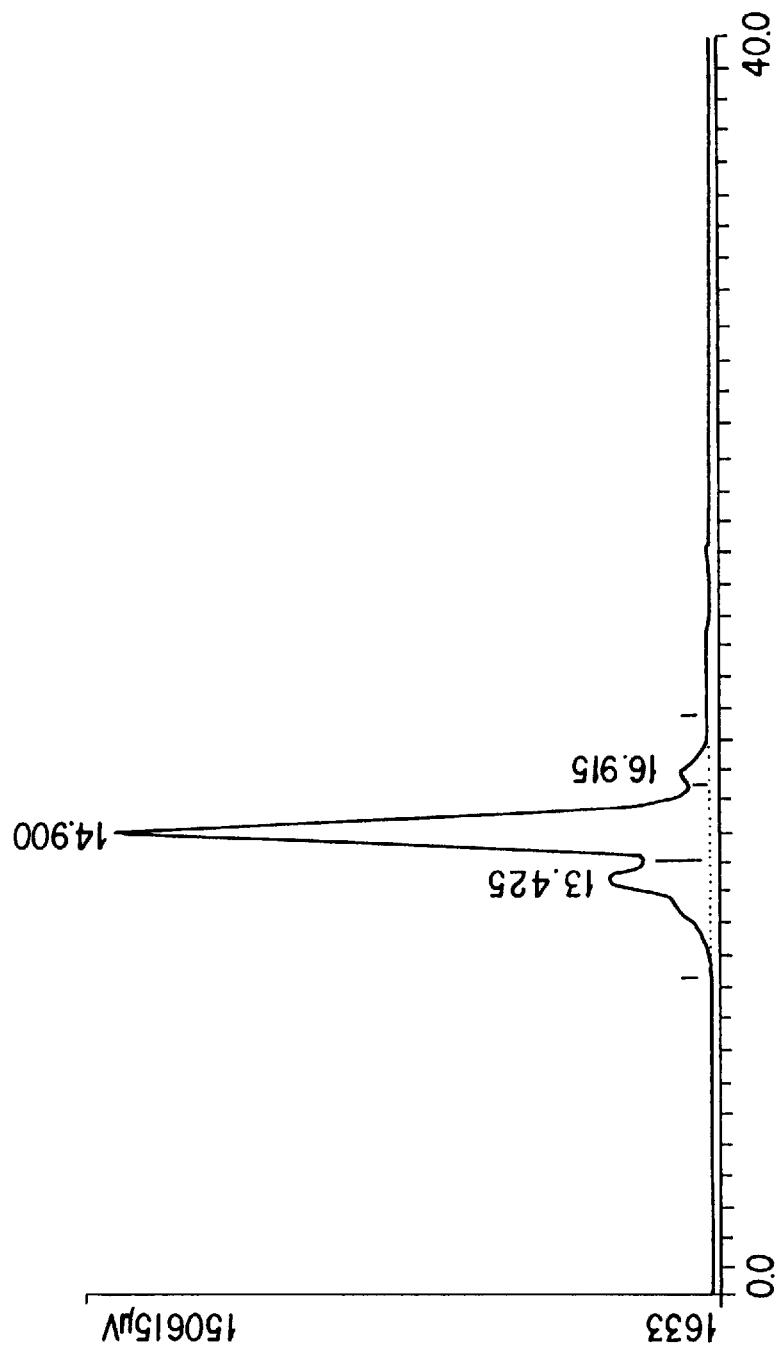
FIG. 13 shows the results of a 24-hour treatment of a 4.0 mg/ml CC49/212 antigen-binding protein sample, generating monomer, dimer, and trimer at 16.91, 14.9, and 13.42 min., respectively. The same TSK gel filtration column was used as in FIG. 12.

FIG. 13 shows the results of a 24-hour treatment of a 4.0 mg/ml CC49/212 antigen-binding protein sample, generating monomeric, bivalent and trivalent proteins at 16.91, 14.9, and 13.42 min., respectively. The HPLC buffer was 40 mM MOPS, 100 mM calcium acetate, pH 7.35. Multimerization treatment was for the times indicated in Table 2.

The results of Example 2A are shown in Table 2A. Table 2A shows the percentage of bivalent and other multivalent forms before and after treatment with 20% ethanol and 0.5M GuHCl. Unless otherwise indicated, percentages were determined using a automatic data integration software package.

TABLE 2A

Summary of the generation of bivalent and higher multivalent forms of B6.2/212 and CC49/212 proteins using guanidine hydrochloride and ethanol

| protein | Time (hours) | Concentration (mg/ml) | % monomer | dimer | trimer | multimers |
|---|---|---|---|---|---|---|
| CC49/212 | 0 | 0.25 | 86.7 | 11.6 | 1.7 | 0.0 |
|  | 0 | 1.0[2] | 84.0 | 10.6 | 5.5 | 0.0 |
|  | 0 | 4.0 | 70.0 | 17.1 | 12.9[1] | 0.0 |
|  | 2 | 0.25[2] | 62.9 | 33.2 | 4.2 | 0.0 |
|  | 2 | 1.0 | 24.2 | 70.6 | 5.1 | 0.0 |
|  | 2 | 4.0 | 9.3 | 81.3 | 9.5 | 0.0 |
|  | 26 | 0.25 | 16.0 | 77.6 | 6.4 | 0.0 |
|  | 26 | 1.0 | 9.2 | 82.8 | 7.9 | 0.0 |
|  | 26 | 4.0 | 3.7 | 78.2 | 18.1 | 0.0 |
| B6.2/212 | 0 | 0.25 | 100.0 | 0.0 | 0.0 | 0.0 |
|  | 0 | 1.0 | 100.0 | 0.0 | 0.0 | 0.0 |
|  | 0 | 4.0 | 100.0 | 0.0 | 0.0 | 0.0 |
|  | 2 | 0.25[2] | 98.1 | 1.9 | 0.0 | 0.0 |
|  | 2 | 1.0 | 100.0 | 0.0 | 0.0 | 0.0 |
|  | 2 | 4.0 | 90.0 | 5.5 | 1.0 | 0.0 |
|  | 24 | 0.25 | 45.6 | 37.5 | 10.2 | 6.7 |
|  | 24 | 1.0 | 50.8 | 21.4 | 12.3 | 15.0 |
|  | 24 | 4.0 | 5.9 | 37.2 | 25.7 | 29.9 |

[1]Based on cut out peaks that were weighted.
[2]Average of two experiments.

B. Process Using Urea and Ethanol

Multivalent antigen-binding proteins were produced from purified single-chain the following way. First the purified single-chain protein at a concentration of 0.25–1 mg/ml was dialyzed against 2M urea, 20% ethanol (EtOH), and 50 mM Tris buffer pH 8.0, for the times indicated in Table 2B. This combination of dissociating agents is thought to disrupt the $V_L/V_H$ interface, allowing the $V_H$ of a first single-chain molecule to come into contact with a $V_L$ from a second single-chain molecule. Other dissociating agent such as isoproanol or methanol should be substitutable for EtOH. Following the initial dialysis, the protein was dialyzed against the load buffer for the final HPLC purification step.

Gel filtration HPLC chromatography (TSK G2000SW column from Toyo Soda, Tokyo, Japan) was used to identify and separate monomeric single-chain and multivalent antigen-binding proteins. This procedure has been described by Fukano, et al., *J. Chromatography* 166:47 (1978).

The results of Example 2B are shown in Table 2B. Table 2B shows the percentage of bivalent and other multivalent forms before and after treatment with 20% ethanol and urea. Percentages were determined using an automatic data integration software package.

TABLE 2B

Summary of the generation of bivalent and higher multivalent forms of B6.2/212 and CC49/212 proteins using urea and ethanol

| protein | Time (hours) | Concentration (mg/ml) | % monomer | dimer | trimer | multimers |
|---|---|---|---|---|---|---|
| B6.2 | 0 | 0.25 | 44.1 | 37.6 | 15.9 | 2.4 |
|  | 0 | 1.0 | 37.7 | 33.7 | 19.4 | 9.4 |
|  | 3 | 0.25 | 22.2 | 66.5 | 11.3 | 0.0 |
|  | 3 | 1.0 | 13.7 | 69.9 | 16.4 | 0.0 |

EXAMPLE 3

Determination of Binding Constants

Three anti-fluorescein single-chain antigen-binding proteins have been constructed based on the anti-fluorescein monoclonal antibody 4-4-20. The three 4-4-20 single-chain antigen-binding proteins differ in the polypeptide linker connecting the $V_H$ and $V_L$ regions of the protein. The three linkers used were 202', 212 and 216 (see Table 3). Bivalent and higher forms of the 4-4-20 antigen-binding protein were produced by concentrating the purified monomeric single-chain antigen-binding protein in the cation exchange load buffer (0.06M MOPS, 0.001M calcium acetate pH 6.4) to 5 mg/ml. The bivalent and monomeric forms of the 4-4-20 antigen-binding proteins were separated by cation exchange HPLC (polyaspartate column) using a 50 min. linear gradient between the load buffer (0.06M MOPS, 0.001M calcium acetate pH 6.4) and a second buffer (0.06M MOPS, 0.02M calcium acetate pH 7.5). Two 0.02 ml samples were separated, and fractions of the bivalent and monomeric protein peaks were collected on each run. The amount of protein contained in each fraction was determined from the absorbance at 278 nm from the first separation. Before collecting the fractions from the second separation run, each fraction tube had a sufficient quantity of $1.03 \times 10^{-5}$M fluorescein added to it, such that after the fractions were collected a 1-to-1 molar ratio of protein-to-fluorescein existed. Addition of fluorescein stabilized the bivalent form of the 4-4-20 antigen-binding proteins. These samples were kept at 2° C. (on ice).

The fluorescein dissociation rates were determined for each of these samples following the procedures described by Herron, J. N., in *Fluorescence Hapten: An Immunological Probe*, E. W. Voss, Ed., CRC Press, Boca Raton, Fla. (1984). A sample was first diluted with 20 mM HEPES buffer pH 8.0 to $5.0 \times 10^{-8}$M 4-4-20 antigen-binding protein. 560 µl of the $5.0 \times 10^{-8}$M 4-4-20 antigen-binding protein sample was added to a cuvette in a fluorescence spectrophotometer equilibrated at 2° C. and the fluorescence was read. 140 µl of $1.02 \times 10^{-5}$M fluoresceinamine was added to the cuvette, and the fluorescence was read every 1 minute for up to 25 minutes (see Table 4).

The binding constants ($K_a$) for the 4-4-20 single-chain antigen-binding protein monomers diluted in 20 mM HEPES buffer pH 8.0 in the absence of fluorescein were also determined (see Table 4).

The three polypeptide linkers in these experiments differ in length. The 202', 212 and 216 linkers are 12, 14 and 18 residues long, respectively. These experiments show that there are two effects of linker length on the 4-4-20 antigen-binding proteins: first, the shorter the linker length the higher the fraction of bivalent protein formed; second, the fluorescein dissociation rates of the monomeric single-chain antigen-binding proteins are effected more by the linker length than are the dissociation rates of the bivalent antigen-binding proteins. With the shorter linkers 202' and 212, the bivalent antigen-binding proteins have slower dissociation rates than the monomers. Thus, the linkers providing optimum production and binding affinities for monomeric and bivalent antigen-binding proteins may be different. Longer linkers may be more suitable for monomeric single-chain antigen-binding proteins, and shorter linkers may be more suitable for multivalent antigen-binding proteins.

TABLE 3

Linker Designs

| $V_L$ | Linker | $V_H$ | Linker Name | Reference |
|---|---|---|---|---|
| -KLEIE | GKSSGSGSESKS[1] | TQKLD- | 202' | Bird et al. |
| -KLEIK | GSTSGSGKSSEGKG[2] | EVKLD- | 212 | Bedzyk et al. |
| -KLEIK | GSTSGSGKSSEGSGSTKG[3] | EVKLD- | 216 | This application |
| -KLVLK | GSTSGKPSEGKG[4] | EVKLD- | 217 | This application |

(1) SEQ ID NO. 1
(2) SEQ ID NO. 2
(3) SEQ ID NO. 3
(4) SEQ ID NO. 4

TABLE 4

Effects of Linkers on the SCA Protein Monomers and Dimers

| | Linker | | |
|---|---|---|---|
| | 202' | 212 | 216 |
| Monomer | | | |
| Fraction | 0.47 | 0.66 | 0.90 |
| Ka | $0.5 \times 10^9$ M$^{-1}$ | $1.0 \times 10^9$ M$^{-1}$ | $1.3 \times 10^9$ M$^{-1}$ |
| Dissociation rate | $8.2 \times 10^{-3}$ S$^{-1}$ | $4.9 \times 10^{-3}$ S$^{-1}$ | $3.3 \times 10^{-3}$ S$^{-1}$ |
| Dimer | | | |
| Fraction | 0.53 | 0.34 | 0.10 |
| Dissocation rate | $4.6 \times 10^{-3}$ S$^{-1}$ | $3.5 \times 10^{-3}$ S$^{-1}$ | $3.5 \times 10^{-3}$ S$^{-1}$ |
| Monomer/Dimer | | | |
| Dissociation rate ratio | 1.8 | 1.4 | 0.9 |

EXAMPLE 4

Genetic Construction of a Mixed-Fragment Bivalent Antigen-Binding Protein

The genetic constructions for one particular heterobivalent antigen-binding protein according to the Rearrangement model are shown in FIGS. 10A and 10B. FIG. 10A is an amino acid and nucleotide sequence listing of the 4-4-20 $V_L$/212/CC49 $V_H$ construct, coding for a single-chain protein with a 4-4-20 $V_L$, linked via a 212 polypeptide linker to a CC49 $V_H$. FIG. 10B is a similar listing showing the CC49 $V_L$/212/4-4-20 $V_H$ construct, coding for a single-chain protein with a CC49 $V_L$, linked via a 212 linker to a 4-4-20 $V_H$. These single-chain proteins may recombine according to the Rearrangement model to generate a heterobivalent protein comprising a CC49 antigen-binding site linked to a 4-4-20 antigen-binding site, as shown in FIG. 5B.

"4-4-20 $V_L$" means the variable region of the light chain of the 4-4-20 mouse monoclonal antibody (Bird, R. E. et al., *Science* 242:423 (1988)). The number "212" refers to a specific 14-residue polypeptide linker that links the 4-4-20 $V_L$ and the CC49 $V_H$. See Bedzyk, W. D. et al., *J. Biol.*

Chem. 265:18615–18620 (1990). "CC49 V$_H$" is the variable region of the heavy chain of the CC49 antibody, which binds to the TAG-72 antigen. The CC49 antibody was developed at The National Institutes of Health by Schlom, et al. Generation and Characterization of B72.3 Second Generation Monoclonal Antibodies Reactive With The Tumor-associated Glycoprotein 72 Antigen, Cancer Research 48:4588–4596 (1988).

Insertion of the sequences shown in FIGS. 10A and 10B, by standard recombinant DNA methodology, into a suitable plasmid vector will enable one of ordinary skill in the art to transform a suitable host for subsequent expression of the single-chain proteins. See Maniatis et al., *Molecular Cloning, A Laboratory Manual*, p. 104, Cold Spring Harbor Laboratory (1982), for general recombinant techniques for accomplishing the aforesaid goals; see also U.S. Pat. No. 4,946,778 (Ladner et al.) for a complete description of methods of producing single-chain protein molecules by recombinant DNA technology.

To produce multivalent antigen-binding proteins from the two single-chain proteins, 4-4-20V$_L$/212/CC49V$_H$ and CC49V$_L$/212/4-4-20V$_H$, the two single-chain proteins are dialyzed into 0.5M GuHCl/20% EtOH being combined in a single solution either before or after dialysis. The multivalent proteins are then produced and separated as described in Example 2.

EXAMPLE 5

Figure 14:
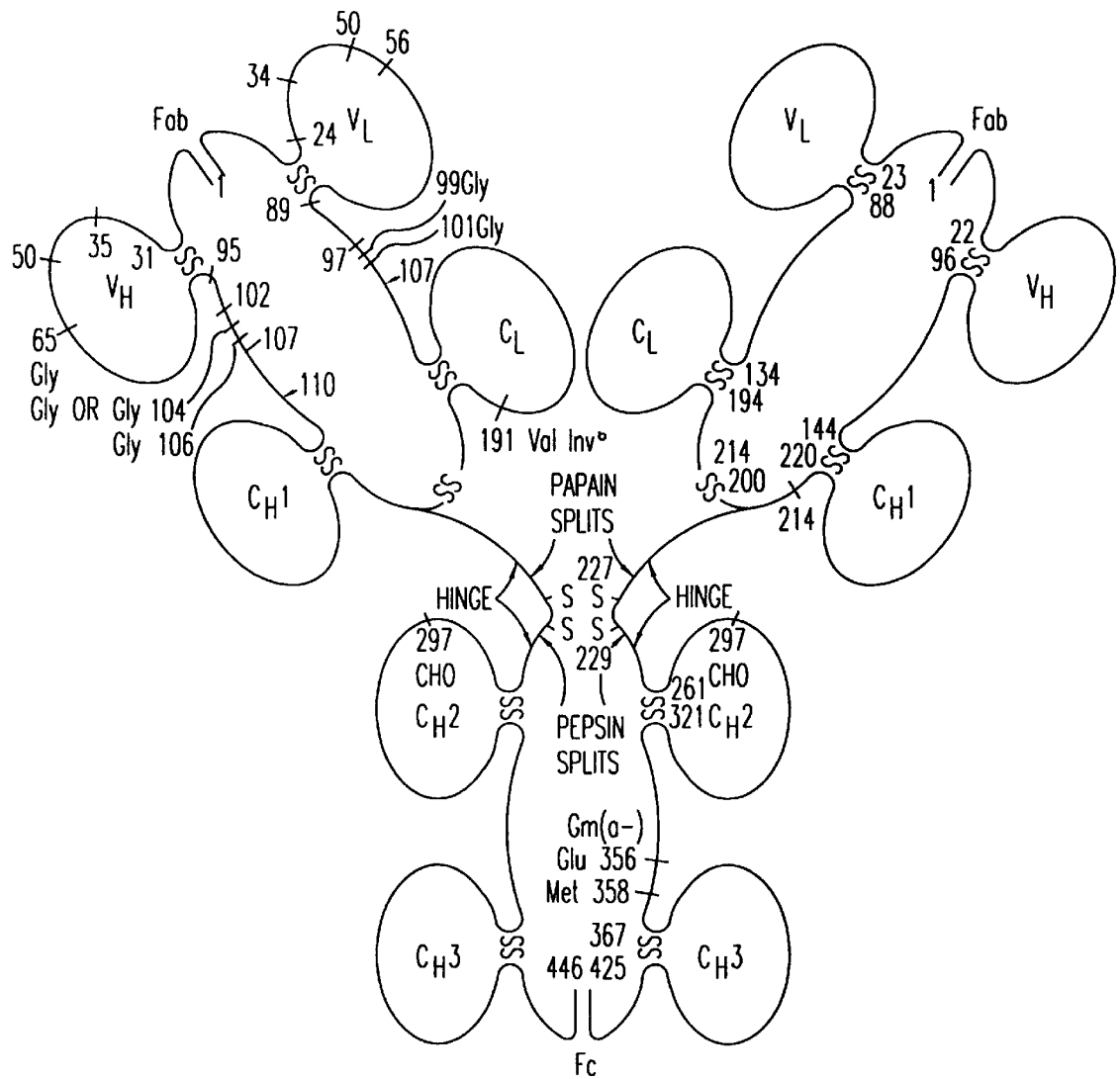
FIG. 14 shows a schematic view of the four-chain structure of a human IgG molecule.

Preparation of Multivalent Antigen-Binding Proteins by Chemical Cross-Linking Free cysteines were engineered into the C-terminal end of the 4-4-20/212 single-chain antigen-binding protein, in order to chemically crosslink the protein. The design was based on the hinge region found in antibodies between the C$_H$1 and C$_H$2 regions. In order to try to reduce antigenicity in humans, the hinge sequence of the most common IgG class, IgG1, was chosen. The 4-4-20 Fab structure was examined and it was determined that the C-terminal sequence GluH216-ProH217-ArgH218, was part of the C$_H$1 region and that the hinge between C$_H$1 and C$_H$2 starts with ArgH218 or GlyH219 in the mouse 4-4-20 IgG2A antibody. FIG. 14 shows the structure of a human IgG. The hinge region is indicated generally. Thus the hinge from human IgG1 would start with LysH218 or SerH219. (See Table 5).

The C-terminal residue in most of the single-chain antigen-binding proteins described to date is the amino acid serine. In the design for the hinge region, the C-terminal serine in the 4-4-20/212 single-chain antigen-binding protein was made the first serine of the hinge and the second residue of the hinge was changed from a cysteine to a serine. This hinge cysteine normally forms a disulfide bridge to the C-terminal cysteine in the light chain.

TABLE 5

| IgG2A mouse[1] | E P R G P T I K P   C P P C L C - |
|---|---|
| IgG1 human[2] | A E P K   S C D K T H T C P P C - |
| SCA*[3] | - - V T V S |
| SCA* Hinge design 1[4] | - - V T V S S D K T H T C |
| SCA* Hinge design 2[5] | - - V T V S S D K T H T C P P C |

*single-chain antigen-binding protein
(1) SEQ ID NO. 5
(2) SEQ ID NO. 6
(3) SEQ ID NO. 7
(4) SEQ ID NO. 8
(5) SEQ ID NO. 9

There are possible advantages to having two C-terminal cysteines, for they might form an intramolecular disulfide bond, making the protein recovery easier by protecting the sulfurs from oxidation. The hinge regions were added by introduction of a BstE II restriction site in the 3'-terminus of the gene encoding the 4-4-20/212 single-chain antigen-binding protein (see FIGS. 15A–15B).

The monomeric single-chain antigen-binding protein containing the C-terminal cysteine can be purified using the normal methods of purifying a single-chain antigen-binding proteins, with minor modifications to protect the free sulfhydryls. The cross-linking could be accomplished in one of two ways. First, the purified single-chain antigen-binding protein could be treated with a mild reducing agent, such as dithiothreitol, then allowed to air oxidize to form a disulfide-bond between the individual single-chain antigen-binding proteins. This type of chemistry has been successful in producing heterodimers from whole antibodies (Nisonoff et al., Quantitative Estimation of the Hybridization of Rabbit Antibodies, *Nature* 4826:355–359 (1962); Brennan et al., Preparation of Bispecific Antibodies by Chemical Recombination of Monoclonal Immunoglobulin G$_1$ Fragments, *Science* 229:81–83 (1985)). Second, chemical crosslinking agents such as bismaleimidehexane could be used to crosslink two single-chain antigen-binding proteins by their C-terminal cysteines. See Partis et al., *J. Prot. Chem.* 2:263–277 (1983).

EXAMPLE 6

Genetic Construction of Bivalent Antigen-Binding Proteins

Figure 17:
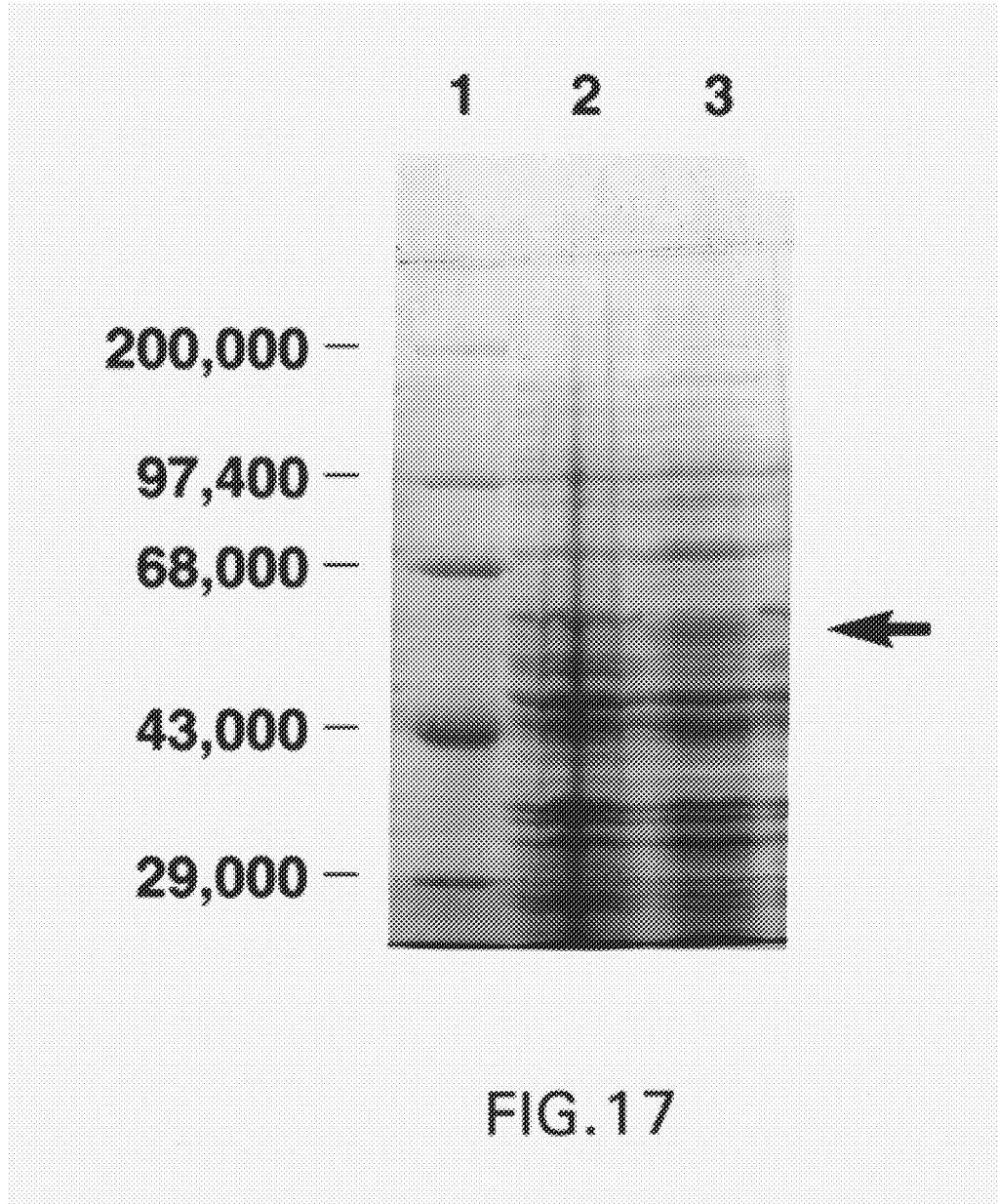
FIG. 17 shows the expression of the divalent CC49/212 single-chain antigen-binding protein of FIG. 16 at 42° C., on an SDS-PAGE gel containing total E. coli protein. Lane 1 contains the molecular weight standards. Lane 2 is the uninduced E. coli production strain grown at 30° C. Lane 3 is divalent CC49/212 single-chain antigen-binding protein induced by growth at 42° C. The arrow shows the band of expressed divalent CC49/212 single-chain antigen-binding protein.

Bivalent antigen-binding proteins can be constructed genetically and subsequently expressed in *E. coli* or other known expression systems. This can be accomplished by genetically removing the stop codons at the end of a gene encoding a monomeric single-chain antigen-binding protein and inserting a linker and a gene encoding a second single-chain antigen-binding protein. We have constructed a gene for a bivalent CC49/212 antigen-binding protein in this manner (see FIG. 16). The CC49/212 gene in the starting expression plasmid is in an Aat II to Bam H1 restriction fragment (see Bird et al., Single-Chain Antigen-Binding Proteins, *Science* 242:423–426 (1988); and Whitlow et al., Single-Chain F$_V$ Proteins and Their Fusion Proteins, *Methods* 2:97–105 (1991)). The two stop codons and the Bam H1 site at the C-terminal end of the CC49/212 antigen-binding protein gene were replaced by a single residue linker (Ser) and an Aat II restriction site. The resulting plasmid was cut with Aat II and the purified Aat II to Aat II restriction fragment was ligated into Aat II cut CC49/212 single-chain antigen-binding protein expression plasmid. The resulting bivalent CC49/212 single-chain antigen-binding protein expression plasmid was transfected into an *E. coli* expression host that contained the gene for the cI857 temperature-sensitive repressor. Expression of single-chain antigen-binding protein in this system is induced by raising the temperature from 30° C. to 42° C. FIG. 17 shows the expression of the divalent CC49/212 single-chain antigen-binding protein of FIG. 16 at 42° C., on an SDS-PAGE gel containing total *E. coli* protein. Lane 1 contains the molecular weight standards. Lane 2 is the uninduced *E. coli* production strain grown at 30° C. Lane 3 is divalent CC49/212 single-chain antigen-binding protein induced by growth at 42° C. The arrow shows the band of expressed divalent CC49/212 single-chain antigen-binding protein.

EXAMPLE 7

Construction, Purification, and Testing of 4-4-20/CC49 Heterodimer F$_V$ With 217 Linkers The goals of this experiment were to produce, purify and analyze for activity a new heterodimer Fv that would bind to both fluorescein and the pancarcinoma antigen TAG-72. The design consisted of two polypeptide chains, which associated to form the active heterodimer Fv. Each polypeptide chain can be described as a mixed single-chain Fv (mixed sFv). The first mixed sFv (GX 8952) comprised a 4-4-20 variable light chain ($V_L$) and a CC-49 variable heavy chain ($V_H$) connected by a 217 polypeptide linker (FIG. 19A). The second mixed sFv (GX 8953) comprised a CC-49 $V_L$ and a 4-4-20 $V_H$ connected by a 217 polypeptide linker (FIG. 19B). The sequence of the 217 polypeptide linker is shown in Table 3. Construction of analogous CC49/4-4-20 heterodimers connected by a 212 polypeptide linker were described in Example 4.

Results

A. Purification

One 10-liter fermentation of each mixed sFv was grown on casein digest-glucose-salts medium at 32° C. to an optical density at 600 nm of 15 to 20. The mixed sFv expression was induced by raising the temperature of the fermentation to 42° C. for one hour. 277 gm (wet cell weight) of *E. coli* strain GX 8952 and 233 gm (wet cell weight) of *E. coli* strain GX8953 were harvested in a centrifuge at 7000 g for 10 minutes. The cell pellets were kept and the supernate discarded. The cell pellets were frozen at −20° C. for storage.

2.55 liters of "lysis/wash buffer" (50 mM Tris/200 mM NaCl/1 mM EDTA, pH 8.0) was added to both of the mixed sFv's cell pellets, which were previously thawed and combined to give 510 gm of total wet cell weight. After complete suspension of the cells they were then passed through a Gaulin homogenizer at 9000 psi and 4° C. After this first pass the temperature increased to 23° C. The temperature was immediately brought down to 0° C. using dry ice and methanol. The cell suspension was passed through the Gaulin homogenizer a second time and centrifuged at 8000 rpm with a Dupont GS-3 rotor for 60 minutes. The supernatant was discarded after centrifugation and the pellets resuspended in 2.5 liters of "lysis/wash buffer" at 4° C. This suspension was centrifuged for 45 minutes at 8000 rpm with the Dupont GS-3 rotor. The supernatant was again discarded and the pellet weighed. The pellet weight was 136.1 gm.

1300 ml of 6M Guanidine Hydrochloride/50 mM Tris/50 mM KCl/10 mM $CaCl_2$ pH 8.0 at 4° C. was added to the washed pellet. An overhead mixer was used to speed solubilization. After one hour of mixing, the heterodimer GuHCl extract was centrifuged for 45 minutes at 8000 rpm and the pellet was discarded. The 1425 ml of heterodimer Fv 6M GuHCl extract was slowly added (16 ml/min) to 14.1 liters of "Refold Buffer" (50 mM Tris/50 mM KCl/10 mM $CaCl_2$, pH 8.0) under constant mixing at 4° C. to give an approximate dilution of 1:10. Refolding took place overnight at 4° C.

After 17 hours of refolding the anti-fluorescein activity was checked by a 40% quenching assay, and the amount of active protein calculated. 150 mg total active heterodimer Fv was found by the 40% quench assay, assuming a 54,000 molecular weight.

4 liters of prechilled (4° C.) 190 proof ethanol was added to the 15 liters of refolded heterodimer with mixing for 3 hours. The mixture sat overnight at 4° C. A flocculent precipitate had settled to the bottom after this overnight treatment. The nearly clear solution was filtered through a Millipak-200 (0.22μ) filter so as to not disturb the precipitate. A 40% quench assay showed that 10% of the anti-fluorescein activity was recovered in the filtrate.

The filtered sample of heterodimer was dialyzed, using a Pellicon system containing 10,000 dalton MWCO membranes, with "dialysis buffer" 40 mM MOPS/0.5 mM Calcium Acetate (CaAc), pH 6.4 at 4° C. 20 liters of dialysis buffer was required before the conductivity of the retentate was equal to that of the dialysis buffer (~500 μS). After dialysis the heterodimer sample was filtered through a Millipak-20 filter, 0.22μ. After this step a 40% quench assay showed there was 8.8 mg of active protein.

The crude heterodimer sample was loaded on a Poly CAT A cation exchange column at 20 ml/min. The column was previously equilibrated with 60 mM MOPS, 1 mM CaAc pH 6.4, at 4° C., (Buffer A). After loading, the column was washed with 150 ml of "Buffer A" at 15 ml/min. A 50 min linear gradient was performed at 15 ml/min using "Buffer A" and "Buffer B" (60 mM MOPS, 20 mM CaAc pH 7.5 at 4° C.). The gradient conditions are presented in Table 6. "Buffer C" comprises 60 mM MOPS, 100 mM $CaCl_2$, pH 7.5.

TABLE 6

| Time | %A | %B | %C | Flow |
|---|---|---|---|---|
| 0:00 | 100.0 | 0.0 | 0.0 | 15ml/min |
| 50:00 | 0.0 | 100.0 | 0.0 | 15ml/min |
| 52:00 | 0.0 | 100.0 | 0.0 | 15ml/min |
| 54:00 | 0.0 | 0.0 | 100.0 | 15ml/min |
| 58:00 | 0.0 | 0.0 | 100.0 | 15ml/min |
| 60:00 | 100.0 | 0.0 | 0.0 | 15ml/min |

Figure 20:
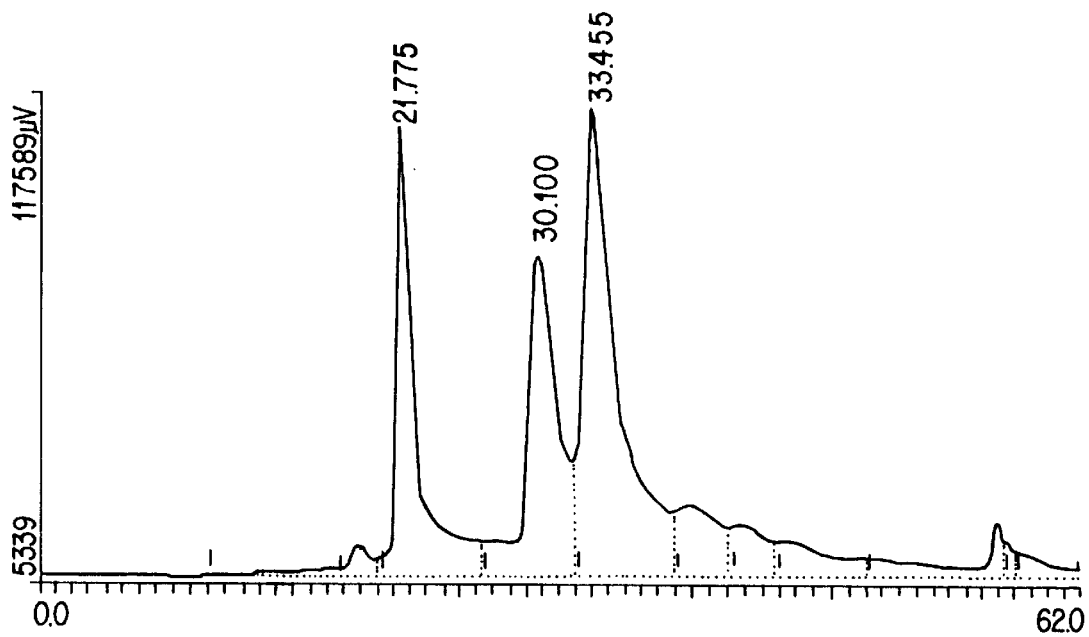
FIG. 20 is a chromatogram depicting the purification of CC49/4-4-20 heterodimer Fv on a cation exchange high performance liquid chromatographic column. The column is a PolyCAT A aspartic acid column (Poly LC, Columbia, Md.). The heterodimer Fv is shown as fraction 5, eluting at 30.10 min.

Approximately 50 ml fractions were collected and analyzed for activity, purity, and molecular weight by size-exclusion chromatography. The fractions were not collected by peaks, so contamination between peaks is likely. Fractions 3 through 7 were pooled (total volume—218 ml), concentrated to 50 ml and dialyzed against 4 liters of 60 mM MOPS, 0.5 mM CaAc pH 6.4 at 4° C. overnight. The dialyzed pool was filtered through a 0.22μ filter and checked for absorbance at 280 nm. The filtrate was loaded onto the PolyCAT A column, equilibrated with 60 mM MOPS, 1 mM CaAc pH 6.4 at 4° C., at a flow rate of 10 ml/min. Buffer B was changed to 60 mM MOPS, 10 mM CaAc pH 7.5 at 4° C. The gradient was run as in Table 6. The fractions were collected by peak and analyzed for activity, purity, and molecular weight. The chromatogram is shown in FIG. 20. Fraction identification and a analysis is presented in Table 7.

TABLE 7

| Fraction Analysis of the Heterodimer Fv protein | | | |
|---|---|---|---|
| Fraction No. | $A_{280}$ reading | Total Volume (ml) | HPLC-SE Elution Time (min) |
| 2 | 0.161 | 36 | 20.525 |
| 3 | 0.067 | 40 | |
| 4 | 0.033 | 40 | |
| 5 | 0.178 | 45 | 19.133 |
| 6 | 0.234 | 50 | 19.163 |
| 7 | 0.069 | 50 | |
| 8 | 0.055 | 40 | |

Figure 21:
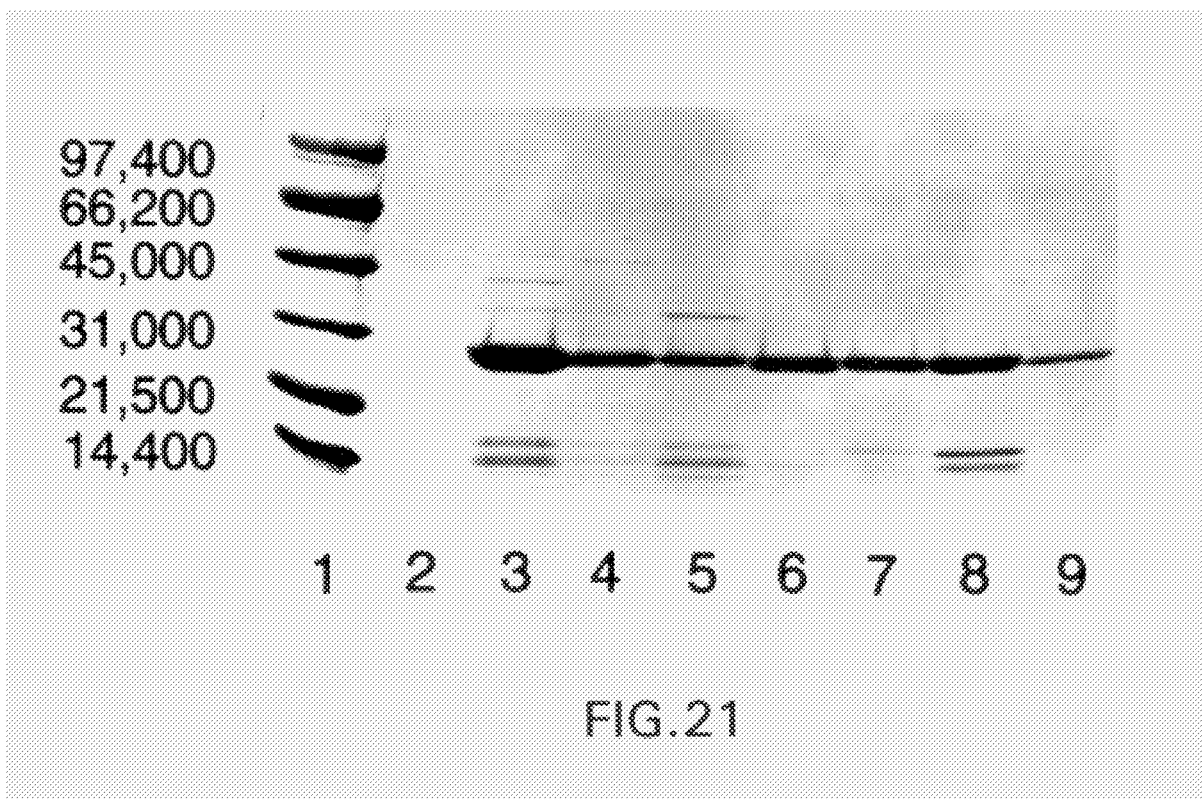
FIG. 21 is a coomassie-blue stained 4–20% SDS-PAGE gel showing the proteins separated in FIG. 20. Lane 1 contains the molecular weight standards. Lane 3 contains the starting material before separation. Lanes 4–8 contain fractions 2, 3, 5, 6 and 7 respectively. Lane 9 contains purified CC49/212.

Fractions 2 to 7 and the starting material were analyzed by SDS gel electrophoresis, 4–20%. A picture and description of the gel is presented in FIG. 21.

B. HPLC Size Exclusion Results

Figure 22A:
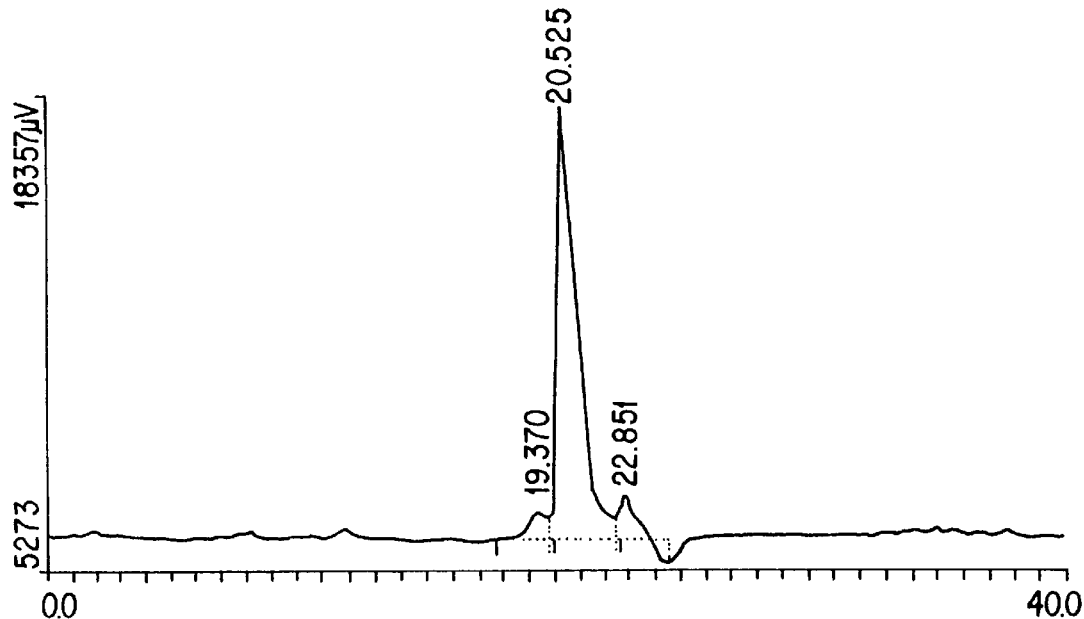
FIG. 22A is a chromatogram used to determine the molecular size of fraction 2 from FIG. 20. A TSK G3000SW gel filtration HPLC column was used (Toyo Soda, Tokyo, Japan).
Figure 22B:
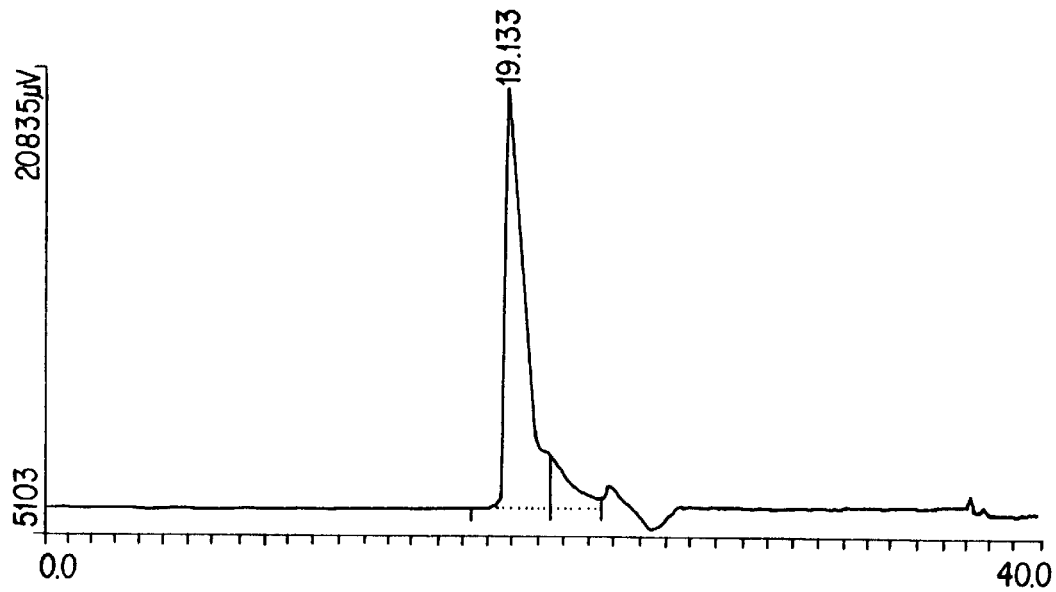
FIG. 22B is a chromatogram used to determine the molecular size of fraction 5 from FIG. 20. A TSK G3000SW gel filtration HPLC column was used (Toyo Soda, Tokyo, Japan).
Figure 22C:
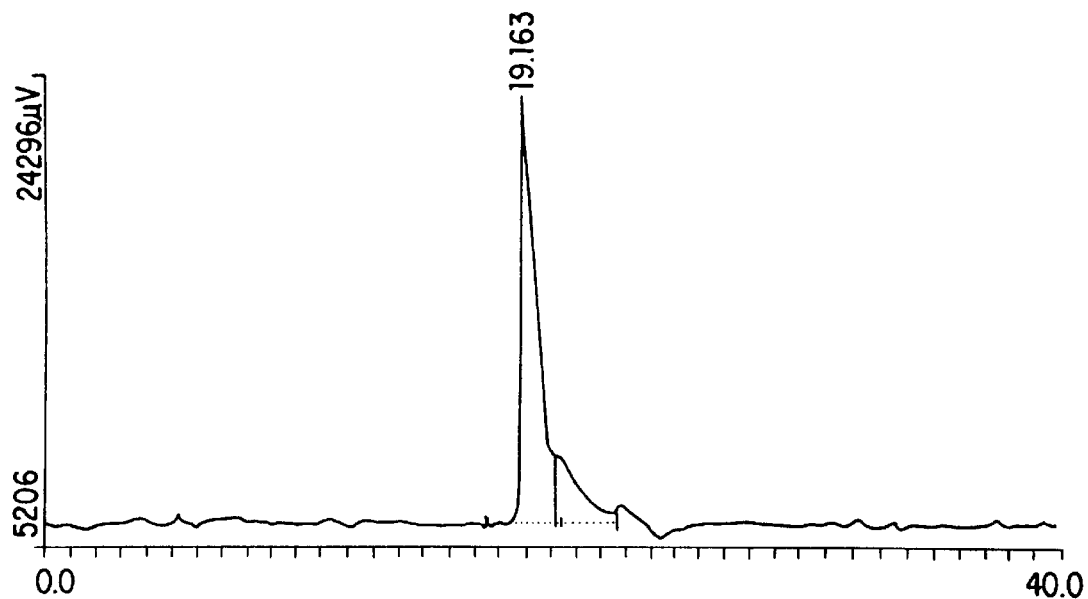
FIG. 22C is a chromatogram used to determine the molecular size of fraction 6 from FIG. 20. A TSK G30005W gel filtration HPLC column was used (Toyo Soda, Tokyo, Japan).

Fractions 2, 5, and 6 correspond to the three main peaks in FIG. 20 and therefore were chosen to be analyzed by HPLC size exclusion. Fraction 2 corresponds to the peak that runs at 21.775 minutes in the preparative purification (FIG. 20), and runs on the HPLC sizing column at 20.525 minutes, which is in the monomeric position (FIG. 22A). Fractions 5 and 6 (30.1 and 33.455 minutes, respectively, in FIG. 20) run on the HPLC sizing column (FIGS. 22B and 22C) at 19.133 and 19.163 minutes, respectively (see Table 7). Therefore, both of these peaks could be considered dimers. 40% Quenching assays were performed on all fractions of this purification. Only fraction 5 gave significant activity. 2.4 mg of active CC49 4-4-20 heterodimer Fv was recovered in fraction 5, based on the Scatchard analysis described below.

C. N-terminal sequencing of the fractions

The active heterodimer Fv fraction should contain both polypeptide chains. N-terminal sequence analysis showed that fractions 5 and 6 displayed N-terminal sequences consistent with the prescence of both CC49 and 4-4-20 polypeptides and fraction 2 displayed a single sequence corresponding to the CC49/212/4-4-20 polypeptide only. We believe that fraction 6 was contaminated by fraction 5 (see FIG. 20), since only fraction 5 had significant activity.

D. Anti-fluorescein activity by Scatchard analysis

Figure 23:
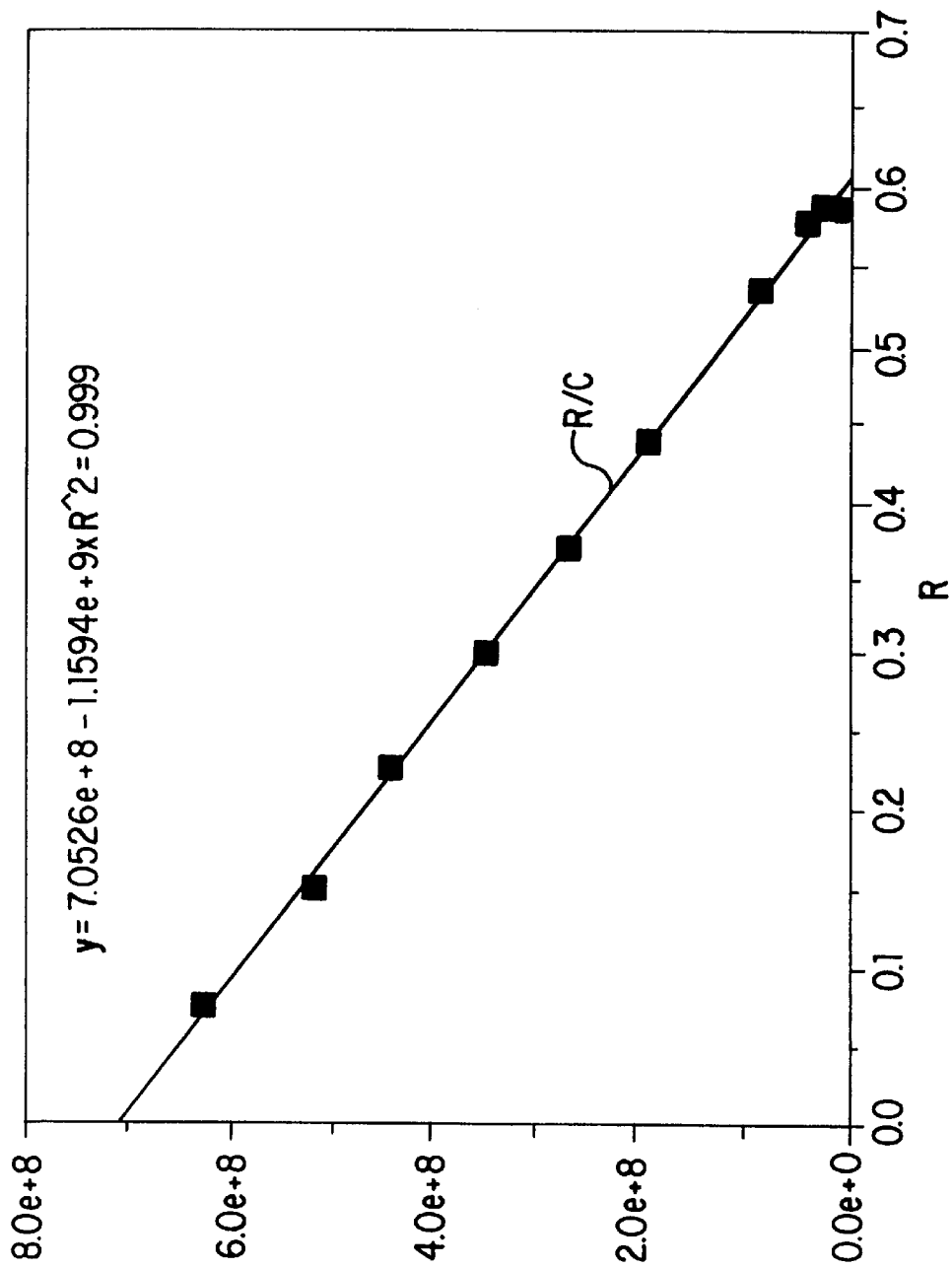
FIG. 23 shows a Scatchard analysis of the fluorescein binding affinity of the CC49 4-4-20 heterodimer Fv (fraction 5 in FIG. 20).

The fluorescein association constants (Ka) were determined for fractions 5 and 6 using the fluorescence quenching assay described by Herron, J. N., in *Fluorescence Hapten: An Immunological Probe*, E. W. Voss, ed., CRC Press, Boca Raton, Fla. (1984). Each sample was diluted to approximately $5.0 \times 10^{-8}$M with 20 mM HEPES buffer pH 8.0. 590 $\mu$l of the $5.0 \times 10^{-8}$M sample was added to a cuvette in a fluorescence spectrophotometer equilibrated at room temperature. In a second cuvette 590 $\mu$l of 20 mM HEPES buffer pH 8.0 was added. To each cuvette was added 10 $\mu$l of $3.0 \times 10^{-7}$M fluorescein in 20 mM HEPES buffer pH 8.0, and the fluorescence recorded. This is repeated until 140 $\mu$l of fluorescein had been added. The resulting Scatchard analysis for fraction 5 shows a binding constant of $1.16 \times 10^9 M^{-1}$ for fraction #5 (see FIG. 23). This is very close to the 4-4-20/212 sFv constant of $1.1 \times 10^9 M^{-1}$ (see Pantoliano et al., *Biochemistry* 30:10117–10125 (1991)). The R intercept on the Scatchard analysis represents the fraction of active material. For fraction 5, 61% of the material was active. The graph of the Scatchard analysis on fraction 6 shows a binding constant of $3.3 \times 10^8 M^{-1}$ and 14% active. The activity that is present in fraction 6 is most likely contaminants from fraction 5.

E. Anti-TAG-72 activity by competition ELISA

The CC49 monoclonal antibody was developed by Dr. Jeffrey Schlom's group, Laboratory of Tumor Immunology and Biology, National Cancer Institute. It binds specifically to the pan-carcinoma tumor antigen TAG-72. See Muraro, R., et al., *Cancer Research* 48:4588–4596 (1988).

Figure 24:
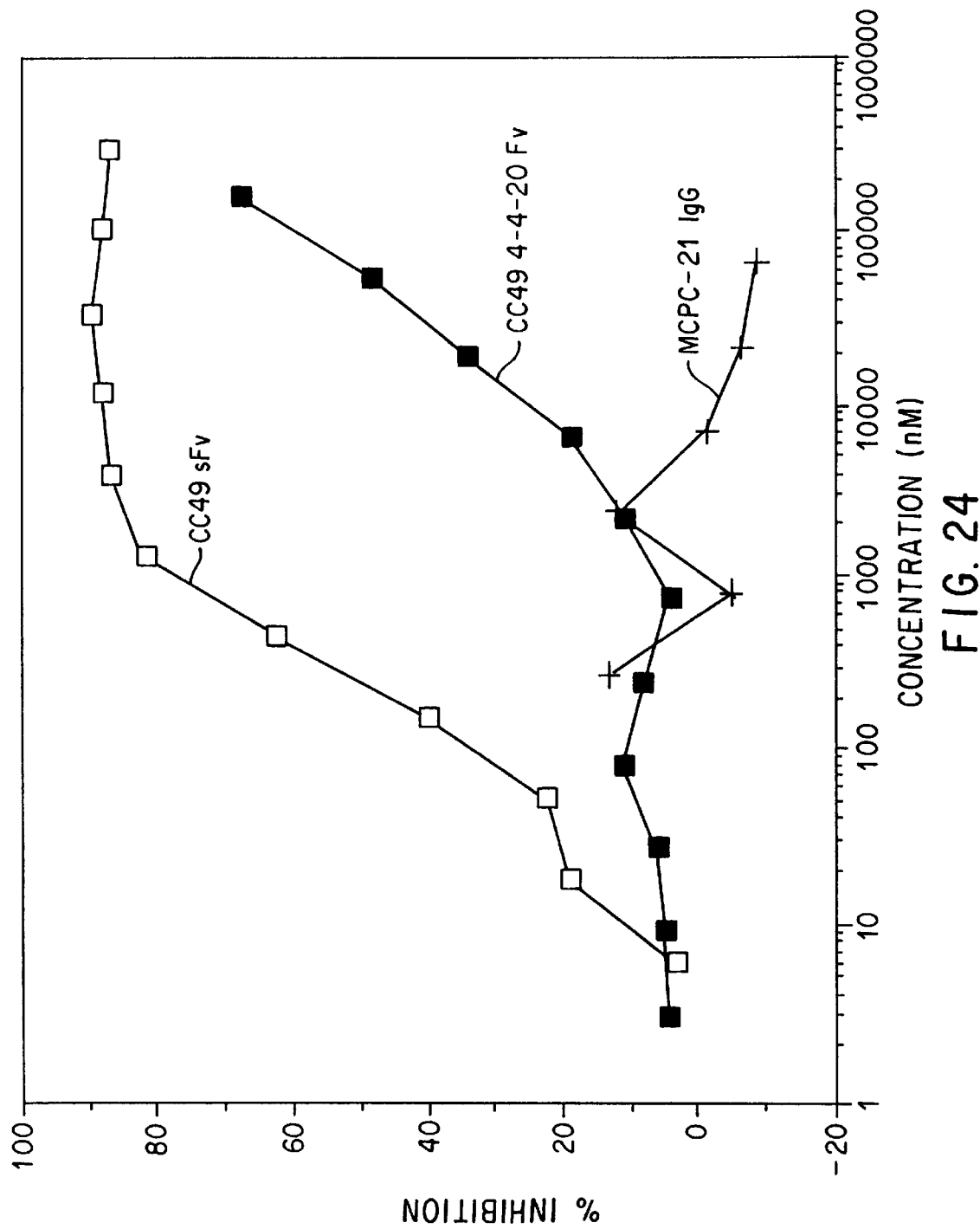
FIG. 24 is a graphical representation of three competition enzyme-linked immunosorbent assays (ELISA) in which unlabeled CC49 4-4-20 Fv (closed squares) CC49/212 single-chain Fv (open squares) and MOPC-21 IgG (+) competed against a biotin-labeled CC49 IgG for binding to the TAG-72 antigen on a human breast carcinoma extract. MOPC-21 is a control antibody that does not bind to TAG-72 antigen.

To determine the binding properties of the bivalent CC49/4-4-20 Fv (fraction 5) and the CC49/212 sFv, a competition enzyme-linked immunosorbent assay (ELISA) was set up in which a CC49 IgG labeled with biotin was competed against unlabeled CC49/4-4-20 Fv and the CC49/212 sFv for binding to TAG-72 on a human breast carcinoma extract (see FIG. 24). The amount of biotin-labeled CC49 IgG was determined using a preformed complex with avidin and biotin coupled to horse radish peroxidase and O-phenylenediamine dihydrochloride (OPD). The reaction was stopped with 4N $H_2SO_4$ (sulfuric acid), after 10 min. and the optical density read at 490 nm. This competition ELISA showed that the bivalent CC49/4-4-20 Fv binds to the TAG-72 antigen. The CC49/4-4-20 Fv needed a two hundred-fold higher protein concentration to displace the IgG than the single-chain Fv.

EXAMPLE 8

Cross-Linking Antigen-Binding Dimers

We have chemically crosslinked dimers of 4-4-20/212 antigen-binding protein with the two cysteine C-terminal extension (4-4-20/212 CPPC single-chain antigen-binding protein) in two ways. In Example 5 we describe the design and genetic construction of the 4-4-20/212 CPPC single-chain antigen-binding protein (hinge design 2 in Table 5). FIG. 15B shows the nucleic acid and protein sequences of this protein. After purifying the 4-4-20/212 CPPC single-chain antigen-binding protein, using the methods described in Whitlow and Filpula, *Meth. Enzymol.* 2:97 (1991), dimers were formed by two methods. First, the free cysteines were mildly reduced with dithiothreitol (DTT) and then the disulfide-bonds between the two molecules were allowed to form by air oxidation. Second, the chemical crosslinker bis-maleimidehexane was used to produce dimers by crosslinking the free cysteines from two 4-4-20/212 CPPC single-chain antigen-binding proteins.

Figure 25:
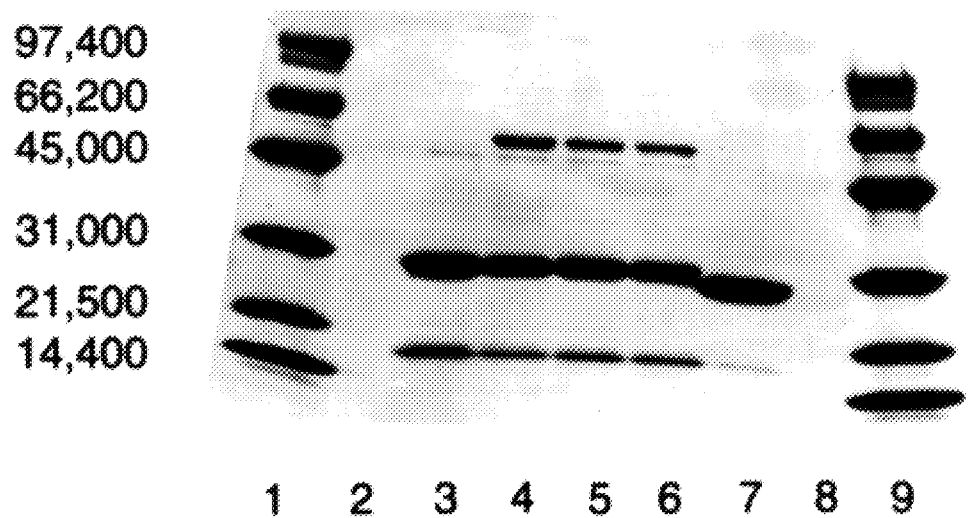
FIG. 25 shows a coomassie-blue stained non-reducing 4–20% SDS-PAGE gel. Lanes 1 and 9 contain the molecular weight standards. Lane 3 contains the 4-4-20/212 CPPC single-chain antigen-binding protein after purification. Lane 4, 5 and 6 contain the 4-4-20/212 CPPC single-chain antigen-binding protein after treatment with DTT and air oxidation. Lane 7 contains 4-4-20/212 single-chain antigen-binding protein.

A 0.1 mg/ml solution of the 4-4-20/212 CPPC single-chain antigen-binding protein was mildly reduced using 1 mM DTT, 50 mM HEPES, 50 mM NaCl, 1 mM EDTA buffer pH 8.0 at 4° C. The samples were dialyzed against 50 mM HEPES, 50 mM NaCl, 1 mM EDTA buffer pH 8.0 at 4° C. overnight, to allow the oxidation of free sulfhydrals to intermolecular disulfide-bonds. FIG. 25 shows a non-reducing SDS-PAGE gel after the air oxidation; it shows that approximately 10% of the 4-4-20/212 CPPC protein formed dimers with molecular weights around 55,000 Daltons.

Figure 26:
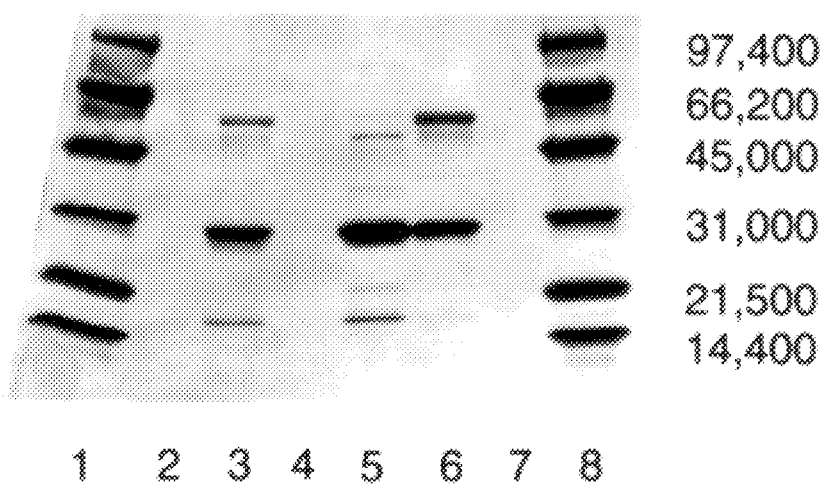
FIG. 26 shows a coomassie-blue stained reducing 4–20% SDS-PAGE gel (samples were treated with β-mercaptoethanol prior to being loaded on the gel). Lanes 1 and 8 contain the molecular weight standards. Lane 3 contains the 4-4-20/212 CPPC single-chain antigen-binding protein after treatment with bis-maleimidehexane. Lane 5 contains peak 1 of bis-maleimidehexane treated 4-4-20/212 CPCC single-chain antigen-binding protein. Lane 6 contains peak 3 of bis-maleimidehexane treated 4-4-20/212 CPPC single-chain antigen-binding protein.

A 0.1 mg/ml solution of the 4-4-20/212 CPPC single-chain antigen-binding protein was treated with 2 mM bis-maleimidehexane. Unlike forming a disulfide-bond between two free cysteines in the previous example, the bis-maleimidehexane crosslinker material should be stable to reducing agents such as β-mercaptoethanol. FIG. 26 shows that approximately 5% of the treated material produced dimer with a molecular weight of 55,000 Daltons on a reducing SDS-PAGE gel (samples were treated with β-mercaptalethanol prior to being loaded on the gel). We further purified the bis-maleimidehexane treated 4-4-20/212 CPPC protein on PolyCAT A cation exchange column after the protein had been extensively dialyzed against buffer A. FIG. 26 shows that we were able to enhance the fraction containing the dimer to approximately 15%.

Conclusions

We have produced a heterodimer Fv from two complementary mixed sFv's which has been shown to have the size of a dimer of the sFv's . The N-terminal analysis has shown that the active heterodimer Fv contains two polypeptide chains. The heterodimer Fv has been shown to be active for both fluorescein and TAG-72 binding.

All publications cited herein are incorporated fully into this disclosure by reference.

From the foregoing it will be appreciated that, although specific embodiments of the invention have been described herein for purposes of illustration, various modifications may be made without deviating from the spirit and scope of the invention and the following claims. As examples, the steps of the preferred embodiment constitute only one form of carrying out the process in which the invention may be embodied.

What is claimed is:

1. A composition comprising an antigen-binding protein having more than 50% of said protein in multivalent form, said protein in multivalent form comprising two or more single-chain molecules, each single-chain molecule comprising:

(a) a first polypeptide comprising the binding portion of the variable region of an antibody light chain;

(b) a second polypeptide comprising the binding portion of the variable region of an antibody heavy chain; and (c) a peptide linker linking said first and second polypeptides (a) and (b); or (d) a first polypeptide comprising the binding portion of the variable region of an antibody heavy chain;

(e) a second polypeptide comprising the binding portion of the variable region of an antibody light chain; and (f) a peptide linker linking said first and second polypeptides (d) and (e).

2. The composition according to claim 1, said composition having more than 84% of said protein in multivalent form.

3. The composition according to claim 1, said composition having more than 95% of said protein in multivalent form.

4. The composition according to claim 1 wherein said single-chain molecules are non-covalently linked to each other.

5. The composition according to claim 2 wherein said single-chain molecules are non-covalently linked to each other.

6. The composition according to claim 3 wherein said single-chain molecules are non-covalently linked to each other.

7. The composition according to claim 1 wherein said single-chain molecules are chemically cross-linked to each other.

8. The composition according to claim 2 wherein said single-chain molecules are chemically cross-linked to each other.

9. The composition according to claim 3 wherein said single-chain molecules are chemically cross-linked to each other.

10. The composition according to claim 1 wherein said single-chain molecules are cross-linked to each other by one or more disulfide-bonds.

11. The composition according to claim 10 wherein at least one of said single-chain molecules contains one or more engineered cysteine residues.

12. The composition according to claim 2 wherein said single-chain molecules are cross-linked to each other by one or more disulfide-bonds.

13. The composition according to claim 12 wherein at least one of said single-chain molecules contains one or more engineered cysteine residues.

14. The composition according to claim 3 wherein said single-chain molecules are cross-linked to each other by one or more disulfide-bonds.

15. The composition according to claim 14 wherein at least one of said single-chain molecules contains one or more engineered cysteine residues.

16. The composition according to claim 1 wherein said protein in multivalent form is heterobivalent antigen-binding protein.

17. The composition according to claim 2 wherein said protein in multivalent form is heterobivalent antigen-binding protein.

18. The composition according to claim 3 wherein said protein in multivalent form is heterobivalent antigen-binding protein.

19. The composition according to claim 1 wherein said protein in multivalent form is homobivalent antigen-binding protein.

20. The composition according to claim 2 wherein said protein in multivalent form is homobivalent antigen-binding protein.

21. The composition according to claim 3 wherein said protein in multivalent form is homobivalent antigen-binding protein.

22. The composition according to claim 1 wherein said linker is selected from the group consisting of linkers 202' (SEQ ID NO:1), 212 (SEQ ID NO:2), 216 (SEQ ID NO:3), and 217 (SEQ ID NO:4).

23. The composition according to claim 2 wherein said linker is selected from the group consisting of linkers 202' (SEQ ID NO: 1), 212 (SEQ ID NO:2), 216 (SEQ ID NO:3), and 217 (SEQ ID NO:4).

24. The composition according to claim 3 wherein said linker is selected from the group consisting of linkers 202' (SEQ ID NO:1), 212 (SEQ ID NO:2), 216 (SEQ ID NO:3), and 217 (SEQ ID NO:4).

25. A composition comprising a B6.2/212 antigen-binding protein having more than 50% of said protein in multivalent form.

26. The composition according to claim 25, said composition having more than 78% of said protein in multivalent form.

27. A composition comprising a CC49/212 antigen-binding protein having more than 50% of said protein in multivalent form.

28. The composition according to claim 27, said composition having more than 84% of said protein in multivalent form.

29. The composition according to claim 27, said composition having more than 90% of said protein in multivalent form.

* * * * *

UNITED STATES PATENT AND TRADEMARK OFFICE
CERTIFICATE OF CORRECTION

PATENT NO. : 5,869,620

DATED : February 9, 1999

INVENTORS : Whitlow *et al.*

It is certified that an error appears in the above-identified patent and that said Letters Patent is hereby corrected as shown below.

On the title page, at line 1 of item [75] ("Inventors"), please delete "Gaithersburg" and insert therein --El Sobrante, Ca.--.

at line 2 of item [75] ("Inventors"), please delete "both of".

at line 5 of item [75] ("Inventors"), please delete "Gaithersburg, Md." and insert therein --Piscataway, NJ.--.

On page 2, second column, at line 18, please delete "$F(ab'\gamma)_2$" and insert therein --$F(ab'\gamma)_2$--.

Column 7, line 36, please delete "coomassie" and insert therein --Coomassie--.

Column 7, line 66, please delete "coomassie" and insert therein --Coomassie--.

Column 8, line 7, please delete "coomassie" and insert therein --Coomassie--.

Column 8, line 14, please delete "CPCC" and insert therein --CPPC--.

Column 14, line 1, please delete "know" and insert therein --known--.

Column 14, line 23, please delete "murecomlent" and insert therein --multivalent--.

Column 18, line 38, please delete "isoproanol" and insert therein --isopropanol--.

Column 21, line 21, please delete " $4\text{-}4\text{-}20V_L 212/CC49V_H$ " and insert therein --$4\text{-}4\text{-}20V_L/212/CC49V_H$--.

UNITED STATES PATENT AND TRADEMARK OFFICE
CERTIFICATE OF CORRECTION

PATENT NO. : 5,869,620

Page 2 of 2

DATED : February 9, 1999

INVENTORS : Whitlow et al.

It is certified that an error appears in the above-identified patent and that said Letters Patent is hereby corrected as shown below.

Column 23, lines 5 and 7, please delete "CC-49" and insert therein --CC49--.

Column 23, line 23, please delete "supernate" and insert therein --supernatant--.

Column 26, line 27, please delete "sulfhydra and insert therein --sulfhydryls--.

Column 58, lines 20 and 28, please delete "216" and insert therein --216--.

Title page, item [75] Inventors: delete the following:
"Michele Rollence, Damascus, Md."

Signed and Sealed this

Fifth Day of December, 2000

Attest:

Q. TODD DICKINSON

*Attesting Officer*      *Director of Patents and Trademarks*

UNITED STATES PATENT AND TRADEMARK OFFICE
CERTIFICATE OF CORRECTION

PATENT NO.    : 5,869,620
DATED         : February 9, 1999
INVENTOR(S)   : Whitlow et al.

It is certified that error appears in the above-identified patent and that said Letters Patent is hereby corrected as shown below:

<u>Title page,</u>
Item [75] Inventors, please add the following:
-- Michele Rollence, Damascus, Md. --"

Signed and Sealed this

Eleventh Day of September, 2001

Attest:

Attesting Officer

NICHOLAS P. GODICI
Acting Director of the United States Patent and Trademark Office

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: both ( x i ) SEQUENCE DESCRIPTION: SEQ ID NO:1:

Gly Lys Ser Ser Gly Ser Gly Ser Glu Ser Lys Ser
    1                5                       10

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( D ) TOPOLOGY: both ( x i ) SEQUENCE DESCRIPTION: SEQ ID NO:2:

Gly Ser Thr Ser Gly Ser Gly Lys Ser Ser Glu Gly Lys Gly
    1                5                       10

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( D ) TOPOLOGY: both ( x i ) SEQUENCE DESCRIPTION: SEQ ID NO:3:

Gly Ser Thr Ser Gly Ser Gly Lys Ser Ser Glu Gly Ser Gly Ser Thr
    1                5                       10                   15

Lys Gly ( 2 ) INFORMATION FOR SEQ ID NO:4:

( i ) SEQUENCE CHARACTERISTICS:
        ( A ) LENGTH: 12 amino acids
        ( B ) TYPE: amino acid
        ( D ) TOPOLOGY: both ( x i ) SEQUENCE DESCRIPTION: SEQ ID NO:4:

Gly Ser Thr Ser Gly Lys Pro Ser Glu Gly Lys Gly
    1                5                       10

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: both ( x i ) SEQUENCE DESCRIPTION: SEQ ID NO:5:

Glu Pro Arg Gly Pro Thr Ile Lys Pro Cys Pro Pro Cys Leu Cys
    1                5                       10                   15

( 2 ) INFORMATION FOR SEQ ID NO:6:

( i ) SEQUENCE CHARACTERISTICS:
        ( A ) LENGTH: 15 amino acids
        ( B ) TYPE: amino acid (D) TOPOLOGY: both (x i) SEQUENCE DESCRIPTION: SEQ ID NO:6:

| Ala | Glu | Pro | Lys | Ser | Cys | Asp | Lys | Thr | His | Thr | Cys | Pro | Pro | Cys |
|---|---|---|---|---|---|---|---|---|---|---|---|---|---|---|
| 1 | | | | 5 | | | | | 10 | | | | | 15 |

(2) INFORMATION FOR SEQ ID NO:7:

(i) SEQUENCE CHARACTERISTICS:
(A) LENGTH: 4 amino acids
(B) TYPE: amino acid
(D) TOPOLOGY: both (x i) SEQUENCE DESCRIPTION: SEQ ID NO:7:

| Val | Thr | Val | Ser |
|---|---|---|---|
| 1 | | | |

(2) INFORMATION FOR SEQ ID NO:8:

(i) SEQUENCE CHARACTERISTICS:
(A) LENGTH: 11 amino acids
(B) TYPE: amino acid
(D) TOPOLOGY: both (x i) SEQUENCE DESCRIPTION: SEQ ID NO:8:

| Val | Thr | Val | Ser | Ser | Asp | Lys | Thr | His | Thr | Cys |
|---|---|---|---|---|---|---|---|---|---|---|
| 1 | | | | 5 | | | | | 10 | |

(2) INFORMATION FOR SEQ ID NO:9:

(i) SEQUENCE CHARACTERISTICS:
(A) LENGTH: 14 amino acids
(B) TYPE: amino acid
(D) TOPOLOGY: both (x i) SEQUENCE DESCRIPTION: SEQ ID NO:9:

| Val | Thr | Val | Ser | Ser | Asp | Lys | Thr | His | Thr | Cys | Pro | Pro | Cys |
|---|---|---|---|---|---|---|---|---|---|---|---|---|---|
| 1 | | | | 5 | | | | | 10 | | | | |

(2) INFORMATION FOR SEQ ID NO:10:

(i) SEQUENCE CHARACTERISTICS:
(A) LENGTH: 731 base pairs
(B) TYPE: nucleic acid
(C) STRANDEDNESS: both
(D) TOPOLOGY: both (i x) FEATURE:
(A) NAME/KEY: CDS
(B) LOCATION: 1..720

(x i) SEQUENCE DESCRIPTION: SEQ ID NO:10:

| GAC | GTC | GTT | ATG | ACT | CAG | ACA | CCA | CTA | TCA | CTT | CCT | GTT | AGT | CTA | GGT | 48 |
|---|---|---|---|---|---|---|---|---|---|---|---|---|---|---|---|---|
| Asp | Val | Val | Met | Thr | Gln | Thr | Pro | Leu | Ser | Leu | Pro | Val | Ser | Leu | Gly | |
| 1 | | | | 5 | | | | | 10 | | | | | 15 | | |

| GAT | CAA | GCC | TCC | ATC | TCT | TGC | AGA | TCT | AGT | CAG | AGC | CTT | GTA | CAC | AGT | 96 |
|---|---|---|---|---|---|---|---|---|---|---|---|---|---|---|---|---|
| Asp | Gln | Ala | Ser | Ile | Ser | Cys | Arg | Ser | Ser | Gln | Ser | Leu | Val | His | Ser | |
| | | | 20 | | | | | 25 | | | | | 30 | | | |

| AAT | GGA | AAC | ACC | TAT | TTA | CGT | TGG | TAC | CTG | CAG | AAG | CCA | GGC | CAG | TCT | 144 |
|---|---|---|---|---|---|---|---|---|---|---|---|---|---|---|---|---|
| Asn | Gly | Asn | Thr | Tyr | Leu | Arg | Trp | Tyr | Leu | Gln | Lys | Pro | Gly | Gln | Ser | |
| | | 35 | | | | | 40 | | | | | 45 | | | | |

| CCA | AAG | GTC | CTG | ATC | TAC | AAA | GTT | TCC | AAC | CGA | TTT | TCT | GGG | GTC | CCA | 192 |
|---|---|---|---|---|---|---|---|---|---|---|---|---|---|---|---|---|
| Pro | Lys | Val | Leu | Ile | Tyr | Lys | Val | Ser | Asn | Arg | Phe | Ser | Gly | Val | Pro | |
| | 50 | | | | | 55 | | | | | 60 | | | | | |

| GAC | AGG | TTC | AGT | GGC | AGT | GGA | TCA | GGG | ACA | GAT | TTC | ACA | CTC | AAG | ATC | 240 |
|---|---|---|---|---|---|---|---|---|---|---|---|---|---|---|---|---|
| Asp | Arg | Phe | Ser | Gly | Ser | Gly | Ser | Gly | Thr | Asp | Phe | Thr | Leu | Lys | Ile | |
| 65 | | | | 70 | | | | | 75 | | | | | 80 | | |

```
AGC  AGA  GTG  GAG  GCT  GAG  GAT  CTG  GGA  GTT  TAT  TTC  TGC  TCT  CAA  AGT      288
Ser  Arg  Val  Glu  Ala  Glu  Asp  Leu  Gly  Val  Tyr  Phe  Cys  Ser  Gln  Ser
               85                      90                            95

ACA  CAT  GTT  CCG  TGG  ACG  TTC  GGT  GGA  GGC  ACC  AAG  CTT  GAA  ATC  AAA      336
Thr  His  Val  Pro  Trp  Thr  Phe  Gly  Gly  Gly  Thr  Lys  Leu  Glu  Ile  Lys
              100                     105                           110

GGT  TCT  ACC  TCT  GGT  TCT  GGT  AAA  TCC  TCT  GAA  GGC  AAA  GGT  CAG  GTT      384
Gly  Ser  Thr  Ser  Gly  Ser  Gly  Lys  Ser  Ser  Glu  Gly  Lys  Gly  Gln  Val
              115                     120                           125

CAG  CTG  CAG  CAG  TCT  GAC  GCT  GAG  TTG  GTG  AAA  CCT  GGG  GCT  TCA  GTG      432
Gln  Leu  Gln  Gln  Ser  Asp  Ala  Glu  Leu  Val  Lys  Pro  Gly  Ala  Ser  Val
         130                      135                           140

AAG  ATT  TCC  TGC  AAG  GCT  TCT  GGC  TAC  ACC  TTC  ACT  GAC  CAT  GCA  ATT      480
Lys  Ile  Ser  Cys  Lys  Ala  Ser  Gly  Tyr  Thr  Phe  Thr  Asp  His  Ala  Ile
145                      150                     155                          160

CAC  TGG  GTG  AAA  CAG  AAC  CCT  GAA  CAG  GGC  CTG  GAA  TGG  ATT  GGA  TAT      528
His  Trp  Val  Lys  Gln  Asn  Pro  Glu  Gln  Gly  Leu  Glu  Trp  Ile  Gly  Tyr
                    165                     170                     175

TTT  TCT  CCC  GGA  AAT  GAT  GAT  TTT  AAA  TAC  AAT  GAG  AGG  TTC  AAG  GGC      576
Phe  Ser  Pro  Gly  Asn  Asp  Asp  Phe  Lys  Tyr  Asn  Glu  Arg  Phe  Lys  Gly
              180                     185                           190

AAG  GCC  ACA  CTG  ACT  GCA  GAC  AAA  TCC  TCC  AGC  ACT  GCC  TAC  GTG  CAG      624
Lys  Ala  Thr  Leu  Thr  Ala  Asp  Lys  Ser  Ser  Ser  Thr  Ala  Tyr  Val  Gln
              195                     200                           205

CTC  AAC  AGC  CTG  ACA  TCT  GAG  GAT  TCT  GCA  GTG  TAT  TTC  TGT  ACA  AGA      672
Leu  Asn  Ser  Leu  Thr  Ser  Glu  Asp  Ser  Ala  Val  Tyr  Phe  Cys  Thr  Arg
         210                      215                           220

TCC  CTG  AAT  ATG  GCC  TAC  TGG  GGT  CAA  GGA  ACC  TCA  GTC  ACC  GTC  TCC      720
Ser  Leu  Asn  Met  Ala  Tyr  Trp  Gly  Gln  Gly  Thr  Ser  Val  Thr  Val  Ser
225                      230                     235                          240

TAATAGGATC C                                                                         731
```

( 2 ) INFORMATION FOR SEQ ID NO:11:

( i ) SEQUENCE CHARACTERISTICS:
( A ) LENGTH: 240 amino acids
( B ) TYPE: amino acid
( D ) TOPOLOGY: linear ( i i ) MOLECULE TYPE: protein ( x i ) SEQUENCE DESCRIPTION: SEQ ID NO:11:

```
Asp  Val  Val  Met  Thr  Gln  Thr  Pro  Leu  Ser  Leu  Pro  Val  Ser  Leu  Gly
 1              5                       10                          15

Asp  Gln  Ala  Ser  Ile  Ser  Cys  Arg  Ser  Gln  Ser  Leu  Val  His  Ser
              20                      25                      30

Asn  Gly  Asn  Thr  Tyr  Leu  Arg  Trp  Tyr  Leu  Gln  Lys  Pro  Gly  Gln  Ser
              35                      40                      45

Pro  Lys  Val  Leu  Ile  Tyr  Lys  Val  Ser  Asn  Arg  Phe  Ser  Gly  Val  Pro
     50                      55                      60

Asp  Arg  Phe  Ser  Gly  Ser  Gly  Ser  Gly  Thr  Asp  Phe  Thr  Leu  Lys  Ile
65                            70                      75                      80

Ser  Arg  Val  Glu  Ala  Glu  Asp  Leu  Gly  Val  Tyr  Phe  Cys  Ser  Gln  Ser
               85                      90                           95

Thr  His  Val  Pro  Trp  Thr  Phe  Gly  Gly  Gly  Thr  Lys  Leu  Glu  Ile  Lys
              100                     105                          110

Gly  Ser  Thr  Ser  Gly  Ser  Gly  Lys  Ser  Ser  Glu  Gly  Lys  Gly  Gln  Val
              115                     120                          125

Gln  Leu  Gln  Gln  Ser  Asp  Ala  Glu  Leu  Val  Lys  Pro  Gly  Ala  Ser  Val
```

|  |  |  |  |  |  |  |  |  |  |  |  |  |  |  |  |
|---|---|---|---|---|---|---|---|---|---|---|---|---|---|---|---|
|  |  |  | 130 |  |  |  |  | 135 |  |  |  |  | 140 |  |  |
| Lys | Ile | Ser | Cys | Lys | Ala | Ser | Gly | Tyr | Thr | Phe | Thr | Asp | His | Ala | Ile |
| 145 |  |  |  |  | 150 |  |  |  |  | 155 |  |  |  |  | 160 |
| His | Trp | Val | Lys | Gln | Asn | Pro | Glu | Gln | Gly | Leu | Glu | Trp | Ile | Gly | Tyr |
|  |  |  |  | 165 |  |  |  |  | 170 |  |  |  |  | 175 |  |
| Phe | Ser | Pro | Gly | Asn | Asp | Asp | Phe | Lys | Tyr | Asn | Glu | Arg | Phe | Lys | Gly |
|  |  |  | 180 |  |  |  |  | 185 |  |  |  |  | 190 |  |  |
| Lys | Ala | Thr | Leu | Thr | Ala | Asp | Lys | Ser | Ser | Ser | Thr | Ala | Tyr | Val | Gln |
|  |  | 195 |  |  |  |  | 200 |  |  |  |  | 205 |  |  |  |
| Leu | Asn | Ser | Leu | Thr | Ser | Glu | Asp | Ser | Ala | Val | Tyr | Phe | Cys | Thr | Arg |
|  | 210 |  |  |  |  | 215 |  |  |  |  | 220 |  |  |  |  |
| Ser | Leu | Asn | Met | Ala | Tyr | Trp | Gly | Gln | Gly | Thr | Ser | Val | Thr | Val | Ser |
| 225 |  |  |  |  | 230 |  |  |  |  | 235 |  |  |  |  | 240 |

(2) INFORMATION FOR SEQ ID NO:12:

(i) SEQUENCE CHARACTERISTICS:
        (A) LENGTH: 744 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 1..732

(xi) SEQUENCE DESCRIPTION: SEQ ID NO:12:

| GAC | GTC | GTG | ATG | TCA | CAG | TCT | CCA | TCC | TCC | CTA | CCT | GTG | TCA | GTT | GGC | 48 |
|---|---|---|---|---|---|---|---|---|---|---|---|---|---|---|---|---|
| Asp | Val | Val | Met | Ser | Gln | Ser | Pro | Ser | Ser | Leu | Pro | Val | Ser | Val | Gly |  |
| 1 |  |  |  | 5 |  |  |  |  | 10 |  |  |  |  | 15 |  |  |
| GAG | AAG | GTT | ACT | TTG | AGC | TGC | AAG | TCC | AGT | CAG | AGC | CTT | TTA | TAT | AGT | 96 |
| Glu | Lys | Val | Thr | Leu | Ser | Cys | Lys | Ser | Ser | Gln | Ser | Leu | Leu | Tyr | Ser |  |
|  |  |  | 20 |  |  |  |  | 25 |  |  |  |  | 30 |  |  |  |
| GGT | AAT | CAA | AAG | AAC | TAC | TTG | GCC | TGG | TAC | CAG | CAG | AAA | CCA | GGG | CAG | 144 |
| Gly | Asn | Gln | Lys | Asn | Tyr | Leu | Ala | Trp | Tyr | Gln | Gln | Lys | Pro | Gly | Gln |  |
|  |  | 35 |  |  |  |  | 40 |  |  |  |  | 45 |  |  |  |  |
| TCT | CCT | AAA | CTG | CTG | ATT | TAC | TGG | GCA | TCC | GCT | AGG | GAA | TCT | GGG | GTC | 192 |
| Ser | Pro | Lys | Leu | Leu | Ile | Tyr | Trp | Ala | Ser | Ala | Arg | Glu | Ser | Gly | Val |  |
|  | 50 |  |  |  |  | 55 |  |  |  |  | 60 |  |  |  |  |  |
| CCT | GAT | CGC | TTC | ACA | GGC | AGT | GGA | TCT | GGG | ACA | GAT | TTC | ACT | CTC | TCC | 240 |
| Pro | Asp | Arg | Phe | Thr | Gly | Ser | Gly | Ser | Gly | Thr | Asp | Phe | Thr | Leu | Ser |  |
| 65 |  |  |  |  | 70 |  |  |  |  | 75 |  |  |  |  | 80 |  |
| ATC | AGC | AGT | GTG | AAG | ACT | GAA | GAC | CTG | GCA | GTT | TAT | TAC | TGT | CAG | CAG | 288 |
| Ile | Ser | Ser | Val | Lys | Thr | Glu | Asp | Leu | Ala | Val | Tyr | Tyr | Cys | Gln | Gln |  |
|  |  |  |  | 85 |  |  |  |  | 90 |  |  |  |  | 95 |  |  |
| TAT | TAT | AGC | TAT | CCC | CTC | ACG | TTC | GGT | GCT | GGG | ACC | AAG | CTT | GTG | CTG | 336 |
| Tyr | Tyr | Ser | Tyr | Pro | Leu | Thr | Phe | Gly | Ala | Gly | Thr | Lys | Leu | Val | Leu |  |
|  |  |  | 100 |  |  |  |  | 105 |  |  |  |  | 110 |  |  |  |
| AAA | GGC | TCT | ACT | TCC | GGT | AGC | GGC | AAA | TCT | TCT | GAA | GGT | AAA | GGT | GAA | 384 |
| Lys | Gly | Ser | Thr | Ser | Gly | Ser | Gly | Lys | Ser | Ser | Glu | Gly | Lys | Gly | Glu |  |
|  |  | 115 |  |  |  |  | 120 |  |  |  |  | 125 |  |  |  |  |
| GTT | AAA | CTG | GAT | GAG | ACT | GGA | GGA | GGC | TTG | GTG | CAA | CCT | GGG | AGG | CCC | 432 |
| Val | Lys | Leu | Asp | Glu | Thr | Gly | Gly | Gly | Leu | Val | Gln | Pro | Gly | Arg | Pro |  |
|  | 130 |  |  |  |  | 135 |  |  |  |  | 140 |  |  |  |  |  |
| ATG | AAA | CTC | TCC | TGT | GTT | GCC | TCT | GGA | TTC | ACT | TTT | AGT | GAC | TAC | TGG | 480 |
| Met | Lys | Leu | Ser | Cys | Val | Ala | Ser | Gly | Phe | Thr | Phe | Ser | Asp | Tyr | Trp |  |
| 145 |  |  |  |  | 150 |  |  |  |  | 155 |  |  |  |  | 160 |  |
| ATG | AAC | TGG | GTC | CGC | CAG | TCT | CCA | GAG | AAA | GGA | CTG | GAG | TGG | GTA | GCA | 528 |
| Met | Asn | Trp | Val | Arg | Gln | Ser | Pro | Glu | Lys | Gly | Leu | Glu | Trp | Val | Ala |  |
|  |  |  |  | 165 |  |  |  |  | 170 |  |  |  |  | 175 |  |  |
| CAA | ATT | AGA | AAC | AAA | CCT | TAT | AAT | TAT | GAA | ACA | TAT | TAT | TCA | GAT | TCT | 576 |

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Gln | Ile | Arg | Asn | Lys | Pro | Tyr | Asn | Tyr | Glu | Thr | Tyr | Tyr | Ser | Asp | Ser | |
|     |     |     | 180 |     |     |     | 185 |     |     |     |     |     | 190 |     |     | |

| GTG | AAA | GGC | AGA | TTC | ACC | ATC | TCA | AGA | GAT | GAT | TCC | AAA | AGT | AGT | GTC | 624 |
|-----|-----|-----|-----|-----|-----|-----|-----|-----|-----|-----|-----|-----|-----|-----|-----|-----|
| Val | Lys | Gly | Arg | Phe | Thr | Ile | Ser | Arg | Asp | Asp | Ser | Lys | Ser | Ser | Val | |
|     |     | 195 |     |     |     |     | 200 |     |     |     |     | 205 |     |     |     | |

| TAC | CTG | CAA | ATG | AAC | AAC | TTA | AGA | GTT | GAA | GAC | ATG | GGT | ATC | TAT | TAC | 672 |
|-----|-----|-----|-----|-----|-----|-----|-----|-----|-----|-----|-----|-----|-----|-----|-----|-----|
| Tyr | Leu | Gln | Met | Asn | Asn | Leu | Arg | Val | Glu | Asp | Met | Gly | Ile | Tyr | Tyr | |
|     | 210 |     |     |     |     | 215 |     |     |     |     | 220 |     |     |     |     | |

| TGT | ACG | GGT | TCT | TAC | TAT | GGT | ATG | GAC | TAC | TGG | GGT | CAA | GGA | ACC | TCA | 720 |
|-----|-----|-----|-----|-----|-----|-----|-----|-----|-----|-----|-----|-----|-----|-----|-----|-----|
| Cys | Thr | Gly | Ser | Tyr | Tyr | Gly | Met | Asp | Tyr | Trp | Gly | Gln | Gly | Thr | Ser | |
| 225 |     |     |     | 230 |     |     |     |     | 235 |     |     |     |     | 240 |     | |

| GTC | ACC | GTC | TCC | TAATAAGGAT | CC | | | | | | | | | | | 744 |
|-----|-----|-----|-----|------------|----|--|--|--|--|--|--|--|--|--|--|-----|
| Val | Thr | Val | Ser | | | | | | | | | | | | | |

( 2 ) INFORMATION FOR SEQ ID NO:13:

( i ) SEQUENCE CHARACTERISTICS:
        ( A ) LENGTH: 244 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| Asp | Val | Val | Met | Ser | Gln | Ser | Pro | Ser | Ser | Leu | Pro | Val | Ser | Val | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Lys | Val | Thr | Leu | Ser | Cys | Lys | Ser | Ser | Gln | Ser | Leu | Leu | Tyr | Ser |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Asn | Gln | Lys | Asn | Tyr | Leu | Ala | Trp | Tyr | Gln | Gln | Lys | Pro | Gly | Gln |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Ser | Pro | Lys | Leu | Leu | Ile | Tyr | Trp | Ala | Ser | Ala | Arg | Glu | Ser | Gly | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Pro | Asp | Arg | Phe | Thr | Gly | Ser | Gly | Ser | Gly | Thr | Asp | Phe | Thr | Leu | Ser |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ile | Ser | Ser | Val | Lys | Thr | Glu | Asp | Leu | Ala | Val | Tyr | Tyr | Cys | Gln | Gln |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Tyr | Tyr | Ser | Tyr | Pro | Leu | Thr | Phe | Gly | Ala | Gly | Thr | Lys | Leu | Val | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Lys | Gly | Ser | Thr | Ser | Gly | Ser | Gly | Lys | Ser | Ser | Glu | Gly | Lys | Gly | Glu |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Val | Lys | Leu | Asp | Glu | Thr | Gly | Gly | Gly | Leu | Val | Gln | Pro | Gly | Arg | Pro |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Met | Lys | Leu | Ser | Cys | Val | Ala | Ser | Gly | Phe | Thr | Phe | Ser | Asp | Tyr | Trp |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Met | Asn | Trp | Val | Arg | Gln | Ser | Pro | Glu | Lys | Gly | Leu | Glu | Trp | Val | Ala |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gln | Ile | Arg | Asn | Lys | Pro | Tyr | Asn | Tyr | Glu | Thr | Tyr | Tyr | Ser | Asp | Ser |
|-----|-----|-----|-----|-----|-----|-----|-----|-----|-----|-----|-----|-----|-----|-----|-----|
|     |     |     | 180 |     |     |     | 185 |     |     |     |     |     | 190 |     |     |

| Val | Lys | Gly | Arg | Phe | Thr | Ile | Ser | Arg | Asp | Asp | Ser | Lys | Ser | Ser | Val |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Tyr | Leu | Gln | Met | Asn | Asn | Leu | Arg | Val | Glu | Asp | Met | Gly | Ile | Tyr | Tyr |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Cys | Thr | Gly | Ser | Tyr | Tyr | Gly | Met | Asp | Tyr | Trp | Gly | Gln | Gly | Thr | Ser |
|-----|-----|-----|-----|-----|-----|-----|-----|-----|-----|-----|-----|-----|-----|-----|-----|
| 225 |     |     |     | 230 |     |     |     |     | 235 |     |     |     |     | 240 |     |

| Val | Thr | Val | Ser |
|-----|-----|-----|-----|

( 2 ) INFORMATION FOR SEQ ID NO:14:

(i) SEQUENCE CHARACTERISTICS:
(A) LENGTH: 761 base pairs
(B) TYPE: nucleic acid
(C) STRANDEDNESS: both
(D) TOPOLOGY: both (ix) FEATURE:
(A) NAME/KEY: CDS
(B) LOCATION: 1..750

(xi) SEQUENCE DESCRIPTION: SEQ ID NO:14:

```
GAC GTC GTT ATG ACT CAG ACA CCA CTA TCA CTT CCT GTT AGT CTA GGT      48
Asp Val Val Met Thr Gln Thr Pro Leu Ser Leu Pro Val Ser Leu Gly
 1               5                  10                  15

GAT CAA GCC TCC ATC TCT TGC AGA TCT AGT CAG AGC CTT GTA CAC AGT      96
Asp Gln Ala Ser Ile Ser Cys Arg Ser Ser Gln Ser Leu Val His Ser
             20                  25                  30

AAT GGA AAC ACC TAT TTA CGT TGG TAC CTG CAG AAG CCA GGC CAG TCT     144
Asn Gly Asn Thr Tyr Leu Arg Trp Tyr Leu Gln Lys Pro Gly Gln Ser
         35                  40                  45

CCA AAG GTC CTG ATC TAC AAA GTT TCC AAC CGA TTT TCT GGG GTC CCA     192
Pro Lys Val Leu Ile Tyr Lys Val Ser Asn Arg Phe Ser Gly Val Pro
     50                  55                  60

GAC AGG TTC AGT GGC AGT GGA TCA GGG ACA GAT TTC ACA CTC AAG ATC     240
Asp Arg Phe Ser Gly Ser Gly Ser Gly Thr Asp Phe Thr Leu Lys Ile
 65                  70                  75                  80

AGC AGA GTG GAG GCT GAG GAT CTG GGA GTT TAT TTC TGC TCT CAA AGT     288
Ser Arg Val Glu Ala Glu Asp Leu Gly Val Tyr Phe Cys Ser Gln Ser
                 85                  90                  95

ACA CAT GTT CCG TGG ACG TTC GGT GGA GGC ACC AAG CTT GAA ATC AAA     336
Thr His Val Pro Trp Thr Phe Gly Gly Gly Thr Lys Leu Glu Ile Lys
             100                 105                 110

GGT TCT ACC TCT GGT TCT GGT AAA TCT TCT GAA GGT AAA GGT GAA GTT     384
Gly Ser Thr Ser Gly Ser Gly Lys Ser Ser Glu Gly Lys Gly Glu Val
         115                 120                 125

AAA CTG GAT GAG ACT GGA GGA GGC TTG GTG CAA CCT GGG AGG CCC ATG     432
Lys Leu Asp Glu Thr Gly Gly Gly Leu Val Gln Pro Gly Arg Pro Met
     130                 135                 140

AAA CTC TCC TGT GTT GCC TCT GGA TTC ACT TTT AGT GAC TAC TGG ATG     480
Lys Leu Ser Cys Val Ala Ser Gly Phe Thr Phe Ser Asp Tyr Trp Met
145                 150                 155                 160

AAC TGG GTC CGC CAG TCT CCA GAG AAA GGA CTG GAG TGG GTA GCA CAA     528
Asn Trp Val Arg Gln Ser Pro Glu Lys Gly Leu Glu Trp Val Ala Gln
                 165                 170                 175

ATT AGA AAC AAA CCT TAT AAT TAT GAA ACA TAT TAT TCA GAT TCT GTG     576
Ile Arg Asn Lys Pro Tyr Asn Tyr Glu Thr Tyr Tyr Ser Asp Ser Val
             180                 185                 190

AAA GGC AGA TTC ACC ATC TCA AGA GAT GAT TCC AAA AGT AGT GTC TAC     624
Lys Gly Arg Phe Thr Ile Ser Arg Asp Asp Ser Lys Ser Ser Val Tyr
         195                 200                 205

CTG CAA ATG AAC AAC TTA AGA GTT GAA GAC ATG GGT ATC TAT TAC TGT     672
Leu Gln Met Asn Asn Leu Arg Val Glu Asp Met Gly Ile Tyr Tyr Cys
     210                 215                 220

ACG GGT TCT TAC TAT GGT ATG GAC TAC TGG GGT CAA GGA ACC TCG GTC     720
Thr Gly Ser Tyr Tyr Gly Met Asp Tyr Trp Gly Gln Gly Thr Ser Val
225                 230                 235                 240

ACC GTC TCC AGT GAT AAG ACC CAT ACA TGC TAATAGGATC C                 761
Thr Val Ser Ser Asp Lys Thr His Thr Cys
                245                 250
```

(2) INFORMATION FOR SEQ ID NO:15:

(i) SEQUENCE CHARACTERISTICS:

(A) LENGTH: 250 amino acids
(B) TYPE: amino acid
(D) TOPOLOGY: linear (ii) MOLECULE TYPE: protein (xi) SEQUENCE DESCRIPTION: SEQ ID NO:15:

| Asp | Val | Val | Met | Thr | Gln | Thr | Pro | Leu | Ser | Leu | Pro | Val | Ser | Leu | Gly |
|---|---|---|---|---|---|---|---|---|---|---|---|---|---|---|---|
| 1 | | | | 5 | | | | | 10 | | | | | 15 | |

| Asp | Gln | Ala | Ser | Ile | Ser | Cys | Arg | Ser | Gln | Ser | Leu | Val | His | Ser |
|---|---|---|---|---|---|---|---|---|---|---|---|---|---|---|
| | | | 20 | | | | | 25 | | | | 30 | | |

| Asn | Gly | Asn | Thr | Tyr | Leu | Arg | Trp | Tyr | Leu | Gln | Lys | Pro | Gly | Gln | Ser |
|---|---|---|---|---|---|---|---|---|---|---|---|---|---|---|---|
| | | 35 | | | | | 40 | | | | | 45 | | | |

| Pro | Lys | Val | Leu | Ile | Tyr | Lys | Val | Ser | Asn | Arg | Phe | Ser | Gly | Val | Pro |
|---|---|---|---|---|---|---|---|---|---|---|---|---|---|---|---|
| | 50 | | | | | 55 | | | | | 60 | | | | |

| Asp | Arg | Phe | Ser | Gly | Ser | Gly | Ser | Gly | Thr | Asp | Phe | Thr | Leu | Lys | Ile |
|---|---|---|---|---|---|---|---|---|---|---|---|---|---|---|---|
| 65 | | | | | 70 | | | | | 75 | | | | | 80 |

| Ser | Arg | Val | Glu | Ala | Glu | Asp | Leu | Gly | Val | Tyr | Phe | Cys | Ser | Gln | Ser |
|---|---|---|---|---|---|---|---|---|---|---|---|---|---|---|---|
| | | | | 85 | | | | | 90 | | | | | 95 | |

| Thr | His | Val | Pro | Trp | Thr | Phe | Gly | Gly | Gly | Thr | Lys | Leu | Glu | Ile | Lys |
|---|---|---|---|---|---|---|---|---|---|---|---|---|---|---|---|
| | | | 100 | | | | | 105 | | | | | 110 | | |

| Gly | Ser | Thr | Ser | Gly | Ser | Gly | Lys | Ser | Ser | Glu | Gly | Lys | Gly | Glu | Val |
|---|---|---|---|---|---|---|---|---|---|---|---|---|---|---|---|
| | | 115 | | | | | 120 | | | | | 125 | | | |

| Lys | Leu | Asp | Glu | Thr | Gly | Gly | Gly | Leu | Val | Gln | Pro | Gly | Arg | Pro | Met |
|---|---|---|---|---|---|---|---|---|---|---|---|---|---|---|---|
| | 130 | | | | | 135 | | | | | 140 | | | | |

| Lys | Leu | Ser | Cys | Val | Ala | Ser | Gly | Phe | Thr | Phe | Ser | Asp | Tyr | Trp | Met |
|---|---|---|---|---|---|---|---|---|---|---|---|---|---|---|---|
| 145 | | | | | 150 | | | | | 155 | | | | | 160 |

| Asn | Trp | Val | Arg | Gln | Ser | Pro | Glu | Lys | Gly | Leu | Glu | Trp | Val | Ala | Gln |
|---|---|---|---|---|---|---|---|---|---|---|---|---|---|---|---|
| | | | | 165 | | | | | 170 | | | | | 175 | |

| Ile | Arg | Asn | Lys | Pro | Tyr | Asn | Tyr | Glu | Thr | Tyr | Tyr | Ser | Asp | Ser | Val |
|---|---|---|---|---|---|---|---|---|---|---|---|---|---|---|---|
| | | | 180 | | | | | 185 | | | | | 190 | | |

| Lys | Gly | Arg | Phe | Thr | Ile | Ser | Arg | Asp | Asp | Ser | Lys | Ser | Ser | Val | Tyr |
|---|---|---|---|---|---|---|---|---|---|---|---|---|---|---|---|
| | | 195 | | | | | 200 | | | | | 205 | | | |

| Leu | Gln | Met | Asn | Asn | Leu | Arg | Val | Glu | Asp | Met | Gly | Ile | Tyr | Tyr | Cys |
|---|---|---|---|---|---|---|---|---|---|---|---|---|---|---|---|
| | 210 | | | | | 215 | | | | | 220 | | | | |

| Thr | Gly | Ser | Tyr | Tyr | Gly | Met | Asp | Tyr | Trp | Gly | Gln | Gly | Thr | Ser | Val |
|---|---|---|---|---|---|---|---|---|---|---|---|---|---|---|---|
| 225 | | | | | 230 | | | | | 235 | | | | | 240 |

| Thr | Val | Ser | Ser | Asp | Lys | Thr | His | Thr | Cys |
|---|---|---|---|---|---|---|---|---|---|
| | | | | 245 | | | | | 250 |

(2) INFORMATION FOR SEQ ID NO:16:

(i) SEQUENCE CHARACTERISTICS:
(A) LENGTH: 770 base pairs
(B) TYPE: nucleic acid
(C) STRANDEDNESS: both
(D) TOPOLOGY: both (ix) FEATURE:
(A) NAME/KEY: CDS
(B) LOCATION: 1..759

(xi) SEQUENCE DESCRIPTION: SEQ ID NO:16:

| GAC | GTC | GTT | ATG | ACT | CAG | ACA | CCA | CTA | TCA | CTT | CCT | GTT | AGT | CTA | GGT | 48 |
|---|---|---|---|---|---|---|---|---|---|---|---|---|---|---|---|---|
| Asp | Val | Val | Met | Thr | Gln | Thr | Pro | Leu | Ser | Leu | Pro | Val | Ser | Leu | Gly | |
| 1 | | | | 5 | | | | | 10 | | | | | 15 | | |

| GAT | CAA | GCC | TCC | ATC | TCT | TGC | AGA | TCT | AGT | CAG | AGC | CTT | GTA | CAC | AGT | 96 |
|---|---|---|---|---|---|---|---|---|---|---|---|---|---|---|---|---|
| Asp | Gln | Ala | Ser | Ile | Ser | Cys | Arg | Ser | Ser | Gln | Ser | Leu | Val | His | Ser | |
| | | | 20 | | | | | 25 | | | | 30 | | | | |

| AAT | GGA | AAC | ACC | TAT | TTA | CGT | TGG | TAC | CTG | CAG | AAG | CCA | GGC | CAG | TCT | 144 |

| | | | | | | | | | | | | | | | |
|---|---|---|---|---|---|---|---|---|---|---|---|---|---|---|---|
|Asn|Gly|Asn|Thr|Tyr|Leu|Arg|Trp|Tyr|Leu|Gln|Lys|Pro|Gly|Gln|Ser|
| | |35| | | |40| | | |45| | | | | |
|CCA|AAG|GTC|CTG|ATC|TAC|AAA|GTT|TCC|AAC|CGA|TTT|TCT|GGG|GTC|CCA| 192
|Pro|Lys|Val|Leu|Ile|Tyr|Lys|Val|Ser|Asn|Arg|Phe|Ser|Gly|Val|Pro|
| |50| | | | |55| | | |60| | | | | |
|GAC|AGG|TTC|AGT|GGC|AGT|GGA|TCA|GGG|ACA|GAT|TTC|ACA|CTC|AAG|ATC| 240
|Asp|Arg|Phe|Ser|Gly|Ser|Gly|Ser|Gly|Thr|Asp|Phe|Thr|Leu|Lys|Ile|
|65| | | | |70| | | | |75| | | | |80|
|AGC|AGA|GTG|GAG|GCT|GAG|GAT|CTG|GGA|GTT|TAT|TTC|TGC|TCT|CAA|AGT| 288
|Ser|Arg|Val|Glu|Ala|Glu|Asp|Leu|Gly|Val|Tyr|Phe|Cys|Ser|Gln|Ser|
| | | | |85| | | | |90| | | | |95| |
|ACA|CAT|GTT|CCG|TGG|ACG|TTC|GGT|GGA|GGC|ACC|AAG|CTT|GAA|ATC|AAA| 336
|Thr|His|Val|Pro|Trp|Thr|Phe|Gly|Gly|Gly|Thr|Lys|Leu|Glu|Ile|Lys|
| | | |100| | | |105| | | |110| | | | |
|GGT|TCT|ACC|TCT|GGT|TCT|GGT|AAA|TCT|TCT|GAA|GGT|AAA|GGT|GAA|GTT| 384
|Gly|Ser|Thr|Ser|Gly|Ser|Gly|Lys|Ser|Ser|Glu|Gly|Lys|Gly|Glu|Val|
| | |115| | | |120| | | |125| | | | | |
|AAA|CTG|GAT|GAG|ACT|GGA|GGA|GGC|TTG|GTG|CAA|CCT|GGG|AGG|CCC|ATG| 432
|Lys|Leu|Asp|Glu|Thr|Gly|Gly|Gly|Leu|Val|Gln|Pro|Gly|Arg|Pro|Met|
| |130| | | |135| | | | |140| | | | | |
|AAA|CTC|TCC|TGT|GTT|GCC|TCT|GGA|TTC|ACT|TTT|AGT|GAC|TAC|TGG|ATG| 480
|Lys|Leu|Ser|Cys|Val|Ala|Ser|Gly|Phe|Thr|Phe|Ser|Asp|Tyr|Trp|Met|
|145| | | | |150| | | | |155| | | | |160|
|AAC|TGG|GTC|CGC|CAG|TCT|CCA|GAG|AAA|GGA|CTG|GAG|TGG|GTA|GCA|CAA| 528
|Asn|Trp|Val|Arg|Gln|Ser|Pro|Glu|Lys|Gly|Leu|Glu|Trp|Val|Ala|Gln|
| | | | |165| | | | |170| | | | |175| |
|ATT|AGA|AAC|AAA|CCT|TAT|AAT|TAT|GAA|ACA|TAT|TAT|TCA|GAT|TCT|GTG| 576
|Ile|Arg|Asn|Lys|Pro|Tyr|Asn|Tyr|Glu|Thr|Tyr|Tyr|Ser|Asp|Ser|Val|
| | | |180| | | |185| | | | |190| | | |
|AAA|GGC|AGA|TTC|ACC|ATC|TCA|AGA|GAT|GAT|TCC|AAA|AGT|AGT|GTC|TAC| 624
|Lys|Gly|Arg|Phe|Thr|Ile|Ser|Arg|Asp|Asp|Ser|Lys|Ser|Ser|Val|Tyr|
| | |195| | | | |200| | | |205| | | | |
|CTG|CAA|ATG|AAC|AAC|TTA|AGA|GTT|GAA|GAC|ATG|GGT|ATC|TAT|TAC|TGT| 672
|Leu|Gln|Met|Asn|Asn|Leu|Arg|Val|Glu|Asp|Met|Gly|Ile|Tyr|Tyr|Cys|
| |210| | | | |215| | | | |220| | | | |
|ACG|GGT|TCT|TAC|TAT|GGT|ATG|GAC|TAC|TGG|GGT|CAA|GGA|ACC|TCG|GTC| 720
|Thr|Gly|Ser|Tyr|Tyr|Gly|Met|Asp|Tyr|Trp|Gly|Gln|Gly|Thr|Ser|Val|
|225| | | | |230| | | | |235| | | | |240|
|ACC|GTC|TCC|AGT|GAT|AAG|ACC|CAT|ACA|TGC|CCT|CCA|TGC|TAATAGGATC|C| | 770
|Thr|Val|Ser|Ser|Asp|Lys|Thr|His|Thr|Cys|Pro|Pro|Cys| | | |
| | | | |245| | | | |250| | | | | | |

( 2 ) INFORMATION FOR SEQ ID NO:17:

( i ) SEQUENCE CHARACTERISTICS:
        ( A ) LENGTH: 253 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| | | | | | | | | | | | | | | | |
|---|---|---|---|---|---|---|---|---|---|---|---|---|---|---|---|
|Asp|Val|Val|Met|Thr|Gln|Thr|Pro|Leu|Ser|Leu|Pro|Val|Ser|Leu|Gly|
|1| | | |5| | | | |10| | | | |15| |
|Asp|Gln|Ala|Ser|Ile|Ser|Cys|Arg|Ser|Gln|Ser|Leu|Val|His|Ser|
| | | |20| | | | |25| | | | |30| | |
|Asn|Gly|Asn|Thr|Tyr|Leu|Arg|Trp|Tyr|Leu|Gln|Lys|Pro|Gly|Gln|Ser|
| | |35| | | |40| | | |45| | | | | |
|Pro|Lys|Val|Leu|Ile|Tyr|Lys|Val|Ser|Asn|Arg|Phe|Ser|Gly|Val|Pro|
| |50| | | | |55| | | |60| | | | | |
|Asp|Arg|Phe|Ser|Gly|Ser|Gly|Ser|Gly|Thr|Asp|Phe|Thr|Leu|Lys|Ile|

|    |    |    |    | 65  |    |    |    |    | 70  |    |    |    |    | 75  |    |    |    |    | 80  |
|----|----|----|----|-----|----|----|----|----|-----|----|----|----|----|-----|----|----|----|----|-----|

Ser Arg Val Glu Ala Glu Asp Leu Gly Val Tyr Phe Cys Ser Gln Ser
                    85                      90                       95

Thr His Val Pro Trp Thr Phe Gly Gly Gly Thr Lys Leu Glu Ile Lys
                100                     105                     110

Gly Ser Thr Ser Gly Ser Gly Lys Ser Ser Glu Gly Lys Gly Glu Val
                115                     120                     125

Lys Leu Asp Glu Thr Gly Gly Gly Leu Val Gln Pro Gly Arg Pro Met
        130                     135                     140

Lys Leu Ser Cys Val Ala Ser Gly Phe Thr Phe Ser Asp Tyr Trp Met
145                     150                     155                     160

Asn Trp Val Arg Gln Ser Pro Glu Lys Gly Leu Glu Trp Val Ala Gln
                165                     170                     175

Ile Arg Asn Lys Pro Tyr Asn Tyr Glu Thr Tyr Tyr Ser Asp Ser Val
                180                     185                     190

Lys Gly Arg Phe Thr Ile Ser Arg Asp Asp Ser Lys Ser Ser Val Tyr
                195                     200                     205

Leu Gln Met Asn Asn Leu Arg Val Glu Asp Met Gly Ile Tyr Tyr Cys
        210                     215                     220

Thr Gly Ser Tyr Tyr Gly Met Asp Tyr Trp Gly Gln Gly Thr Ser Val
225                     230                     235                     240

Thr Val Ser Ser Asp Lys Thr His Thr Cys Pro Pro Cys
                245                     250

( 2 ) INFORMATION FOR SEQ ID NO:18:

( i ) SEQUENCE CHARACTERISTICS:
        ( A ) LENGTH: 1460 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 1..1449

( x i ) SEQUENCE DESCRIPTION: SEQ ID NO:18:

GAC GTC GTG ATG TCA CAG TCT CCA TCC TCC CTA CCT GTG TCA GTT GGC    48
Asp Val Val Met Ser Gln Ser Pro Ser Ser Leu Pro Val Ser Val Gly
 1               5                  10                  15

GAG AAG GTT ACT TTG AGC TGC AAG TCC AGT CAG AGC CTT TTA TAT AGT    96
Glu Lys Val Thr Leu Ser Cys Lys Ser Ser Gln Ser Leu Leu Tyr Ser
                20                  25                  30

GGT AAT CAA AAG AAC TAC TTG GCC TGG TAC CAG CAG AAA CCA GGG CAG   144
Gly Asn Gln Lys Asn Tyr Leu Ala Trp Tyr Gln Gln Lys Pro Gly Gln
            35                  40                  45

TCT CCT AAA CTG CTG ATT TAC TGG GCA TCC GCT AGG GAA TCT GGG GTC   192
Ser Pro Lys Leu Leu Ile Tyr Trp Ala Ser Ala Arg Glu Ser Gly Val
        50                  55                  60

CCT GAT CGC TTC ACA GGC AGT GGA TCT GGG ACA GAT TTC ACT CTC TCC   240
Pro Asp Arg Phe Thr Gly Ser Gly Ser Gly Thr Asp Phe Thr Leu Ser
65                  70                  75                  80

ATC AGC AGT GTG AAG ACT GAA GAC CTG GCA GTT TAT TAC TGT CAG CAG   288
Ile Ser Ser Val Lys Thr Glu Asp Leu Ala Val Tyr Tyr Cys Gln Gln
                85                  90                  95

TAT TAT AGC TAT CCC CTC ACG TTC GGT GCT GGG ACC AAG CTT GTG CTG   336
Tyr Tyr Ser Tyr Pro Leu Thr Phe Gly Ala Gly Thr Lys Leu Val Leu
                100                 105                 110

AAA GGC TCT ACT TCC GGT AGC GGC AAA TCC TCT GAA GGC AAA GGT CAG   384
Lys Gly Ser Thr Ser Gly Ser Gly Lys Ser Ser Glu Gly Lys Gly Gln

```
                    115                           120                              125
GTT  CAG  CTG  CAG  CAG  TCT  GAC  GCT  GAG  TTG  GTG  AAA  CCT  GGG  GCT  TCA           432
Val  Gln  Leu  Gln  Gln  Ser  Asp  Ala  Glu  Leu  Val  Lys  Pro  Gly  Ala  Ser
130                      135                     140

GTG  AAG  ATT  TCC  TGC  AAG  GCT  TCT  GGC  TAC  ACC  TTC  ACT  GAC  CAT  GCA           480
Val  Lys  Ile  Ser  Cys  Lys  Ala  Ser  Gly  Tyr  Thr  Phe  Thr  Asp  His  Ala
145                      150                     155                          160

ATT  CAC  TGG  GTG  AAA  CAG  AAC  CCT  GAA  CAG  GGC  CTG  GAA  TGG  ATT  GGA           528
Ile  His  Trp  Val  Lys  Gln  Asn  Pro  Glu  Gln  Gly  Leu  Glu  Trp  Ile  Gly
                    165                     170                          175

TAT  TTT  TCT  CCC  GGA  AAT  GAT  GAT  TTT  AAA  TAC  AAT  GAG  AGG  TTC  AAG           576
Tyr  Phe  Ser  Pro  Gly  Asn  Asp  Asp  Phe  Lys  Tyr  Asn  Glu  Arg  Phe  Lys
               180                     185                     190

GGC  AAG  GCC  ACA  CTG  ACT  GCA  GAC  AAA  TCC  TCC  AGC  ACT  GCC  TAC  GTG           624
Gly  Lys  Ala  Thr  Leu  Thr  Ala  Asp  Lys  Ser  Ser  Ser  Thr  Ala  Tyr  Val
               195                     200                     205

CAG  CTC  AAC  AGC  CTG  ACA  TCT  GAG  GAT  TCT  GCA  GTG  TAT  TTC  TGT  ACA           672
Gln  Leu  Asn  Ser  Leu  Thr  Ser  Glu  Asp  Ser  Ala  Val  Tyr  Phe  Cys  Thr
               210                     215                     220

AGA  TCC  CTG  AAT  ATG  GCC  TAC  TGG  GGT  CAA  GGA  ACC  TCA  GTC  ACC  GTC           720
Arg  Ser  Leu  Asn  Met  Ala  Tyr  Trp  Gly  Gln  Gly  Thr  Ser  Val  Thr  Val
225                      230                     235                          240

TCC  TCA  GAC  GTC  GTG  ATG  TCA  CAG  TCT  CCA  TCC  TCC  CTA  CCT  GTG  TCA           768
Ser  Ser  Asp  Val  Val  Met  Ser  Gln  Ser  Pro  Ser  Ser  Leu  Pro  Val  Ser
                    245                     250                          255

GTT  GGC  GAG  AAG  GTT  ACT  TTG  AGC  TGC  AAG  TCA  AGT  CAG  AGC  CTT  TTA           816
Val  Gly  Glu  Lys  Val  Thr  Leu  Ser  Cys  Lys  Ser  Ser  Gln  Ser  Leu  Leu
               260                     265                     270

TAT  AGT  GGT  AAT  CAA  AAG  AAC  TAC  TTG  GCC  TGG  TAC  CAG  CAG  AAA  CCA           864
Tyr  Ser  Gly  Asn  Gln  Lys  Asn  Tyr  Leu  Ala  Trp  Tyr  Gln  Gln  Lys  Pro
               275                     280                     285

GGG  CAG  TCT  CCT  AAA  CTG  CTG  ATT  TAC  TGG  GCA  TCC  GCT  AGG  GAA  TCT           912
Gly  Gln  Ser  Pro  Lys  Leu  Leu  Ile  Tyr  Trp  Ala  Ser  Ala  Arg  Glu  Ser
               290                     295                     300

GGG  GTC  CCT  GAT  CGC  TTC  ACA  GGC  AGT  GGA  TCT  GGG  ACA  GAT  TTC  ACT           960
Gly  Val  Pro  Asp  Arg  Phe  Thr  Gly  Ser  Gly  Ser  Gly  Thr  Asp  Phe  Thr
305                      310                     315                          320

CTC  TCC  ATC  AGC  AGT  GTG  AAG  ACT  GAA  GAC  CTG  GCA  GTT  TAT  TAC  TGT          1008
Leu  Ser  Ile  Ser  Ser  Val  Lys  Thr  Glu  Asp  Leu  Ala  Val  Tyr  Tyr  Cys
                    325                     330                          335

CAG  CAG  TAT  TAT  AGC  TAT  CCC  CTC  ACG  TTC  GGT  GCT  GGG  ACC  AAG  CTT          1056
Gln  Gln  Tyr  Tyr  Ser  Tyr  Pro  Leu  Thr  Phe  Gly  Ala  Gly  Thr  Lys  Leu
               340                     345                     350

GTG  CTG  AAA  GGC  TCT  ACT  TCC  GGT  AGC  GGC  AAA  TCC  TCT  GAA  GGC  AAA          1104
Val  Leu  Lys  Gly  Ser  Thr  Ser  Gly  Ser  Gly  Lys  Ser  Ser  Glu  Gly  Lys
               355                     360                     365

GGT  CAG  GTT  CAG  CTG  CAG  CAG  TCT  GAC  GCT  GAG  TTG  GTG  AAA  CCT  GGG          1152
Gly  Gln  Val  Gln  Leu  Gln  Gln  Ser  Asp  Ala  Glu  Leu  Val  Lys  Pro  Gly
370                      375                     380

GCT  TCA  GTG  AAG  ATT  TCC  TGC  AAG  GCT  TCT  GGC  TAC  ACC  TTC  ACT  GAC          1200
Ala  Ser  Val  Lys  Ile  Ser  Cys  Lys  Ala  Ser  Gly  Tyr  Thr  Phe  Thr  Asp
385                      390                     395                          400

CAT  GCA  ATT  CAC  TGG  GTG  AAA  CAG  AAC  CCT  GAA  CAG  GGC  CTG  GAA  TGG          1248
His  Ala  Ile  His  Trp  Val  Lys  Gln  Asn  Pro  Glu  Gln  Gly  Leu  Glu  Trp
                    405                     410                          415

ATT  GGA  TAT  TTT  TCT  CCC  GGA  AAT  GAT  GAT  TTT  AAA  TAC  AAT  GAG  AGG          1296
Ile  Gly  Tyr  Phe  Ser  Pro  Gly  Asn  Asp  Asp  Phe  Lys  Tyr  Asn  Glu  Arg
               420                     425                     430

TTC  AAG  GGC  AAG  GCC  ACA  CTG  ACT  GCA  GAC  AAA  TCC  TCC  AGC  ACT  GCC          1344
Phe  Lys  Gly  Lys  Ala  Thr  Leu  Thr  Ala  Asp  Lys  Ser  Ser  Ser  Thr  Ala
```

|     | 435 |     |     |     | 440 |     |     |     | 445 |     |     |     |     |      |
| --- | --- | --- | --- | --- | --- | --- | --- | --- | --- | --- | --- | --- | --- | ---- |
| TAC | GTG | CAG | CTC | AAC | AGC | CTG | ACA | TCT | GAG | GAT | TCT | GCA | GTG | TAT | TTC  | 1392 |
| Tyr | Val | Gln | Leu | Asn | Ser | Leu | Thr | Ser | Glu | Asp | Ser | Ala | Val | Tyr | Phe  |
|     | 450 |     |     |     | 455 |     |     |     |     | 460 |     |     |     |     |      |

| TGT | ACA | AGA | TCC | CTG | AAT | ATG | GCC | TAC | TGG | GGT | CAA | GGA | ACC | TCA | GTC | 1440 |
| Cys | Thr | Arg | Ser | Leu | Asn | Met | Ala | Tyr | Trp | Gly | Gln | Gly | Thr | Ser | Val |
| 465 |     |     |     |     | 470 |     |     |     | 475 |     |     |     |     |     | 480 |

ACC GTC TCC TAATAGGATC C   1460
Thr Val Ser ( 2 ) INFORMATION FOR SEQ ID NO:19:

( i ) SEQUENCE CHARACTERISTICS:
        ( A ) LENGTH: 483 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Asp Val Val Met Ser Gln Ser Pro Ser Ser Leu Pro Val Ser Val Gly
 1               5                  10                  15

Glu Lys Val Thr Leu Ser Cys Lys Ser Gln Ser Leu Leu Tyr Ser
                 20                  25                  30

Gly Asn Gln Lys Asn Tyr Leu Ala Trp Tyr Gln Lys Pro Gly Gln
             35                  40                  45

Ser Pro Lys Leu Leu Ile Tyr Trp Ala Ser Ala Arg Glu Ser Gly Val
         50                  55                  60

Pro Asp Arg Phe Thr Gly Ser Gly Ser Gly Thr Asp Phe Thr Leu Ser
 65                  70                  75                  80

Ile Ser Ser Val Lys Thr Glu Asp Leu Ala Val Tyr Tyr Cys Gln Gln
                 85                  90                  95

Tyr Tyr Ser Tyr Pro Leu Thr Phe Gly Ala Gly Thr Lys Leu Val Leu
                100                 105                 110

Lys Gly Ser Thr Ser Gly Ser Gly Lys Ser Ser Glu Gly Lys Gly Gln
             115                 120                 125

Val Gln Leu Gln Gln Ser Asp Ala Glu Leu Val Lys Pro Gly Ala Ser
130                 135                 140

Val Lys Ile Ser Cys Lys Ala Ser Gly Tyr Thr Phe Thr Asp His Ala
145                 150                 155                 160

Ile His Trp Val Lys Gln Asn Pro Glu Gln Gly Leu Glu Trp Ile Gly
                165                 170                 175

Tyr Phe Ser Pro Gly Asn Asp Asp Phe Lys Tyr Asn Glu Arg Phe Lys
                180                 185                 190

Gly Lys Ala Thr Leu Thr Ala Asp Lys Ser Ser Ser Thr Ala Tyr Val
             195                 200                 205

Gln Leu Asn Ser Leu Thr Ser Glu Asp Ser Ala Val Tyr Phe Cys Thr
         210                 215                 220

Arg Ser Leu Asn Met Ala Tyr Trp Gly Gln Gly Thr Ser Val Thr Val
225                 230                 235                 240

Ser Ser Asp Val Val Met Ser Gln Ser Pro Ser Ser Leu Pro Val Ser
                245                 250                 255

Val Gly Glu Lys Val Thr Leu Ser Cys Lys Ser Ser Gln Ser Leu Leu
             260                 265                 270

Tyr Ser Gly Asn Gln Lys Asn Tyr Leu Ala Trp Tyr Gln Gln Lys Pro
         275                 280                 285

Gly Gln Ser Pro Lys Leu Leu Ile Tyr Trp Ala Ser Ala Arg Glu Ser
```

|     |     |     | 290 |     |     |     | 295 |     |     |     | 300 |     |     |     |
| --- | --- | --- | --- | --- | --- | --- | --- | --- | --- | --- | --- | --- | --- | --- |
| Gly<br>305 | Val | Pro | Asp | Arg | Phe<br>310 | Thr | Gly | Ser | Gly<br>315 | Ser | Gly | Thr | Asp | Phe<br>320 |
| Leu | Ser | Ile | Ser | Ser<br>325 | Val | Lys | Thr | Glu<br>330 | Asp | Leu | Ala | Val | Tyr | Tyr<br>335 | Cys |
| Gln | Gln | Tyr | Tyr<br>340 | Ser | Tyr | Pro | Leu | Thr<br>345 | Phe | Gly | Ala | Gly | Thr<br>350 | Lys | Leu |
| Val | Leu | Lys<br>355 | Gly | Ser | Thr | Ser | Gly<br>360 | Ser | Gly | Lys | Ser | Ser<br>365 | Glu | Gly | Lys |
| Gly | Gln<br>370 | Val | Gln | Leu | Gln | Gln<br>375 | Ser | Asp | Ala | Glu | Leu<br>380 | Val | Lys | Pro | Gly |
| Ala<br>385 | Ser | Val | Lys | Ile | Ser<br>390 | Cys | Lys | Ala | Ser | Gly<br>395 | Tyr | Thr | Phe | Thr | Asp<br>400 |
| His | Ala | Ile | His | Trp<br>405 | Val | Lys | Gln | Asn | Pro<br>410 | Glu | Gln | Gly | Leu | Glu<br>415 | Trp |
| Ile | Gly | Tyr | Phe<br>420 | Ser | Pro | Gly | Asn | Asp<br>425 | Asp | Phe | Lys | Tyr | Asn<br>430 | Glu | Arg |
| Phe | Lys | Gly<br>435 | Lys | Ala | Thr | Leu | Thr<br>440 | Ala | Asp | Lys | Ser | Ser<br>445 | Ser | Thr | Ala |
| Tyr | Val<br>450 | Gln | Leu | Asn | Ser | Leu<br>455 | Thr | Ser | Glu | Asp | Ser<br>460 | Ala | Val | Tyr | Phe |
| Cys<br>465 | Thr | Arg | Ser | Leu | Asn<br>470 | Met | Ala | Tyr | Trp | Gly<br>475 | Gln | Gly | Thr | Ser | Val<br>480 |
| Thr | Val | Ser |

(2) INFORMATION FOR SEQ ID NO:20:

(i) SEQUENCE CHARACTERISTICS:
        (A) LENGTH: 725 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 1..714

(xi) SEQUENCE DESCRIPTION: SEQ ID NO:20:

| GAC | GTC | GTT | ATG | ACT | CAG | ACA | CCA | CTA | TCA | CTT | CCT | GTT | AGT | CTA | GGT | 48 |
| --- | --- | --- | --- | --- | --- | --- | --- | --- | --- | --- | --- | --- | --- | --- | --- | --- |
| Asp<br>1 | Val | Val | Met | Thr<br>5 | Gln | Thr | Pro | Leu | Ser<br>10 | Leu | Pro | Val | Ser | Leu<br>15 | Gly |
| GAT | CAA | GCC | TCC | ATC | TCT | TGC | AGA | TCT | AGT | CAG | AGC | CTT | GTA | CAC | AGT | 96 |
| Asp | Gln | Ala | Ser<br>20 | Ile | Ser | Cys | Arg | Ser<br>25 | Ser | Gln | Ser | Leu | Val<br>30 | His | Ser |
| AAT | GGA | AAC | ACC | TAT | TTA | CGT | TGG | TAC | CTG | CAG | AAG | CCA | GGC | CAG | TCT | 144 |
| Asn | Gly | Asn<br>35 | Thr | Tyr | Leu | Arg | Trp<br>40 | Tyr | Leu | Gln | Lys | Pro<br>45 | Gly | Gln | Ser |
| CCA | AAG | GTC | CTG | ATC | TAC | AAA | GTT | TCC | AAC | CGA | TTT | TCT | GGG | GTC | CCA | 192 |
| Pro | Lys<br>50 | Val | Leu | Ile | Tyr | Lys<br>55 | Val | Ser | Asn | Arg | Phe<br>60 | Ser | Gly | Val | Pro |
| GAC | AGG | TTC | AGT | GGC | AGT | GGA | TCA | GGG | ACA | GAT | TTC | ACA | CTC | AAG | ATC | 240 |
| Asp<br>65 | Arg | Phe | Ser | Gly | Ser<br>70 | Gly | Ser | Gly | Thr | Asp<br>75 | Phe | Thr | Leu | Lys | Ile<br>80 |
| AGC | AGA | GTG | GAG | GCT | GAG | GAT | CTG | GGA | GTT | TAT | TTC | TGC | TCT | CAA | AGT | 288 |
| Ser | Arg | Val | Glu | Ala<br>85 | Glu | Asp | Leu | Gly | Val<br>90 | Tyr | Phe | Cys | Ser | Gln<br>95 | Ser |
| ACA | CAT | GTT | CCG | TGG | ACG | TTC | GGT | GGA | GGC | ACC | AAG | CTT | GAA | ATC | AAA | 336 |
| Thr | His | Val | Pro<br>100 | Trp | Thr | Phe | Gly | Gly<br>105 | Gly | Thr | Lys | Leu | Glu<br>110 | Ile | Lys |

| GGT | TCT | ACC | TCT | GGT | AAA | CCA | TCT | GAA | GGC | AAA | GGT | CAG | GTT | CAG | CTG | 384 |
| Gly | Ser | Thr | Ser | Gly | Lys | Pro | Ser | Glu | Gly | Lys | Gly | Gln | Val | Gln | Leu | |
| | | 115 | | | | | 120 | | | | | 125 | | | | |

| CAG | CAG | TCT | GAC | GCT | GAG | TTG | GTG | AAA | CCT | GGG | GCT | TCA | GTG | AAG | ATT | 432 |
| Gln | Gln | Ser | Asp | Ala | Glu | Leu | Val | Lys | Pro | Gly | Ala | Ser | Val | Lys | Ile | |
| 130 | | | | | 135 | | | | | | 140 | | | | | |

| TCC | TGC | AAG | GCT | TCT | GGC | TAC | ACC | TTC | ACT | GAC | CAT | GCA | ATT | CAC | TGG | 480 |
| Ser | Cys | Lys | Ala | Ser | Gly | Tyr | Thr | Phe | Thr | Asp | His | Ala | Ile | His | Trp | |
| 145 | | | | | 150 | | | | | 155 | | | | | 160 | |

| GTG | AAA | CAG | AAC | CCT | GAA | CAG | GGC | CTG | GAA | TGG | ATT | GGA | TAT | TTT | TCT | 528 |
| Val | Lys | Gln | Asn | Pro | Glu | Gln | Gly | Leu | Glu | Trp | Ile | Gly | Tyr | Phe | Ser | |
| | | | | 165 | | | | | 170 | | | | | 175 | | |

| CCC | GGA | AAT | GAT | GAT | TTT | AAA | TAC | AAT | GAG | AGG | TTC | AAG | GGC | AAG | GCC | 576 |
| Pro | Gly | Asn | Asp | Asp | Phe | Lys | Tyr | Asn | Glu | Arg | Phe | Lys | Gly | Lys | Ala | |
| | | | 180 | | | | | 185 | | | | | 190 | | | |

| ACA | CTG | ACT | GCA | GAC | AAA | TCC | TCC | AGC | ACT | GCC | TAC | GTG | CAG | CTC | AAC | 624 |
| Thr | Leu | Thr | Ala | Asp | Lys | Ser | Ser | Ser | Thr | Ala | Tyr | Val | Gln | Leu | Asn | |
| | | 195 | | | | | 200 | | | | | 205 | | | | |

| AGC | CTG | ACA | TCT | GAG | GAT | TCT | GCA | GTG | TAT | TTC | TGT | ACA | AGA | TCC | CTG | 672 |
| Ser | Leu | Thr | Ser | Glu | Asp | Ser | Ala | Val | Tyr | Phe | Cys | Thr | Arg | Ser | Leu | |
| | | 210 | | | | | 215 | | | | | 220 | | | | |

| AAT | ATG | GCC | TAC | TGG | GGT | CAA | GGA | ACC | TCA | GTC | ACC | GTC | TCC | TAATAGGATC | | 724 |
| Asn | Met | Ala | Tyr | Trp | Gly | Gln | Gly | Thr | Ser | Val | Thr | Val | Ser | | | |
| 225 | | | | | 230 | | | | | 235 | | | | | | |

| C | | | | | | | | | | | | | | | | 725 |

( 2 ) INFORMATION FOR SEQ ID NO:21:

( i ) SEQUENCE CHARACTERISTICS:
        ( A ) LENGTH: 238 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| Asp | Val | Val | Met | Thr | Gln | Thr | Pro | Leu | Ser | Leu | Pro | Val | Ser | Leu | Gly |
| 1 | | | | 5 | | | | | 10 | | | | | 15 | |

| Asp | Gln | Ala | Ser | Ile | Ser | Cys | Arg | Ser | Gln | Ser | Leu | Val | His | Ser |
| | | | 20 | | | | 25 | | | | | 30 | | |

| Asn | Gly | Asn | Thr | Tyr | Leu | Arg | Trp | Tyr | Leu | Gln | Lys | Pro | Gly | Gln | Ser |
| | | 35 | | | | | 40 | | | | | 45 | | | |

| Pro | Lys | Val | Leu | Ile | Tyr | Lys | Val | Ser | Asn | Arg | Phe | Ser | Gly | Val | Pro |
| | 50 | | | | | 55 | | | | | 60 | | | | |

| Asp | Arg | Phe | Ser | Gly | Ser | Gly | Ser | Gly | Thr | Asp | Phe | Thr | Leu | Lys | Ile |
| 65 | | | | | 70 | | | | | 75 | | | | | 80 |

| Ser | Arg | Val | Glu | Ala | Glu | Asp | Leu | Gly | Val | Tyr | Phe | Cys | Ser | Gln | Ser |
| | | | | 85 | | | | | 90 | | | | | 95 | |

| Thr | His | Val | Pro | Trp | Thr | Phe | Gly | Gly | Gly | Thr | Lys | Leu | Glu | Ile | Lys |
| | | | 100 | | | | | 105 | | | | | 110 | | |

| Gly | Ser | Thr | Ser | Gly | Lys | Pro | Ser | Glu | Gly | Lys | Gly | Gln | Val | Gln | Leu |
| | | 115 | | | | | 120 | | | | | 125 | | | |

| Gln | Gln | Ser | Asp | Ala | Glu | Leu | Val | Lys | Pro | Gly | Ala | Ser | Val | Lys | Ile |
| 130 | | | | | 135 | | | | | | 140 | | | | |

| Ser | Cys | Lys | Ala | Ser | Gly | Tyr | Thr | Phe | Thr | Asp | His | Ala | Ile | His | Trp |
| 145 | | | | | 150 | | | | | 155 | | | | | 160 |

| Val | Lys | Gln | Asn | Pro | Glu | Gln | Gly | Leu | Glu | Trp | Ile | Gly | Tyr | Phe | Ser |
| | | | | 165 | | | | | 170 | | | | | 175 | |

| Pro | Gly | Asn | Asp | Asp | Phe | Lys | Tyr | Asn | Glu | Arg | Phe | Lys | Gly | Lys | Ala |

|     |     |     |     |     |     | 180 |     |     |     |     |     | 185 |     |     |     |     |     | 190 |     |     |
|-----|-----|-----|-----|-----|-----|-----|-----|-----|-----|-----|-----|-----|-----|-----|-----|-----|-----|-----|-----|-----|
| Thr | Leu | Thr | Ala | Asp | Lys | Ser | Ser | Ser | Thr | Ala | Tyr | Val | Gln | Leu | Asn |
|     |     | 195 |     |     |     |     | 200 |     |     |     |     | 205 |     |     |     |

| Ser | Leu | Thr | Ser | Glu | Asp | Ser | Ala | Val | Tyr | Phe | Cys | Thr | Arg | Ser | Leu |
|-----|-----|-----|-----|-----|-----|-----|-----|-----|-----|-----|-----|-----|-----|-----|-----|
|     |     | 210 |     |     |     |     | 215 |     |     |     |     | 220 |     |     |     |

| Asn | Met | Ala | Tyr | Trp | Gly | Gln | Gly | Thr | Ser | Val | Thr | Val | Ser |
|-----|-----|-----|-----|-----|-----|-----|-----|-----|-----|-----|-----|-----|-----|
| 225 |     |     |     |     | 230 |     |     |     |     | 235 |     |     |     |

( 2 ) INFORMATION FOR SEQ ID NO:22:

( i ) SEQUENCE CHARACTERISTICS:
        ( A ) LENGTH: 738 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 1..726

( x i ) SEQUENCE DESCRIPTION: SEQ ID NO:22:

| GAC | GTC | GTG | ATG | TCA | CAG | TCT | CCA | TCC | TCC | CTA | CCT | GTG | TCA | GTT | GGC | 48 |
|-----|-----|-----|-----|-----|-----|-----|-----|-----|-----|-----|-----|-----|-----|-----|-----|----|
| Asp | Val | Val | Met | Ser | Gln | Ser | Pro | Ser | Ser | Leu | Pro | Val | Ser | Val | Gly |    |
| 1   |     |     |     | 5   |     |     |     |     | 10  |     |     |     |     | 15  |     |    |

| GAG | AAG | GTT | ACT | TTG | AGC | TGC | AAG | TCC | AGT | CAG | AGC | CTT | TTA | TAT | AGT | 96 |
| Glu | Lys | Val | Thr | Leu | Ser | Cys | Lys | Ser | Ser | Gln | Ser | Leu | Leu | Tyr | Ser |    |
|     |     |     | 20  |     |     |     |     | 25  |     |     |     |     | 30  |     |     |    |

| GGT | AAT | CAA | AAG | AAC | TAC | TTG | GCC | TGG | TAC | CAG | CAG | AAA | CCA | GGG | CAG | 144 |
| Gly | Asn | Gln | Lys | Asn | Tyr | Leu | Ala | Trp | Tyr | Gln | Gln | Lys | Pro | Gly | Gln |     |
|     |     | 35  |     |     |     |     | 40  |     |     |     |     | 45  |     |     |     |     |

| TCT | CCT | AAA | CTG | CTG | ATT | TAC | TGG | GCA | TCC | GCT | AGG | GAA | TCT | GGG | GTC | 192 |
| Ser | Pro | Lys | Leu | Leu | Ile | Tyr | Trp | Ala | Ser | Ala | Arg | Glu | Ser | Gly | Val |     |
|     |     | 50  |     |     |     |     | 55  |     |     |     |     | 60  |     |     |     |     |

| CCT | GAT | CGC | TTC | ACA | GGC | AGT | GGA | TCT | GGG | ACA | GAT | TTC | ACT | CTC | TCC | 240 |
| Pro | Asp | Arg | Phe | Thr | Gly | Ser | Gly | Ser | Gly | Thr | Asp | Phe | Thr | Leu | Ser |     |
| 65  |     |     |     |     | 70  |     |     |     |     | 75  |     |     |     |     | 80  |     |

| ATC | AGC | AGT | GTG | AAG | ACT | GAA | GAC | CTG | GCA | GTT | TAT | TAC | TGT | CAG | CAG | 288 |
| Ile | Ser | Ser | Val | Lys | Thr | Glu | Asp | Leu | Ala | Val | Tyr | Tyr | Cys | Gln | Gln |     |
|     |     |     |     | 85  |     |     |     |     | 90  |     |     |     |     | 95  |     |     |

| TAT | TAT | AGC | TAT | CCC | CTC | ACG | TTC | GGT | GCT | GGG | ACC | AAG | CTT | GTG | CTG | 336 |
| Tyr | Tyr | Ser | Tyr | Pro | Leu | Thr | Phe | Gly | Ala | Gly | Thr | Lys | Leu | Val | Leu |     |
|     |     |     | 100 |     |     |     |     | 105 |     |     |     |     | 110 |     |     |     |

| AAA | GGC | TCT | ACT | TCC | GGT | AAA | CCA | TCT | GAA | GGT | AAA | GGT | GAA | GTT | AAA | 384 |
| Lys | Gly | Ser | Thr | Ser | Gly | Lys | Pro | Ser | Glu | Gly | Lys | Gly | Glu | Val | Lys |     |
|     |     |     | 115 |     |     |     |     | 120 |     |     |     |     | 125 |     |     |     |

| CTG | GAT | GAG | ACT | GGA | GGA | GGC | TTG | GTG | CAA | CCT | GGG | AGG | CCC | ATG | AAA | 432 |
| Leu | Asp | Glu | Thr | Gly | Gly | Gly | Leu | Val | Gln | Pro | Gly | Arg | Pro | Met | Lys |     |
|     |     | 130 |     |     |     |     | 135 |     |     |     |     | 140 |     |     |     |     |

| CTC | TCC | TGT | GTT | GCC | TCT | GGA | TTC | ACT | TTT | AGT | GAC | TAC | TGG | ATG | AAC | 480 |
| Leu | Ser | Cys | Val | Ala | Ser | Gly | Phe | Thr | Phe | Ser | Asp | Tyr | Trp | Met | Asn |     |
| 145 |     |     |     |     | 150 |     |     |     |     | 155 |     |     |     |     | 160 |     |

| TGG | GTC | CGC | CAG | TCT | CCA | GAG | AAA | GGA | CTG | GAG | TGG | GTA | GCA | CAA | ATT | 528 |
| Trp | Val | Arg | Gln | Ser | Pro | Glu | Lys | Gly | Leu | Glu | Trp | Val | Ala | Gln | Ile |     |
|     |     |     |     | 165 |     |     |     |     | 170 |     |     |     |     | 175 |     |     |

| AGA | AAC | AAA | CCT | TAT | AAT | TAT | GAA | ACA | TAT | TAT | TCA | GAT | TCT | GTG | AAA | 576 |
| Arg | Asn | Lys | Pro | Tyr | Asn | Tyr | Glu | Thr | Tyr | Tyr | Ser | Asp | Ser | Val | Lys |     |
|     |     |     | 180 |     |     |     |     | 185 |     |     |     |     | 190 |     |     |     |

| GGC | AGA | TTC | ACC | ATC | TCA | AGA | GAT | GAT | TCC | AAA | AGT | AGT | GTC | TAC | CTG | 624 |
| Gly | Arg | Phe | Thr | Ile | Ser | Arg | Asp | Asp | Ser | Lys | Ser | Ser | Val | Tyr | Leu |     |
|     |     | 195 |     |     |     |     | 200 |     |     |     |     | 205 |     |     |     |     |

| CAA | ATG | AAC | AAC | TTA | AGA | GTT | GAA | GAC | ATG | GGT | ATC | TAT | TAC | TGT | ACG | 672 |
| Gln | Met | Asn | Asn | Leu | Arg | Val | Glu | Asp | Met | Gly | Ile | Tyr | Tyr | Cys | Thr |     |

|     |     |     |     |     |     |     |     |     |     |     |     |     |     |     |
| --- | --- | --- | --- | --- | --- | --- | --- | --- | --- | --- | --- | --- | --- | --- |
|     |     |     | 210 |     |     |     | 215 |     |     |     |     | 220 |     |     |
| GGT | TCT | TAC | TAT | GGT | ATG | GAC | TAC | TGG | GGT | CAA | GGA | ACC | TCA | GTC | ACC | 720 |
| Gly | Ser | Tyr | Tyr | Gly | Met | Asp | Tyr | Trp | Gly | Gln | Gly | Thr | Ser | Val | Thr |
| 225 |     |     |     |     | 230 |     |     |     |     | 235 |     |     |     |     | 240 |
| GTC | TCC | TAATAAGGAT | CC |     |     |     |     |     |     |     |     |     |     |     |     | 738 |
| Val | Ser |

( 2 ) INFORMATION FOR SEQ ID NO:23:

( i ) SEQUENCE CHARACTERISTICS:
        ( A ) LENGTH: 242 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| Asp | Val | Val | Met | Ser | Gln | Ser | Pro | Ser | Ser | Leu | Pro | Val | Ser | Val | Gly |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Glu | Lys | Val | Thr | Leu | Ser | Cys | Lys | Ser | Ser | Gln | Ser | Leu | Leu | Tyr | Ser |
|     |     |     | 20 |     |     |     |     | 25 |     |     |     |     | 30 |     |     |
| Gly | Asn | Gln | Lys | Asn | Tyr | Leu | Ala | Trp | Tyr | Gln | Gln | Lys | Pro | Gly | Gln |
|     |     | 35 |     |     |     |     | 40 |     |     |     |     | 45 |     |     |     |
| Ser | Pro | Lys | Leu | Leu | Ile | Tyr | Trp | Ala | Ser | Ala | Arg | Glu | Ser | Gly | Val |
|     | 50 |     |     |     |     | 55 |     |     |     |     | 60 |     |     |     |     |
| Pro | Asp | Arg | Phe | Thr | Gly | Ser | Gly | Ser | Gly | Thr | Asp | Phe | Thr | Leu | Ser |
| 65 |     |     |     |     | 70 |     |     |     |     | 75 |     |     |     |     | 80 |
| Ile | Ser | Ser | Val | Lys | Thr | Glu | Asp | Leu | Ala | Val | Tyr | Tyr | Cys | Gln | Gln |
|     |     |     |     | 85 |     |     |     |     | 90 |     |     |     |     | 95 |     |
| Tyr | Tyr | Ser | Tyr | Pro | Leu | Thr | Phe | Gly | Ala | Gly | Thr | Lys | Leu | Val | Leu |
|     |     |     | 100 |     |     |     |     | 105 |     |     |     |     | 110 |     |     |
| Lys | Gly | Ser | Thr | Ser | Gly | Lys | Pro | Ser | Glu | Gly | Lys | Gly | Glu | Val | Lys |
|     |     | 115 |     |     |     |     | 120 |     |     |     |     | 125 |     |     |     |
| Leu | Asp | Glu | Thr | Gly | Gly | Gly | Leu | Val | Gln | Pro | Gly | Arg | Pro | Met | Lys |
|     | 130 |     |     |     |     | 135 |     |     |     |     | 140 |     |     |     |     |
| Leu | Ser | Cys | Val | Ala | Ser | Gly | Phe | Thr | Phe | Ser | Asp | Tyr | Trp | Met | Asn |
| 145 |     |     |     |     | 150 |     |     |     |     | 155 |     |     |     |     | 160 |
| Trp | Val | Arg | Gln | Ser | Pro | Glu | Lys | Gly | Leu | Glu | Trp | Val | Ala | Gln | Ile |
|     |     |     |     | 165 |     |     |     |     | 170 |     |     |     |     | 175 |     |
| Arg | Asn | Lys | Pro | Tyr | Asn | Tyr | Glu | Thr | Tyr | Tyr | Ser | Asp | Ser | Val | Lys |
|     |     |     | 180 |     |     |     |     | 185 |     |     |     |     | 190 |     |     |
| Gly | Arg | Phe | Thr | Ile | Ser | Arg | Asp | Asp | Ser | Lys | Ser | Ser | Val | Tyr | Leu |
|     |     | 195 |     |     |     |     | 200 |     |     |     |     | 205 |     |     |     |
| Gln | Met | Asn | Asn | Leu | Arg | Val | Glu | Asp | Met | Gly | Ile | Tyr | Tyr | Cys | Thr |
|     | 210 |     |     |     |     | 215 |     |     |     |     | 220 |     |     |     |     |
| Gly | Ser | Tyr | Tyr | Gly | Met | Asp | Tyr | Trp | Gly | Gln | Gly | Thr | Ser | Val | Thr |
| 225 |     |     |     |     | 230 |     |     |     |     | 235 |     |     |     |     | 240 |
| Val | Ser |